(12) United States Patent
Lowell et al.

(10) Patent No.: US 8,709,447 B2
(45) Date of Patent: Apr. 29, 2014

(54) COMPOSITIONS AND METHODS FOR ACTIVATING INNATE AND ALLERGIC IMMUNITY

(75) Inventors: George H. Lowell, Hampstead (CA); David S. Burt, Dollard des Ormeaux (CA); David Hugh Jones, Mountain View (CA); Joseph J. Zimmermann, Kirkland (CA); Clement Rioux, Ile Bizard (CA)

(73) Assignee: ID Biomedical Corporation of Quebec, Yille St. Laurent, QC (CA)

( * ) Notice: Subject to any disclaimer, the term of this patent is extended or adjusted under 35 U.S.C. 154(b) by 0 days.

(21) Appl. No.: 13/457,223

(22) Filed: Apr. 26, 2012

(65) Prior Publication Data
US 2012/0276140 A1    Nov. 1, 2012

Related U.S. Application Data

(62) Division of application No. 10/972,062, filed on Oct. 22, 2004, now Pat. No. 8,173,140.

(60) Provisional application No. 60/559,842, filed on Apr. 6, 2004, provisional application No. 60/513,614, filed on Oct. 22, 2003.

(51) Int. Cl.
| | |
|---|---|
| *A61K 39/35* | (2006.01) |
| *A61K 39/36* | (2006.01) |
| *A61K 39/116* | (2006.01) |
| *A61K 45/00* | (2006.01) |
| *A61K 47/00* | (2006.01) |
| *A61K 39/00* | (2006.01) |
| *A61K 39/38* | (2006.01) |

(52) U.S. Cl.
USPC .................. 424/275.1; 424/203.1; 424/278.1; 424/184.1

(58) Field of Classification Search
CPC ............... A61K 2300/00; A61K 2039/55561; A61K 39/39; A61K 45/06; A61K 38/19; A61K 31/7105; A61K 31/00; A61K 31/7088; A61K 31/7125; A61K 39/395; A61K 2039/55544; A61K 31/138; A61K 31/473; A61K 31/495; A61K 31/55; A61K 31/557; A61K 31/675; A61K 31/7115; A61K 38/212; A61K 2039/5572; A61K 2039/57; A61K 31/205; A61K 31/4745; A61K 31/522; A61K 31/56; A61K 31/70; A61K 31/712; A61K 39/00; A61K 2039/55511; A61K 2039/55522; A61K 2039/5555; A61K 2039/55555; A61K 2039/55566; A61K 2039/55577; A61K 31/34; A61K 31/38; A61K 31/47; A61K 39/0005; A61K 2039/6025; A61K 2039/6087
See application file for complete search history.

(56) References Cited

U.S. PATENT DOCUMENTS

| | | | |
|---|---|---|---|
| 4,707,543 A | 11/1987 | Zollinger et al. | |
| 5,726,292 A | 3/1998 | Lowell | |
| 5,985,284 A | 11/1999 | Lowell | |
| 5,985,285 A | 11/1999 | Titball et al. | |
| 6,476,201 B1 | 11/2002 | Lowell et al. | |
| 6,743,900 B2 | 6/2004 | Burt et al. | |
| 6,803,042 B2 | 10/2004 | Lowell | |
| 7,368,537 B2 | 5/2008 | Anderson et al. | |
| 7,399,840 B2 | 7/2008 | Burt et al. | |
| 7,524,509 B2* | 4/2009 | Burt et al. .................. | 424/234.1 |
| 7,915,381 B2 | 3/2011 | Aderem et al. | |
| 8,173,140 B2 | 5/2012 | Lowell et al. | |
| 2001/0053368 A1 | 12/2001 | Burt et al. | |
| 2003/0026780 A1 | 2/2003 | Hood et al. | |
| 2003/0044425 A1 | 3/2003 | Burt et al. | |
| 2003/0044429 A1 | 3/2003 | Aderem et al. | |
| 2004/0156867 A1 | 8/2004 | Burt et al. | |
| 2004/0166120 A1 | 8/2004 | Thomas et al. | |
| 2005/0147627 A1 | 7/2005 | Aderem et al. | |
| 2005/0152919 A1 | 7/2005 | Ward et al. | |
| 2006/0229233 A1 | 10/2006 | Frenkel et al. | |
| 2006/0286124 A1 | 12/2006 | Burt et al. | |
| 2008/0260781 A1 | 10/2008 | Burt et al. | |
| 2009/0175903 A1 | 7/2009 | Ward et al. | |
| 2009/0252762 A1* | 10/2009 | Burt et al. .................. | 424/206.1 |
| 2009/0318337 A1 | 12/2009 | Lowell et al. | |
| 2009/0324639 A1 | 12/2009 | Lowell et al. | |

FOREIGN PATENT DOCUMENTS

| | | |
|---|---|---|
| WO | 96/28551 A1 | 9/1996 |
| WO | 02/09748 A1 | 2/2002 |
| WO | 02/072012 A2 | 9/2002 |

(Continued)

OTHER PUBLICATIONS

Schappi et al., J Allergy Clin Immunol, 1997; 100: 656-61.*

(Continued)

*Primary Examiner* — Vanessa L Ford
*Assistant Examiner* — Lakia Tongue
(74) *Attorney, Agent, or Firm* — Michael M. Conger

(57) ABSTRACT

Methods for making and using therapeutic formulations of Proteosome-based immunoactive compositions are provided. The immunogenic compositions, which include Proteosomes and liposaccharides, may be used to elicit or enhance a non-specific innate immune response to, for example, treat or prevent infectious disease. In addition, after activating the innate immune system, immunogenic compositions further containing an antigen may be used to elicit a specific adaptive immune response. Furthermore, provided are compositions capable of altering hyperreactive responses or inflammatory immune responses, such as allergic reactions. Such compositions may be used as a prophylactic, or in various clinical settings to treat or prevent infectious disease (such as parasite, fungal, bacterial or viral infections), or to alter inappropriate inflammatory immune responses (such as allergic reactions or asthma).

9 Claims, 17 Drawing Sheets

(56) References Cited

FOREIGN PATENT DOCUMENTS

| WO | WO 02/072012 A2 * | 9/2002 |
| --- | --- | --- |
| WO | 2004/098636 A2 | 11/2004 |
| WO | 2005/007189 A1 | 1/2005 |
| WO | 2005/042017 A1 | 5/2005 |
| WO | 2006/004749 A2 | 1/2006 |
| WO | 2006/068663 A2 | 6/2006 |

OTHER PUBLICATIONS

Stoloff, Clinical Cornerstone, 2008; 9(2): 6-23.*

Elliott et al., J Allergy Clin Immunol, 1999; 104: 294-300.*

Chabot et al., "A novel intranasal Protollin™-based measles vaccine induces mucosal and systemic neutralizing antibody responses and cell-mediated immunity in mice," Vaccine 23:1374-1383, 2005.

Jones et al., "Intranasal Protollin™/F1-V vaccine elicits respiratory and serum antibody responses and protects mice against lethal aerosolized plague infection," Vaccine 24:1625-1632, 2006.

Levi et al., "Intranasal immunization of mice against influenza with synthetic peptides anchored to proteosomes," Vaccine 13(14):1353-1359, 1995.

Van De Verg et al., "Antibody and Cytokine Responses in a Mouse Pulmonary Model of Shigella flexneri Serotype 2a Infection," Infection and Immunity 63(5):1947-1954, May 1995.

Anderson et al., "Recombinant V Antigen Protects Mice against Pneumonic and Bubonic Plague Caused by F1-Capsule-Positive and -Negative Strains of Yersinia pestis," Infection and Immunity 64(11):4580-4585, Nov. 1996.

Beutler et al., "How we detect microbes and respond to them: the Toll-like receptors and their transducers," Journal of Leukocyte Biology 74:479-485, 2003.

Boslego et al., Chapter 17, "Gonorrhea Vaccines," in Vaccines, W. B. Saunders Company, 1988, pp. 211-223.

Burt et al., "Protollin™—A Novel Mucosal Adjuvant for the Activation of Innate and Adaptive Immunity," Clinical and Investigative Medicine 27(4), Abstract No. 4613, Abstracts of the 12$^{th}$ International Congress of Immunology and 4$^{th}$ Annual Conference of FOCIS, Jul. 2004, URL=www.immuno2004.org/onlineabstracts/4613.html, retrieved on Apr. 7, 2005.

Clerici et al., "Vaccine strategies for infectious diseases," Expert Opinion Investigational Drugs 8(2):95-106, 1999.

Deepe, "Prospects for the Development of Fungal Vaccines," Clinical Microbiology Reviews 10(4):585-596, Oct. 1997.

DeMets, "Chlamydia trachomatis," Bacteriology at UW-Madison 330 Lecture Topic, URL=http://www.bact.wisc.edu/bact330/lecturechlamydia, 1998, accessed on Aug. 31, 2005.

Ellis, Chapter 29, "New Technologies for Making Vaccines," in Vaccines, W. B. Saunders Company, 1988, pp. 568-575.

Fearon et al., "The Instructive Role of Innate Immunity in the Acquired Immune Response," Science 272:50-54, Apr. 5, 1996.

Fries et al., "Safety and Immunogenicity of Proteosome-Shigella flexneri 2a Lipopolysaccharide Vaccine Administered Intranasally to Healthy Adults," Infection and Immunity 69(7):4545-4553, Jul. 2001.

Gavett et al., "Interleukin 12 Inhibits Antigen-induced Airway Hyperresponsiveness, Inflammation, and Th2 Cytokine Expression in Mice," J. Exp. Med. 182:1527-1536, Nov. 1995.

Hoffman et al., "Phylogenetic Perspectives in Innate Immunity," Science 284:1313-1318, May 21, 1999.

Humbles et al., "A Critical Role for Eosinophils in Allergic Airways Remodeling," Science 305:1776-1779, Sep. 17, 2004.

Jahn-Schmid, Toward Selective Elicitation of $T_H1$-controlled Vaccination Responses: Vaccine Applications of Bacterial Surface Layer Proteins, Journal of Biotechnology 44(1996) 225-231.

Jones et al., "Protollin™: a novel adjuvant for intranasal vaccines," Vaccine 22:3691-3697, 2004.

Kline et al., "Cutting Edge: Modulation of Airway Inflammation by CpG Oligodeoxynucleotides in a Murine Model of Asthma," Journal of Immunology 160:2555-2559, 1998.

Lack et al., "Nebulized IFN-γ Inhibits the Development of Secondary Allergic Responses in Mice," Journal of Immunology 157:1432-4139, 1996.

Lawton et al., "Novel therapeutic strategies based on toll-like receptor signaling," Current Opinion in Chemical Biology 7:446-451, 2003.

Lee et al., "Defining a Link with Asthma in Mice Congenitally Deficient in Eosinophils," Science 305:1773-1776, Sep. 17, 2004.

Lindler et al., "Complete DNA Sequence and Detailed Analysis of the Yersinia pestis KIM5 Plasmid Encoding Murine Toxin and Capsular Antigen," Infection and Immunity 66(12):5731-5742, Dec. 1998.

Lowell et al., "Peptides Bound to Proteosomes Via Hydrophobic Feet Become Highly Immunogenic Without Adjuvants," Journal of Experimental Medicine 167(2):658-663, Feb. 1, 1988.

Lowell et al., "Proteosome-Lipopeptide Vaccines- Enhancement of Immunogenicity for Malaria CS Peptides," Science 240:800-802, May 6, 1988.

Lowell, New Generation Vaccines, 2$^{nd}$ Edition, Marcel Dekker, Inc., New York, Chapter 15, "Proteosomes for Improved Nasal, Oral, or Injectable Vaccines," pp. 193-206, 1997.

Lynch et al., "Spontaneously Transferred from Whole Cells and Reconstituted from Purified Proteins of Neisseria gonorrhoeae and Neisseria meningitidis," Biophysical Journal, 45(1):104-107, Jan. 1984.

Mallett et al., "Intranasal or Intragastric Immunization with Proteosome—Shigella Lipopolysaccharide Vaccines Protects against Lethal Pneumonia in a Murine Model of Shigella Infection," Infection and Immunity 63(6):2382-2386, Jun. 1995.

Medzhitov et al., "Innate immunity: impact on the adaptive immune response," Current Opinion In Immunology 9:4-9, 1997.

Medzhitov et al., "The Toll receptor family and microbial recognition," Trends in Microbiology 8(10):452-456, Oct. 2000.

Milush et al., "Mucosal Innate Immune Response Associated with a Timely Humoral Immune Response and Slower Disease Progression after Oral Transmission of Simian Immunodeficiency Virus to Rhesus macaques," Journal of Virology 81(12):6175-6186, Jun. 2007.

O'Neill, "Toll-like receptor signal transduction and the tailoring of innate immunity: a role for Mal?," TRENDS in Immunology 23(6):296-300, 2002.

Orr et al., "Immunogenicity and Efficacy of Oral or Intranasal Shigella flexneri 2a and Shigella sonnei Proteosome-Lipopolysaccharide Vaccines in Animal Models," Infection and Immunity 61(6):2390-2395, Jun. 1993.

Peterson et al., "Characterization of a Neutralizing Monoclonal Antibody Directed at the Lipopolysaccharide of Chlamydia pneumoniae," Infection and Immunity 66(8):3848-3855, Aug. 1998.

Stedman's Online Medical Dictionary, Definition: Immunity, accessed Aug. 31, 2005, URL=http://216.251.232.159/semdweb/internetsomdlASPI1528142.asp.

Wetzler et al., "Immune Stimulation by Neisserial Porins is TLR2 and MyD88 Dependent," Abstracts of the General Meeting of the American Society for Microbiology 102:189, 2002.

* cited by examiner

Manufacture of S. flexneri 2a LPS: FLOW CHART 2

*Fig. 2*

```
┌─────────────────────────────────────────┐
│ Production seed S. flex. BS 103 into 3 X 1L │
│ shaker flasks of trypticase soy broth suppl.│
│ with glucose and MgSO₄. Incubated at        │
│ 37° C X 16-24 hours                         │
└─────────────────────────────────────────┘
                    ↓
┌─────────────────────────────────────────┐
│ 300 L fermentation, trypticase soy broth suppl.│      *agitation rate varied to maintain
│ with glucose and MgSO₄ 250 rpm agit.*, 37° C, │        dissolved O₂ ≥ 25%
│ pH 7.5, 300 L/min. O₂                         │
└─────────────────────────────────────────┘         ┌──────────────────────────────┐
                    ↓  ←─────────────────────────── │ Fermentation to stationary   │
                                                    │ by OD₆₀₀ (9-10 hours)        │
                                                    └──────────────────────────────┘
┌─────────────────────────────────────────┐
│ Cool to 10° C, harvest in continuous    │
│ feed centrifuge                         │
└─────────────────────────────────────────┘
                    ↓
┌─────────────────────────────────────────┐
│ Rehydrate paste X 1 hour at R.T. in 3 mL│
│ of 0.9M NaCl, 0.005 M EDTA and          │
│ 10 mg lysozyme per g paste              │
└─────────────────────────────────────────┘
                    ↓
┌─────────────────────────────────────────┐
│ Add Dnase to 50 u/mL and MgCl₂          │
│ to 0.025M, inc. 30 min. at R.T.         │
└─────────────────────────────────────────┘
                    ↓
┌─────────────────────────────────────────┐
│ Homogenize in microfluidizer            │
│ 14,000 to 19,000 psi                    │
└─────────────────────────────────────────┘
                    ↓
┌─────────────────────────────────────────┐
│ Fresh Dnase to 50 u/mL inc. 30 min. at R.T.│
└─────────────────────────────────────────┘
                    ↓
┌─────────────────────────────────────────┐
│ Heat to 68° C, add = vol. 90% phenol    │
│ Incubate 68° C x 30 min., shaking       │
└─────────────────────────────────────────┘
                    ↓
┌─────────────────────────────────────────┐          ┌──────────────────────────────┐
│ Cfg. At 4° C, harvest aqueous phase     │─────────→│ Reserve aqueous phase        │
└─────────────────────────────────────────┘          └──────────────────────────────┘
                    ↓                                              ↑
┌─────────────────────────────────────────┐                        │
│ Repeat extraction of phenol phase x 2 with WFI │─────────────────┘
│ at 68° C, pool all aqueous phase materials     │
└─────────────────────────────────────────┘          ┌──────────────────────────────┐
                    ↓ ──────────────────────────────→│ Discard phenol phase         │
                                                     └──────────────────────────────┘
┌─────────────────────────────────────────┐
│ Add EtOH to 15%, CaCl₂ to 10 mM         │
│ Inc. 1 hr. at R.T., cfg. 10,000 X G     │
└─────────────────────────────────────────┘          ┌──────────────────────────────┐
                    ↓ ──────────────────────────────→│ Discard pellet               │
                                                     └──────────────────────────────┘
┌─────────────────────────────────────────┐
│ Concentrate, diafilter on 10,000 MW membrane │
│ into 0.15 M NaCl, 0.05 M Tris, 0.01 M EDTA,  │
│ 0.1% EMPIGEN, pH 8.0                         │
└─────────────────────────────────────────┘
                    ↓
┌─────────────────────────────────────────┐          ┌──────────────────────────────┐
│ 0.22 μm aseptic filtration              │─────────→│ LPS BULK, store -80° C       │
└─────────────────────────────────────────┘          └──────────────────────────────┘
```

COMPOSITIONS AND METHODS FOR ACTIVATING INNATE AND ALLERGIC IMMUNITY

CROSS-REFERENCE TO RELATED APPLICATION

This application is a divisional of U.S. Pat. No. 10/972,062, filed Oct. 22, 2004, now issued on May 8, 2012 as U.S. Pat. No. 8,173,840; which claims the benefit of U.S. Provisional Patent Applications No. 60/513,614 filed Oct. 22, 2003 and No. 60/559,842 filed Apr. 6, 2004, all of which applications are incorporated herein by reference in their entireties.

BACKGROUND OF THE INVENTION

1. Field of the Invention

The present invention relates generally to immunomodulation and, more specifically, to therapeutic uses of immunostimulatory Proteosome compositions for inducing a nonspecific immune response (such as an innate immune response) so that an adaptive immune response is potentiated or enhanced, or to induce both a nonspecific immune response and a specific adaptive immune response, such that infectious disease is treated or prevented, or to modulate an immune response for treating or preventing an inflammatory reaction, such as allergic asthma.

2. Description of the Related Art

Some microbial pathogens are capable of causing fatal infections even when faced with a robust host immune response. Nonetheless, control of rampant infectious disease has been generally successful in modern society by using strict public health measures, drugs (such as antibiotics), and vaccines. Vaccines typically include an attenuated microbe or a microbial antigen to activate a specific (adaptive) immune response. The ability of an antigen to induce a protective immune response in a host can be enhanced by formulating the antigen with an immunostimulant or an adjuvant. Alum-based adjuvants are almost exclusively used for licensed, injectable human vaccines. However, the adaptive immune response requires signals that provide information about the origin of the antigen (i.e., self versus non-self antigens) and the type of response to be induced (i.e., a T cell and/or B cell response). Evidence recently accumulated indicates that these signals may be provided by the innate immune system (see, e.g., Fearon and Locksley, *Science* 272:50, 1996; Medzhitov and Janeway, *Curr. Opin. Immunol.* 9:4, 1997).

Innate immunity is the first line of antibody-independent defense against infections and, in many instances, can eliminate infectious agents. The components of innate immunity recognize structures that are characteristic of microbial pathogens and are not present on mammalian cells. The principle effector cells of innate immunity are neutrophils, mononuclear phagocytes, and natural killer (NK) cells. Neutrophils and macrophages express surface receptors that recognize microbes in the blood and tissues, and either stimulate the ingestion (phagocytosis, e.g., mannose or opsonin receptors) or activate phagocytes not involved in ingestion (e.g., Toll-like receptors, TLRs). The effector mechanisms of innate immunity are often used to eliminate microbes, even in an adaptive immune response. Thus, the innate immune response can provide signals that function in concert with antigen to stimulate the proliferation and differentiation of antigen-specific (adaptive) T and B lymphocytes.

An efficient immune response depends on the communication between the innate and adaptive immune responses. The T lymphocyte is important for coordinating the adaptive immune response by controlling the release of effector molecules. For example, T helper (Th) 1 cells produce interleukin-2 (IL-2), tumor necrosis factor alpha (TNF-α), and interferon gamma (IFN-γ), which are important for the development of cell-mediated immunity (Mosmann et al., *J. Immunol.* 136: 2348, 1986; Street and Mosmann, *FASEB J.* 5: 171, 1991). In contrast, Th2 cells produce IL-4, IL-13, IL-5, IL-9, IL-6 and IL-10, which are important for the stimulation of IgE production, mucosal mastocytosis, and eosinophilia (Mosmann et al.; Street and Mosmann). While a shift toward a Th1 or Th2 phenotype may be important for the defense against pathogens, a shift in one direction or another can also be associated with the induction of autoimmune disease (Th1) or inflammatory disease (Th2).

In inflammatory diseases, such as allergy or asthma, the fine balance between the Th1, Th2 and T regulatory cytokine responses appears to shift toward a Th2 phenotype. For example, asthma is a complex inflammatory disease of the lung characterized by variable airflow obstruction, airway hyperresponsiveness (AHR), and airway inflammation. Although asthma is multifactorial in origin, the inflammatory process (in the most common form of asthma, referred to as extrinsic or allergic asthma) is believed to be the result of an abnormal immune response to commonly inhaled allergens. The presentation of inhaled allergens to CD4+ T cells in the lungs of susceptible individuals results in the production of Th2 cytokines, IL-4, IL-13 and IL-5, which control the differentiation, recruitment, and activation of mast cells and eosinophils in the airway mucosa. These effector cells release a variety of inflammatory mediators (e.g., histamine, mucous secretogues, eosinophil-derived basic proteins, proteases). The mediators either individually or in concert cause acute bronchoconstriction, disruption of the airway epithelial layer, alterations in neural control of airway tone, increased mucus production, and increased smooth muscle cell mass. Each of these consequences of the inflammatory process may cause or occur in combination with AHR. The incidence, morbidity, and mortality of asthma has increased worldwide over the last two decades, and the existing anti-inflammatory medications (such as corticosteroids) have limitations in that the disease is not modified (i.e., only the symptoms are treated, which will return if the medication is discontinued) and these medications are associated with the potential for significant side effects.

Hence, a need exists for identifying and developing immunostimulatory compositions that are therapeutically effective against microbial infections and immunopathologic (e.g., inflammatory) responses to such infections, particularly compositions that can potentiate or enhance protective immunity, and compositions that can suppress an immunopathologic response. The present invention meets such needs, and further provides other related advantages.

BRIEF SUMMARY OF THE INVENTION

The invention described herein provides methods for making and using therapeutic formulations of Proteosome-based immunoactive compositions. Immunostimulatory compositions, which include Proteosomes and liposaccharides, may be used to elicit or enhance a nonspecific innate immune response to treat or prevent infectious disease. In addition, after activating the innate immune system, immunogenic compositions further containing an antigen may be used to elicit a specific adaptive immune response. Furthermore, provided are compositions capable of altering hyperreactive responses or inflammatory immune responses, such as allergic reactions.

In one embodiment of the invention is provided a method for eliciting a nonspecific immune response, comprising administering to a subject an immunostimulatory composition in an amount sufficient to elicit a nonspecific immune response, wherein the immunostimulatory composition comprises Proteosomes and liposaccharide. In one embodiment, the nonspecific immune response is an innate immune response that prevents or treats a microbial infection, wherein the microbial infection is a viral, parasitic, fungal, or bacterial infection. In a particular embodiment, the microbial infection is a viral infection, wherein the viral infection is an influenza infection. In one embodiment, the immunostimulatory composition is administered by a route selected from at least one of mucosal, enteral, parenteral, transdermal, transmucosal, nasal, and inhalation. In an embodiment, the liposaccharide final content by weight as a percentage of Proteosome protein ranges from about 1% to 500%. In certain embodiments, the proteosomes and liposaccharide are obtained from the same Gram-negative bacterial species, or the proteosomes are obtained from a first Gram-negative bacterial species and the liposaccharide is obtained from a second Gram-negative bacterial species. In a particular embodiment, the liposaccharide is obtained from a Gram-negative bacterium selected from at least one of *Shigella* species, *Chlamydia* species, *Yersinia* species, *Pseudomonas* species, *Plesiomonas* species, *Escherichia* species, *Porphyromonas* species, and *Salmonella* species. In a particular embodiment, the Proteosomes are obtained from *Neisseria* species, and in another particular embodiment, the Proteosomes are obtained from *Neisseria meningitidis*, and the liposaccharide is obtained from *Shigella flexneri*.

In another embodiment, the method provided further comprises administering to the subject an immunogenic composition after administering the immunostimulatory composition, wherein the immunogenic composition comprises Proteosomes, liposaccharide, and a microbial antigen, wherein the microbial antigen is a viral antigen, a bacterial antigen, a fungal antigen, or a parasitic antigen. In a particular embodiment, the microbial antigen is recombinant. In other embodiments, the microbial antigen is a bacterial antigen obtained from *Bacillus anthracis, Chlamydia trachomatis, Yersinia pestis*, or Enteropathogenic *Escherichia coli*. In a particular embodiment, the bacterial antigen is Protective Antigen from *Bacillus anthracis*. In another particular embodiment, the microbial antigen is a viral split antigen, wherein the viral split antigen is an influenza split antigen. In certain embodiments, the immunogenic composition comprises at least two microbial antigens, which may be obtained from the same microorganism, which is a virus, bacteria, fungus, or protozoa, or may be obtained from different microorganisms. The immunogenic composition elicits an adaptive immune response according to certain embodiments. According to particular embodiments, the ratio of the weight of Proteosomes and liposaccharide of the immunogenic composition to the weight of the microbial antigen of the immunogenic composition is within a range from 4:1 to 1:4, 1:1 to 1:500, or 1:1 to 1:200. In other embodiments, the immunogenic composition is administered about one to about ten days or about one to seven days after the immunostimulatory composition, and in other certain embodiments, at least one of the immunostimulatory composition and the immunogenic composition further comprise a pharmaceutically acceptable carrier.

The invention also provides a method for treating or preventing a microbial infection, comprising (a) administering to a subject an immunostimulatory composition, wherein the immunostimulatory composition comprises Proteosomes and liposaccharide, in an amount and under conditions sufficient to elicit an innate immune response; and (b) administering to the subject an immunogenic composition, wherein the immunogenic composition comprises Proteosomes, liposaccharide, and a microbial antigen, in an amount and under conditions sufficient to elicit an adaptive immune response, such that the microbial infection is treated or prevented, wherein the microbial infection is a viral, parasitic, fungal, or bacterial infection. In a particular embodiment, the microbial infection is a viral infection, wherein the viral infection is an influenza infection. In a particular embodiment, the immunostimulatory composition is administered about one to about ten days before the immunogenic composition. In one embodiment, each of the immunostimulatory composition and the immunogenic composition is administered by a route selected from at least one of mucosal, enteral, parenteral, transdermal, transmucosal, nasal, and inhalation; and in a particular embodiment the compositions are administered nasally. According to one embodiment, the liposaccharide final content by weight as a percentage of Proteosome protein ranges from about 1% to 500% in each of the immunostimulatory and immunogenic compositions. In particular embodiments, the Proteosomes and the liposaccharide of the immunostimulatory composition are obtained from the same Gram-negative bacterial species or the Proteosomes and the liposaccharide of the immunostimulatory composition are obtained from the different Gram-negative bacterial species. In another particular embodiment, the Proteosomes and the liposaccharide of the immunogenic composition are obtained from the same Gram-negative bacterial species, or the Proteosomes and the liposaccharide of the immunogenic composition are obtained from different Gram-negative bacterial species. In other particular embodiments, the Proteosomes of the immunostimulatory and immunogenic compositions are obtained from *Neisseria* species, and at least one of the liposaccharides of the immunostimulatory and immunogenic compositions is obtained from at least one of *Shigella* species, *Chlamydia* species, *Yersinia* species, *Pseudomonas* species, *Plesiomonas* species, *Escherichia* species, *Porphyromonas* species, and *Salmonella* species. In another specific embodiment, the Proteosomes of each of the immunostimulatory and immunogenic compositions are obtained from *Neisseria meningitidis*, and the liposaccharide of each of the immunostimulatory and immunogenic compositions is from *Shigella flexneri*. the microbial antigen is a viral antigen, a bacterial antigen, a fungal antigen, or a parasitic antigen. In a particular embodiment, the microbial antigen of the immunogenic composition is recombinant. In other embodiments, the microbial antigen is a bacterial antigen obtained from *Bacillus anthracis, Chlamydia trachomatis, Yersinia pestis*, or Enteropathogenic *Escherichia coli*. In a particular embodiment, the bacterial antigen is Protective Antigen from *Bacillus anthracis*. In another particular embodiment, the microbial antigen is a viral split antigen, wherein the viral split antigen is an influenza split antigen. In certain embodiments, the immunogenic composition comprises at least two microbial antigens, which may be obtained from the same microorganism, which is a virus, bacteria, fungus, or protozoa, or may be obtained from different microorganisms. The immunogenic composition elicits an adaptive immune response according to certain embodiments. The immunogenic composition elicits an adaptive immune response according to certain embodiments. According to particular embodiments, the ratio of the weight of Proteosomes and liposaccharide of the immunogenic composition to the weight of the microbial antigen of the immunogenic composition is within a range from 4:1 to 1:4, 1:1 to 1:500, or 1:1 to 1:200. In other embodiments, the immunogenic composition is administered about one to seven days or about one to about ten days after the immunostimulatory composition, and in other certain embodiments, at least one of the immunostimulatory composition and the immunogenic composition further comprise a pharmaceutically acceptable carrier.

Also provided is a method for altering an inflammatory immune response, comprising administering to a subject an immunomodulatory composition in an amount sufficient to alter an inflammatory immune response, wherein the immunomodulatory composition comprises Proteosomes and a liposaccharide, wherein the immunomodulatory composition is administered by a route selected from at least one of mucosal, enteral, parenteral, transdermal, transmucosal, nasal, and inhalation. In a particular embodiment, the liposaccharide final content by weight as a percentage of Proteosome protein ranges from about 1% to 500%. In a certain embodiment, the Proteosomes and liposaccharide are obtained from the same Gram-negative bacterial species, and in another certain embodiment, the Proteosomes and liposaccharide are obtained from different Gram-negative bacterial species. The Gram-negative bacterial species, according to certain embodiments, is selected from at least one of *Shigella* species, *Chlamydia* species, *Yersinia* species, *Pseudomonas* species, *Plesiomonas* species, *Escherichia* species, *Porphyromonas* sp., and *Salmonella* species. In a particular embodiment, the Proteosomes are obtained from *Neisseria* species. In another particular embodiment, the Proteosomes are obtained from *Neisseria meningitidis* and the liposaccharide is obtained from *Shigella flexneri*.

In one embodiment, the method for altering an inflammatory immune response, comprising administering to a subject an immunomodulatory composition in an amount sufficient to alter an inflammatory immune response, wherein the immunomodulatory composition comprises Proteosomes and a liposaccharide further comprises administering to the subject an immunogenic composition after administering the immunomodulatory composition, wherein the immunogenic composition comprises Proteosomes, a liposaccharide, and an antigen. In a certain embodiment, the immunogenic composition comprises at least one microbial antigen, wherein the at least one microbial antigen is viral, bacterial, fungal, or parasitic. According to particular embodiments, the ratio of the weight of Proteosomes and liposaccharide of the immunogenic composition to the weight of the microbial antigen of the immunogenic composition is within a range from 4:1 to 1:4, 1:1 to 1:500, or 1:1 to 1:200. In a particular embodiment, the antigen of the immunogenic composition is recombinant. In another embodiment, the antigen of the immunogenic composition is bacterial, which bacterial antigen is obtained from *Bacillus anthracis, Chlamydia trachomatis, Yersinia pestis*, or Enteropathogenic *Escherichia coli*. In a certain embodiment, the bacterial antigen is Protective Antigen from *Bacillus anthracis*. In another certain embodiment, the antigen of the immunogenic composition is a viral split antigen, and in a particular embodiment, the viral split antigen is an influenza split antigen. In another embodiment, the immunogenic composition is administered about one to about ten days after the immunomodulatory composition, and in another particular embodiment, the immunogenic composition elicits an adaptive immune response. In certain particular embodiments, the inflammatory immune response is asthma or an allergic reaction. According to a particular embodiment, at least one of the immunomodulatory composition and the immunogenic composition further comprises a pharmaceutically acceptable carrier.

Also provided is a method for treating or preventing an allergic reaction, comprising (a) administering to a subject in need thereof an immunomodulatory composition, wherein the immunomodulatory composition comprises Proteosomes and a liposaccharide, in an amount and under conditions sufficient to alter an inflammatory immune response; and (b) administering to the subject an immunogenic composition, wherein the immunogenic composition comprises Proteosomes, liposaccharide, and an allergen, in an amount and under conditions sufficient to elicit tolerance to the allergen, such that the allergic reaction is treated or prevented, wherein each of the immunomodulatory composition and the immunogenic composition is administered by a route selected from at least one of mucosal, enteral, sublingual, parenteral, transdermal, transmucosal, nasal, and inhalation. In a particular embodiment, the immunomodulatory composition is administered about one to about ten days before the immunogenic composition. In one particular embodiment, the liposaccharide final content by weight as a percentage of Proteosome protein ranges from about 1% to 500% in each of the immunomodulatory and immunogenic compositions. In one embodiment, the Proteosomes and liposaccharide of the immunomodulatory composition are obtained from the same Gram-negative bacterial species, and in another embodiment, the Proteosomes and liposaccharide of the immunomodulatory composition are obtained from different Gram-negative bacterial species. In another particular embodiment, the Proteosomes and liposaccharide of the immunogenic composition are obtained from the same Gram-negative bacterial species, and in still another particular embodiment, the Proteosomes and liposaccharide of the immunogenic composition are obtained from different Gram-negative bacterial species. In one particular embodiment, the Proteosomes of each of the immunomodulatory and immunogenic compositions are obtained from *Neisseria* species and the liposaccharide of at least one of the immunomodulatory composition and the immunogenic composition is obtained from at least one of *Shigella* species, *Chlamydia* species, *Yersinia* species, *Pseudomonas* species, *Plesiomonas* species, *Escherichia* species, *Porphyromonas* species, and *Salmonella* species. In a certain particular embodiment, the Proteosomes of each of the immunomodulatory and immunogenic compositions are obtained from *Neisseria meningitidis*, and the liposaccharide of each of the immunomodulatory and immunogenic compositions is obtained from *Shigella flexneri*. In another embodiment, the immunogenic composition further comprises at least two allergens. In another embodiment, the allergen is a microbial antigen. In certain embodiments, the ratio of the weight of Proteosomes and liposaccharide of the immunogenic composition to the weight of the allergen of the immunogenic composition is within a range from 4:1 to 1:4, within a range from 1:1 to 1:500, or within a range from 1:1 to 1:200. In certain particular embodiments, the allergen of the immunogenic composition is recombinant, and in other embodiments, the allergen is a bacterial antigen. In still another embodiment, the allergen of the immunogenic composition is selected from at least one of an inhaled particle, pollen, vapor, gas, food, beverage, drug, toxin, microbial antigen, dander, animal-derived compounds, dust mite feces, polypeptide, carbohydrate, and nucleic acid. In a particular embodiment, the allergen is birch pollen. In another embodiment, the immunogenic composition is administered about one to about seven days or about one to about 10 days after the immunomodulatory composition. In another embodiment, the allergic reaction is at least one of asthma, allergic alveolitis, allergic bronchopulmonary aspergillosis, allergic conjunctivitis, allergic coryza, allergic dermatitis, allergic vasculitis, and allergic rhinitis. In a particular embodiment, at least one of the immunomodulatory composition and the immunogenic composition further comprises a pharmaceutically acceptable carrier.

Also provided herein is a method for treating or preventing a microbial infection comprising administering to a subject an immunostimulatory composition in an amount sufficient to elicit an innate immune response, wherein the immunostimulatory composition comprises Proteosomes and liposaccharide, and wherein the microbial infection is a viral, bacterial, parasitic, or fungal infection. In a particular embodiment, the microbial infection is a bacterial infection, wherein the bacterial infection is a Chlamydia trachomatis infection. In another embodiment, the microbial infection is a viral infection, wherein the viral infection is an influenza infection. In certain embodiments, the immunostimulatory composition is administered by a route selected from at least one of mucosal, enteral, parenteral, transdermal, transmucosal, nasal, and inhalation. In one embodiment, the liposaccharide final content by weight as a percentage of Proteosome protein ranges from about 1% to 500%. In other embodiments, the Proteosomes and liposaccharide are obtained from the same Gram-negative bacterial species, and in another embodiment, the Proteosomes are obtained from a first Gram-negative bacterial species and the liposaccharide is obtained from a second Gram-negative bacterial species. In certain embodiments, the liposaccharide is obtained from a Gram-negative bacterium selected from at least one of Shigella species, Chlamydia species, Yersinia species, Pseudomonas species, Plesiomonas species, Escherichia species, Porphyromonas species, and Salmonella species. In a particular embodiment, Proteosomes are obtained from Neisseria species, and in another particular embodiment, the Proteosomes are obtained from Neisseria meningitidis, and the liposaccharide is obtained from Shigella flexneri.

In one particular embodiment, is provided a method for treating or preventing an influenza virus infection comprising administering to a subject an immunostimulatory composition in an amount sufficient to elicit an innate immune response, wherein the immunostimulatory composition comprises Proteosomes and liposaccharide, wherein Proteosomes are obtained from Neisseria meningitidis, and the liposaccharide is obtained from Shigella flexneri.

These and other aspects of the present invention will become evident upon reference to the following detailed description and attached drawings.

BRIEF DESCRIPTION OF THE DRAWINGS

FIG. 2 represents a scheme for the manufacture of Shigella flexneri 2a LPS (Flow Chart 2).

FIG. 5D shows survival of mice against challenge on day 35 or day 55 with 169 $LD_{50}$ of aerosolized Y. pestis. Mice were immunized twice with 5 µg of F1-V intranasally with Protollin at 2.5 µg, 1 µg, or 0.25 µg or without Protollin. In all studies, animals in the Control group received only Protollin and died when challenged with Y. pestis.

In FIG. 8B, IVX=Protollin.

DETAILED DESCRIPTION OF THE INVENTION

Figure 1A:
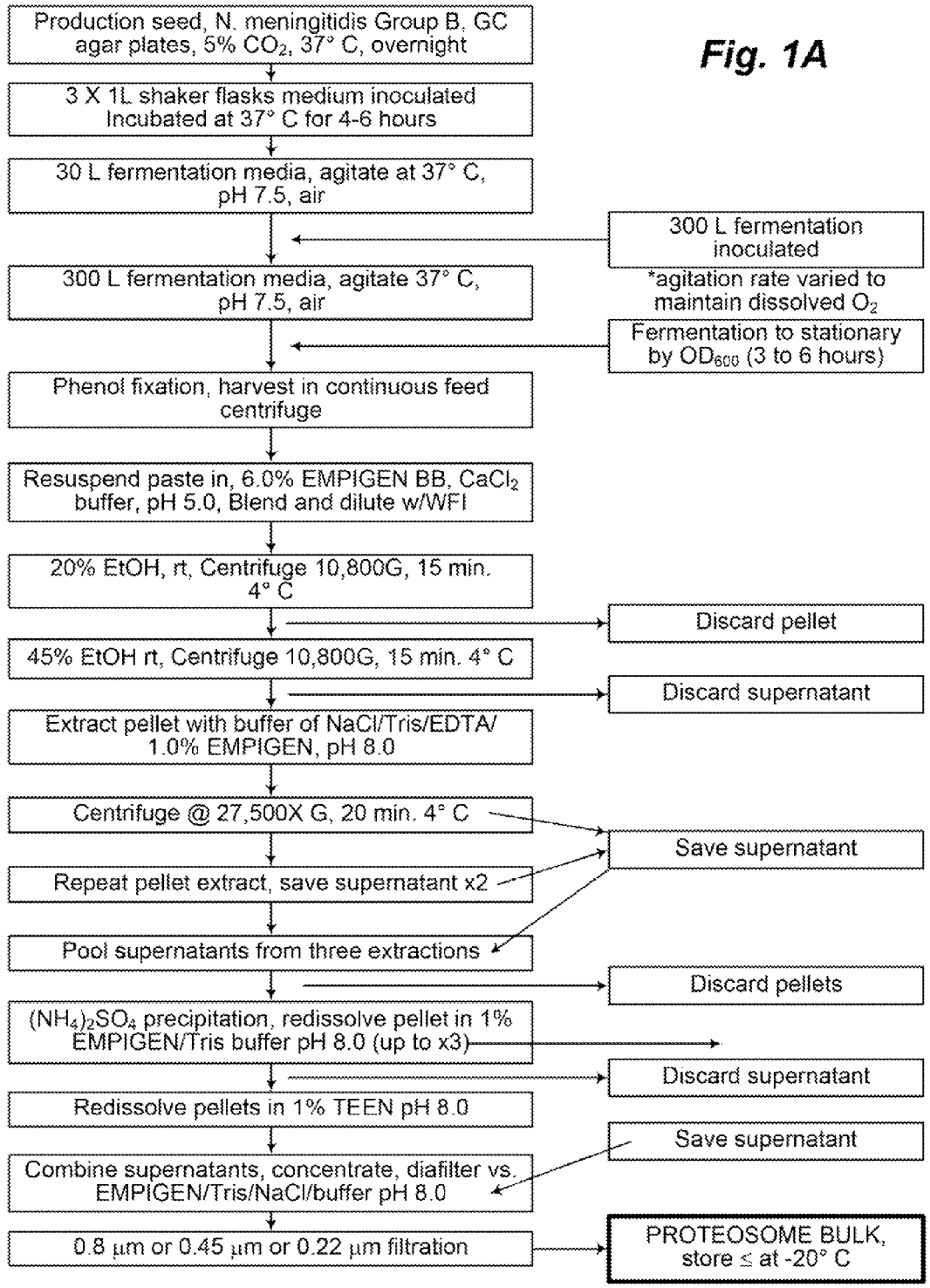
FIGS. 1A and 1B show two methods for manufacturing Proteosome bulk material (Flow Chart 1A and Flow Chart 1B, respectively).

Protollin™ is an outer membrane (OM)-liposaccharide (LPS) adjuvant that includes an outer membrane protein preparation called a Proteosome(s) (also referred to as Projuvant) prepared from Gram-negative bacteria, such as Neisseria meningitidis, and one or more liposaccharides. As described herein, Protollin may be used to elicit a potent innate immune response that provides protection against pathogenic organisms. Therefore, the instant invention relates generally to the surprising discovery that an immunostimulatory composition comprising Protollin can stimulate a broad spectrum, antigen-independent, nonspecific immune response that can protect against a wide variety of infectious agents, including bacteria, viruses, fungi, and protozoa. In addition, Protollin may be used to modulate or alter a detrimental immune response minimizing damage from an overly robust inflammatory response. Hence, the instant description also pertains to the unexpected finding that an immunomodulatory composition comprising Protollin can be used to suppress an inflammatory response, such as airway hyperresponsiveness (AHR), or to alter an immune response, thus minimizing a damaging inflammatory response (e.g., shifting a Th2 response toward a Th1 phenotype). Described in more detail herein are immunostimulatory and immunomodulatory compositions comprising Proteosome:LPS or Proteosomes, as well as immunogenic compositions comprising Proteosome:LPS or Proteosomes formulated with one or more microbial antigens. In certain embodiments, the compositions are suitable for therapeutic uses such as treating or preventing a microbial infection by inducing a specific immune response, a nonspecific immune response, or both types of responses. In other embodiments, the compositions described herein are suitable for treating or preventing an inflammatory immune response, such as allergic asthma or associated complications such as AHR. The instant description also provides methods for preparing any of the compositions described herein.

A Proteosome or Projuvant refers to a preparation of outer membrane proteins (OMPs, also known as porins) from Gram-negative bacteria, such as *Neisseria* species (see, e.g., Lowell et al., *J. Exp. Med.* 167:658, 1988; Lowell et al., *Science* 240:800, 1988; Lynch et al., *Biophys. J.* 45:104, 1984; Lowell, in "New Generation Vaccines" 2nd ed., Marcel Dekker, Inc., New York, Basil, Hong Kong, page 193 (1997); U.S. Pat. Nos. 5,726,292; 4,707,543), which is useful as a carrier or an adjuvant for immunogens, such as one or more bacterial or viral antigens. Proteosomes are hydrophobic and comparable in size to certain viruses and are safe for human use. Proteosomes have the capability to auto-assemble into vesicle or vesicle-like OMP clusters of 20-800 nm, and to noncovalently incorporate, coordinate, associate, or interact (e.g., electrostatically or hydrophobically), or otherwise cooperate with protein antigens (Ags), particularly antigens that have a hydrophobic moiety. A Proteosome includes the product of any preparation method that provides an outer membrane protein component in vesicular or vesicle-like form, including multi-molecular membranous structures or molten globular-like OMP compositions of one or more OMPs. Proteosomes may be prepared readily as described herein (see flowcharts of FIGS. 1A and 1B) and in the art (see, e.g., U.S. Pat. No. 5,726,292 or 5,985,284).

Liposaccharide refers to native (isolated from an organism or prepared synthetically with a native structure) or modified lipopolysaccharide or lipooligosaccharide (collectively, also referred to as "LPS") derived from Gram-negative bacteria. For example, a liposaccharide may be isolated from or synthetically produced to have the same carbohydrate structure as a liposaccharide from *Shigella flexneri* or *Plesiomonas shigelloides*, or other Gram-negative bacteria (including species from the genera *Alcaligenes, Bacteroides, Bordetella, Borrellia, Brucella, Campylobacter, Chlamydia, Citrobacter, Edwardsiella, Ehrlicha, Enterobacter, Escherichia, Francisella, Fusobacterium, Gardnerella, Hemophilus, Helicobacter, Klebsiella, Legionella, Leptospira* (including *Leptospira interrogans*), *Moraxella, Morganella, Neisseria, Pasteurella, Proteus, Providencia*, other *Plesiomonas, Porphyromonas* (including *Porphyromonas gingivalis*), *Prevotella, Pseudomonas, Rickettsia, Salmonella, Serratia*, other *Shigella, Spirillum, Veillonella, Vibrio*, or *Yersinia* species). The liposaccharide may be in a detoxified form (i.e., having the Lipid A or Lipid A-core removed) or may be in a form that has not been detoxified. In the instant disclosure, the liposaccharide need not be and preferably is not detoxified. For example, an LPS that contains multiple lipid A species such as *P. gingivalis* LPS may be used in the compositions described herein (see, e.g., Darveau et al., *Infect. Immun.* 72:5041-51 (2004)). The liposaccharide may be prepared, for example, as described in the flowchart of FIG. 2.

A Proteosome:LPS mixture or Protollin™ (also known as IVX or IVX908) described herein is a preparation of Proteosomes (Projuvant) admixed as described herein with at least one kind of liposaccharide to provide an OMP-LPS composition, which can be used as an immunostimulatory composition. Thus, the OMP-LPS adjuvant or Protollin includes an outer membrane protein preparation of Proteosomes prepared from Gram-negative bacteria, such as *Neisseria* sp., (e.g., *Neisseria meningitidis*), and a preparation of one or more liposaccharides. Protollin may also include one or more lipids, glycolipids, glycoproteins, small molecules, or the like. Protollin may be prepared, for example, as described in the flowchart of FIG. 3 (see also, e.g., U.S. Patent Application Publication No. 2003/0044425).

Projuvant is generally used in conjunction with antigens (natural, isolated antigens or modified antigens) that possess a hydrophobic moiety (also referred to as a hydrophobic foot). Protollin (with exogenously added LPS) can be associated with an antigen containing a hydrophobic foot or can be used with an antigen(s) that that is hydrophilic and does not contain a hydrophobic foot domain.

The present description generally provides immunostimulatory compositions that may include a Proteosome further formulated with a liposaccharide (Protollin). For example, a Protollin composition may be used to stimulate an antigen-independent, nonspecific protective immune response. In addition, the immunostimulatory composition may be used in combination with an immunogenic composition to initially promote (i.e., stimulate, elicit, or enhance) a nonspecific immune response and subsequently or concomitantly stimulate or elicit an adaptive immune response.

By way of background and not wishing to be bound by theory, the immune system is designed to detect and eliminate invading pathogens by discriminating between self and non-self. In mammals, the immune system is believed to have two branches; one is referred to as innate immunity and the other as adaptive immunity. The induction of innate immune responses may contribute significantly to overall immune defense (Medzhitov and Janeway, *Trends in Microbiol.* 8:452, 2000). Innate immunity may provide a nonspecific, first line of defense to limit infection immediately after exposure and also "network" with the adaptive immune response system by stimulating clonal responses (Hoffmann et al., *Science* 284: 1313, 1999). Thus, a nonspecific or innate immune response refers to an antigen-independent or antibody-independent immune response to pathogen-associated molecular patterns (PAMPs) (see, e.g., Medzhitov and Janeway, supra), such as the specific effects mediated by a mammalian innate immune system. For example, interaction of PAMPs with Toll-like receptors (TLRs) that are present on phagocytic antigen presenting cells (APCs) induces the release of pro-inflammatory cytokines (e.g., IFN-$\gamma$, TNF-$\alpha$, and IL-12) and the up-regulation of co-stimulatory molecules, which in turn can stimulate adaptive immunity.

An immunostimulatory composition as described herein may be any one or more of a protein, peptide, carbohydrate, lipid, nucleic acid, chemical, or other molecule, or composition thereof, that is capable of priming, potentiating, activating, stimulating, augmenting, boosting, amplifying, or enhancing an innate immune response. An immunostimulatory agent or composition can mitigate, alter, treat, or prevent (e.g., as a prophylactic agent) an infectious disease or condition. A potentiated or activated nonspecific immune response should be understood to be protective, even providing a broad-spectrum of protection in the absence of, or prior to, or concomitant with a specific antigen-dependent, antibody-dependent immune response. That is, an activated immune response can provide protection to a host from infection by a variety of microorganisms, including bacteria, viruses, parasites, or fungi. Representative examples of immunostimulatory agents or compositions as described herein in more detail, include, for example, adjuvants such as Proteosomes ("Projuvant") or Protollin (Proteosomes:liposacchamides).

Not wishing to be bound by theory, induction of an immune response mediated by the innate immune system involves Pathogen-Associated Molecular Patterns (PAMPs) that may exert non-antigen, yet specific effects. Interaction of PAMPs with Toll-Like Receptors (TLRs, at least ten of which are know and are referred to as TLR-1, TLR-2, etc.), which are present on the cell surface of phagocytic antigen presenting cells (APCs), for example, initiate an intracellular signal transduction pathway, which in turn induces the release of pro-inflammatory cytokines (e.g., IFN-γ, TNF-α, and IL-12) and upregulation of co-stimulatory molecules that in turn can stimulate adaptive immunity. Components of innate immunity recognize structures that are characteristic of microbial pathogens but that are not present on mammalian cells, which include unique nucleic acid structures (such as CpG DNA sequences), complex carbohydrates (such as LPS), as well as bacterial proteins, lipoproteins, and peptidoglycans. For example, Neisserial porin proteins (e.g., porin A, porin B, which are used to prepare Proteosomes) are recognized by TLR-2, and LPS from Gram-negative bacteria (which is a component of Protollin) is recognized by TLR-4. The Proteosome (Projuvant) and Protollin adjuvants may be used to stimulate an innate immune response. Moreover, through engagement of two components of Protollin (protein and liposaccharide) with TLRs on APCs, Protollin may initiate a chain of events that leads to the induction of both innate and adaptive immunity. In addition to Toll-like receptor activation of innate immunity, Protollin may activate other immune system components or immune functions. LPS is understood to be immunostimulatory through interactions with TLR-4 receptors present on the cell surface of certain immune system cells; hence, an immune response stimulated or elicited by Proteosomes (Projuvant) and an immune response stimulated or elicited by Protollin may be qualitatively or quantitatively distinguished in a statistically significant manner that correlates with the ratio of OMP to LPS in Protollin. The Protollin compositions described herein may also include an LPS that may interact with more than one Toll-like receptor such as the LPS obtained from *Porphyromonas gingivalis* (see, e.g., Darveau et al., *Infect. Immun.* 72:5041-51 (2004)).

An adaptive immune response (i.e., specific or acquired) includes resistance to an infectious agent or an antigen that is mediated by the immune system and that results from previous exposure to the infectious agent or antigen. For example, specific immunity can be a result of a naturally acquired (patent or latent) infection or from an intentional vaccination. In addition, specific immunity may be passively and transitorily acquired from the natural transfer of antibodies from another (e.g., maternally inherited), or from exogenous transfer of antibodies or immune cells by intentional inoculation (sometimes referred to as passive immunotherapy).

An immunogenic composition as described herein comprises one or more compounds, antigens, immunogens, or agents capable of priming, eliciting, potentiating, activating, stimulating, augmenting, boosting, amplifying, or enhancing an adaptive (specific) immune response, which may be cellular (T cell) or humoral (B cell), or a combination of a T cell and a B cell response. Preferably, the adaptive immune response will be protective. A representative example of an immunogen is a microbial antigen, such as one or more bacterial, viral, fungal, or parasitic proteins of interest.

An immunomodulatory composition as described herein may comprise Proteosomes or Protollin adjuvants and any one or more of a protein, peptide, chemical, or other molecule, or composition thereof, that is capable of altering (modifying, modulating, adjusting, regulating) (or increasing (potentiating) or decreasing (suppressing) in a statistically significant manner or in a clinically significant manner) one or more immune functions. An immunomodulatory agent or composition can mitigate, ameliorate, treat, or prevent (e.g., as a prophylactic agent) an undesired or abnormal inflammatory response. An immune function can include a cellular response with a particular pattern of cytokine production (e.g., Th1, Th2), a humoral response (e.g., antibody production), or a combination thereof, to a particular microbe or antigen. For example, if a subject previously exposed to an allergen (i.e., is sensitized) comes into contact with the allergen again, allergic asthma may develop due to a Th2 response characterized by an increased production of type 2 cytokines (IL-4, IL-5, IL-9, IL-13) secreted by CD4+ T lymphocytes. An immunomodulatory composition as described herein may alter the Th2 response by, for example, shifting the response toward a Th1 phenotype that is less damaging to the airway. That is, an altered (or modulated) immune response can provide protection to a host against infection by a variety of microorganisms (including bacteria, viruses, parasites, or fungi) or against inflammatory responses (e.g., allergy, asthma, nasal polyps) caused by antigens.

An allergic reaction as described herein refers to a local or general reaction in a subject following contact with a specific antigen (allergen) to which the subject had been previously exposed and sensitized. The immunologic interaction of endogenous or exogenous antigen with antibody or sensitized lymphocytes can give rise to inflammation and tissue damage—in other words, allergy is an immune reaction resulting in damage to self-tissues and cells, usually through inflammatory reactions. Extrinsic or allergic asthma (also referred to herein as reactive airway disease) is an inflammatory disease of the lungs characterized by a generally reversible airway obstruction. Features of allergic asthma include elevated concentrations of serum IgE, pulmonary eosinophilia, airway hyperresponsiveness, excessive airway mucus production, and airway remodeling marked by peribronchiolar collagen deposition and increases in airway smooth muscle mass. Other exemplary allergic reactions or inflammatory conditions include allergic alveolitis, allergic bronchopulmonary aspergillosis, allergic dermatitis, eczema, allergic conjunctivitis, allergic coryza, allergic vasculitis, rhinosinusitis, and allergic rhinitis.

Hyperresponsiveness relates to an abnormal response or condition in which a foreign agent elicits an exaggerated immune response. For example, allergic asthma may be a result of repeated exposure to airborne allergens that trigger detrimental immunological responses, such as persistent inflammation in the bronchial wall, which can result in structural and functional changes in the respiratory system. After allergen inhalation by sensitized subjects (i.e., those subjects that have already been exposed to the allergen), the immune response is dependent on CD4+ T lymphocytes that are skewed to a T helper (Th) 2 phenotype. Th2 cytokines, for example, IL-4, IL-5, IL-9, and IL-13 are important to asthma pathogenesis. For example, IL-4 drives the T helper response in favor of Th2, resulting in enhanced production of IgE; IL-5, which with granulocyte macrophage colony stimulating factor (GM-CSF) and IL-3, is important for the production of eosinophils; and IL-13, which is required for airway hyperresponsiveness and mucous metaplasia, which are downstream pathophysiological features that are closely linked with clinical asthma. All these cytokines, together with TGF-beta have been implicated in airway remodeling. While the role of eosinophils in the pathology of asthma is not entirely understood, the number of airway eosinophils is associated directly with disease severity (see, e.g., Lee et al., *Science* 305:1773 (2004); Humbles et al., *Science* 305:1776 (2004)). The resulting structural and morphometric changes (remodeling) include subepithelial fibrosis, goblet cell hyperplasia and metaplasia, which result in functional consequences such as loss of distensibility of asthmatic airways, bronchial hyperreactivity (even in the absence of the allergen), and an accelerated progressive decrease in forced expiratory volume at 1 second time intervals ($FEV_1$). The Th2 cytokines may also prime and activate eosinophils to release proinflammatory agents, lipid mediators, and other cytokines thought to contribute to the observed tissue damage, remodeling, and hyperresponsiveness.

Tolerance as used herein refers to the ability to endure or be less responsive to a stimulus, especially over of a period of continued exposure, such as to an allergen. For example, immunologic tolerance refers to a natural or artificially induced state of reduced or non-responsiveness to a specific antigen or allergen.

In the present description, any concentration range, percentage range, ratio range or other integer range is to be understood to include the value of any integer within the recited range and, when appropriate, fractions thereof (such as one tenth and one hundredth of an integer), unless otherwise indicated. As used herein, "about" or "comprising essentially of" mean±15%. The use of the alternative (e.g., "or") should be understood to mean one, both, or any combination thereof of the alternatives. As used herein, the use of an indefinite article, such as "a" or "an," should be understood to refer to the singular and the plural of a noun or noun phrase. In addition, it should be understood that the individual compositions, formulations, or compounds, or groups of compositions, formulations, or compounds, derived from the various components or combinations of the composition or sequences, structures, and substituents described herein, are disclosed by the present application to the same extent as if each composition or compound or group of compositions or compounds was set forth individually. Thus, selection of particular sequences, structures, or substituents is within the scope of the present invention.

In one embodiment, an immunomodulatory composition may comprise a Proteosome formulated with a liposaccharide, that is, Protollin. For example, a Protollin composition can be used to suppress or inhibit an undesired immune response or to induce or promote tolerance to an undesired immune challenge (e.g., shift a Th2 cytokine production phenotype to a Th1 phenotype). In addition, the immunomodulatory compositions described herein can be used in combination with an immunogenic composition to initially promote suppression of an undesired immune response, and subsequently or concomitantly, promote induction of tolerance. By way of background and not wishing to be bound by theory, T lymphocytes, in particular CD4+ T cells that produce Th2 cytokines and that have undergone an aberrant expansion, play an important role in the pathogenesis of asthma. In a murine model, the administration of agents such as IL-12 and IFN-γ or CpG oligodeoxynucleotides can inhibit Th2 cytokine production and stimulate Th1 lymphocytes and/or cytokines to prevent the development of antigen-induced airway hyperresponsiveness (AHR) and inflammation (see Lack et al., *J. Immunol.* 157:1432 (1996); Gavett et al., *J. Exp. Med.* 182:1527-36 (1995); Kline et al., *J. Immunol.* 160:2555 (1998)).

In certain embodiments, the immunostimulatory compositions described herein are useful for eliciting a nonspecific (or innate) immune response. Such an immunostimulatory composition may provide a nonspecific protective response that prevents or treats a microbial infection in a host or subject. The immunostimulatory composition described herein may also be used to stimulate an innate (nonspecific) immune response that potentiates or enhances an adaptive immune response elicited by subsequently administered vaccine, for example, an immunogenic composition comprising Protollin formulated with a microbial antigen, such as F1-V plague antigen, Protective Antigen from *Bacillus anthracis*, or a bacterial antigen from *Chlamydia trachomatis*, enteropathogenic *E. coli*, or another pathogenic bacteria.

In certain embodiments, immunostimulatory and immunogenic compositions may be administered simultaneously to elicit an innate immune response while at the same time potentiating or priming an adaptive immune response. In certain other embodiments, immunomodulatory and immunogenic compositions may be administered simultaneously to elicit an altered immune response while at the same time potentiating or priming tolerance. Alternatively, short-term use of an immunostimulatory or immunomodulatory composition as described herein may be used without subsequent or simultaneous treatment with an immunogenic composition. Nonspecific protection or an altered immune response (without subsequent or simultaneous immunogenic composition treatment) may last from about 1 day to 3 months or longer. For example, animals remained protected from *Chlamydia* challenge at least 11 weeks after treatment with Proteosome-LPS (Protollin) (see Example 15).

In other embodiments, the immunomodulatory compositions described herein are useful for altering an inflammatory immune response. As set forth herein, the current compositions may be used to alter an inflammatory immune response (e.g., cause a shift from a Th2 to a Th1 phenotype) that may potentiate or enhance the development of tolerance to a specific antigen.

An immunostimulatory or immunomodulatory composition comprises an adjuvant, preferably a Proteosome or a Proteosome:LPS adjuvant. Proteosomes can be comprised of outer membrane proteins (OMPs or porins) from *Neisseria* species, but can also be derived from other Gram-negative bacteria (see, e.g., Lowell et al., *J. Exp. Med.* 167:658, 1988; Lowell et al., *Science* 240:800, 1988; Lynch et al., *Biophys. J.* 45:104, 1984; U.S. Pat. Nos. 5,726,292; 4,707,543), or a combination of *Neisseria* OMPs and OMPs from at least one other Gram-negative bacteria. By way of background and not wishing to be bound by theory, mixing of Proteosomes with a protein (e.g., a microbial antigen) provides a composition comprising non-covalent association, interaction, or coordination between the microbial antigen and Proteosomes, which association or coordination forms when the detergent used to solubilize the Proteosomes is selectively removed or reduced, for example, by dialysis or diafiltration.

Proteosomes may be used as an adjuvant (i.e., a component of an immunostimulatory or immunomodulatory composition) and/or may be used as an antigen delivery composition (i.e., an immunogenic composition). In one embodiment, an immunogenic composition comprises one or more microbial antigens (i.e., bacterial, parasitic, fungal, or viral antigens or immunogens, or variants and fragments thereof) and an adjuvant, wherein the adjuvant comprises Projuvant (i.e., Proteosome) or Protollin (i.e., Proteosome:LPS). A preferred microbial antigen is one that stimulates or elicits an immune response (either humor or cell-mediated) that protects (prevents a microbial infection, reduces the microbial load, kills the microorganism or prevents its propagation) the host or subject.

In certain embodiments, the immunostimulatory or immunomodulatory composition may be a Proteosome further formulated with a liposaccharide. That is, the Proteosome adjuvant (Projuvant) may be prepared to include an additional (e.g., exogenous or endogenous) immunostimulatory or immunomodulatory molecule, such as LPS. Liposaccharride can be prepared synthetically, isolated from a biological source (e.g., non-detoxified), chemically modified (e.g., detoxified or otherwise chemically modified by adding, deleting, or changing substituents), or any combination thereof. For example, the Projuvant may be admixed as described herein with liposaccharide to provide an OMP:LPS adjuvant (i.e., Protollin). These two components of Protollin may be formulated at specific initial ratios (see flowchart of FIG. 3) to optimize their interaction, resulting in stable association and formulation of the components for use in an immunostimulatory or immunomodulatory composition. The process for making Protollin generally involves mixing the components in a selected detergent solution (e.g., EMPIGEN® BB(n-Dodecyl-N,N-dimethylglycine), TRITON® X-100 (octyl phenol ethoxylate), or Mega-10(n-Decanoyl-N-methylglucamide)) or other detergent (e.g., octoglucoside). Complex formation of the OMP and LPS components occurs while reducing the amount of detergent to a predetermined, preferred concentration, by dialysis or by diafiltration/ultrafiltration methodologies. The duration of dialysis can be adjusted to retain varying amounts of detergent in the vaccine formulation including, for example, concentrations from 250, 500, 750, 1000 ppm, or more, or even lower amounts (e.g., 50 ppm). Mixing, co-precipitation, or lyophilization of the two components may also be used to effect an adequate and stable association or formulation. In certain embodiments, the Protollin may be formulated to comprise LPS from one bacteria or may be formulated to comprise two or more liposaccharides obtained from different bacteria. For example, one Protollin formulation may include liposaccharide from *Escherichia* and *Shigella*, or from *Chlamydia* and *Yersinia*, or *Phorphyromonas* and *Shigella*, or from *Neisseria, Escherichia, Yersinia*, and *Shigella*, and so on. A Protollin formulation may be optimized with one or a plurality of as many different liposaccharides as is necessary or desired.

Protollin compositions described herein may contain liposaccharide derived from any Gram-negative bacterial species, which may be the same Gram-negative bacterial species that is the source of Proteosomes, or may be a different bacterial species. In one embodiment, the final liposaccharide content by weight as a percentage of the total Proteosome protein may be in a range from about 0.1% to about 10%, from about 0.5% to about 5%, from about 1% to about 500%, or in a range from about 10% to about 100%, about 5% to about 20% or from about 10% to about 50%, or in a range from about 20% to about 200%, or in a range from about 30% to about 150% or from about 50% to 150%. In a preferred embodiment, the immunostimulatory composition comprises a Proteosome component prepared from *Neisseria meningitidis* and the liposaccharide prepared from *Shigella flexneri* or *Plesiomonas shigelloides*, such that the final liposaccharide content is between 50% to 150% of the total Proteosome protein by weight. In another embodiment, Proteosomes are prepared with endogenous lipooligosaccharide (LOS) content from *Neisseria* ranging from about 0.5% up to about 5% of total OMP. In another embodiment Proteosomes are provided that comprise endogenous liposaccharide (i.e., from the same bacteria as the Proteosomes) in a range from about 12% to about 25%, and in a preferred embodiment between about 15% and about 20% of total OMP. Alternatively, mutant bacteria that can no longer produce LPS (e.g., a *Neisseria* LPS—minus strain) can be used to prepare Projuvant such that the OMP:LPS mixture has 0% endogenous LPS. Accordingly, Protollin may have exogenous LPS, endogenous LPS, or a combination thereof, wherein the exogenous and endogenous LPS may be present in equal amounts or at different ratios.

The present invention is also directed generally to the use of microbial antigens in combination with an immunostimulatory or immunomodulatory composition to generate an immunogenic composition. The antigens are preferably from clinically relevant microorganisms, such as bacteria, including pathogenic bacteria; viruses (e.g., Influenza, Measles, Coronavirus); parasites (e.g., Trypanosome, *Plasmodium, Leishmania*); fungi (e.g., *Aspergillus, Candida, Coccidioides, Cryptococcus*); and the like. For example, the antigen may be from bacteria, particularly pathogenic bacteria, such as the causative agent of anthrax (*Bacillus anthracis*), plague (*Yersinia pestis*), stomach cancer (*Helicobacter pylori*), sexually transmitted diseases (*Chlamydia trachomatis* or *Neisseria gonorrhea*), and the like. Other representative examples include antigens from certain viruses, such as influenza virus (es), Norwalk virus, smallpox virus, West Nile virus, SARS virus, respiratory syncytial virus, measles virus, and the like. Exemplary fungi include *Candida albicans* or *Aspergillus* spp., and exemplary parasites include the causative agents of trypanosomiasis, *leishmania*, pneumonic plague, and lyme disease (*Borrellia burgdorferi*).

As described herein, the antigens can be prepared recombinantly, synthetically, isolated from a biological source, recombinantly or chemically modified, and any combination thereof. A biological source includes but is not limited to a biological sample from a host or subject (e.g., tissue, blood, serum, plasma, lung lavage, nasal wash), bacterial cell culture, or tissue cell culture. A "sample" as used herein refers to a biological sample and may be provided by obtaining a blood sample, biopsy specimen, tissue explant, organ culture, or any other tissue or cell preparation from a subject or a biological source. A sample may further refer to a tissue or cell preparation in which the morphological integrity or physical state has been disrupted, for example, by dissection, dissociation, solubilization, fractionation, homogenization, biochemical or chemical extraction, pulverization, lyophilization, sonication or any other means for processing a sample derived from a subject or biological source.

A microbial antigen or fragment thereof can be prepared from a variety of biological sources, such as tissues of an infected subject or cultured cell lines. Primary isolation may be from, for example, peripheral blood cells or from respiratory secretions or excretions. Preferably, the isolated microbes are propagated or cultured on appropriate culture media that are known to skilled artisans, in primary cell cultures, or on established cell lines known in the art as required for a particular microbe. In certain embodiments, the antigens or fragments thereof are isolated from intact microbial particles. As used herein, the term "isolated" or "derived from" means that the material is removed from its original or natural environment. For example, a naturally occurring nucleic acid molecule or polypeptide present in a living animal or cell or virus is not isolated, but the same nucleic acid molecule or polypeptide is isolated when separated from some or all of the co-existing materials in the natural system. An isolated nucleic acid molecule or a nucleic acid molecule that is removed from its natural environment includes a vector such as a recombinant expression vector, which comprises a nucleic acid molecule that encodes a microbial antigen. In other embodiments, peptides or polypeptides, such as antigens or variants and fragments thereof, may be either partially purified or purified to homogeneity.

Also provided herein are methods for producing synthetic microbial antigens, including fusion proteins that comprise a microbial antigen, variant, or fragment thereof. A peptide or polypeptide component of an immunogenic composition may be synthesized by standard chemical methods, including synthesis by an automated procedure. In general, immunogenic polypeptides or peptides are synthesized based on the standard solid-phase Fmoc protection strategy with HATU as the coupling agent. The immunogenic peptide can be cleaved from the solid-phase resin with trifluoroacetic acid containing appropriate scavengers, which also deprotects side chain functional groups. Crude immunogenic peptide may be further purified using preparative reverse phase chromatography. Other purification methods, such as partition chromatography, gel filtration, gel electrophoresis, or ion-exchange chromatography may be used. Other synthesis techniques known in the art may be employed to produce similar immunogenic peptides, such as the tBoc protection strategy, use of different coupling reagents, and the like. In addition, any naturally or non-naturally occurring amino acid or derivative thereof may be used, including D- or L-amino acids and combinations thereof.

As described herein, the microbial antigens or fragments thereof of the invention may be recombinant, wherein a recombinant nucleic acid expression construct comprises a polynucleotide that encodes the antigen and is operatively linked to an expression control sequence (e.g., promoter, enhancer). Recombinant polynucleotide expression constructs may be prepared according to methods known to persons skilled in the molecular biology art. Cloning and expression vectors for use with prokaryotic and eukaryotic hosts are described, for example, in Sambrook et al., *Molecular Cloning: A Laboratory Manual*, Third Edition, Cold Spring Harbor, N.Y., (2001), and may include plasmids, cosmids, shuttle vectors, viral vectors, and vectors comprising a chromosomal origin of replication as disclosed therein. Recombinant expression constructs also comprise expression control sequences (regulatory sequences) that allow expression of a polypeptide of interest in a host cell, including one or more promoter sequences (e.g., lac, tac, trc, ara, trp, λ phage, T7 phage, T5 phage promoter, CMV, immediate early, HSV thymidine kinase, early and late SV40, LTRs from retrovirus, and mouse metallothionein-I), enhancer sequences, operator sequences (e.g., lacO), and the like.

Generally, recombinant expression vectors will include origins of replication and selectable markers permitting transformation of the host cell, and a promoter derived from a highly-expressed gene to direct transcription of a downstream structural sequence. The heterologous structural sequence is assembled in appropriate phase with translation initiation and termination sequences. In preferred embodiments the constructs are included in compositions that are administered in vivo. Such vectors and constructs include chromosomal; non-chromosomal; and synthetic DNA sequences, e.g., derivatives of SV40; bacterial plasmids; phage DNA; yeast plasmids; vectors derived from combinations of plasmids and phage DNA; viral DNA, such as vaccinia, adenovirus, fowl pox virus, and pseudorabies; or replication deficient retroviruses as described below. However, any other vector may be used for preparation of a recombinant expression construct, and in preferred embodiments such a vector will be replicable and viable in the host (subject).

The recombinant expression vector may be introduced into a host cell by transformation, transfection, or transduction according to methods known to those skilled in the molecular biology art. The host cells (such as a eukaryotic or prokaryotic host cells or insect cells) may be cultured to permit expression of the encoded microbial antigen, thus producing a recombinant protein antigen (or immunogen), or fragment thereof. The antigens may be further fused or conjugated to another amino acid sequence, which sequence may be a hydrophobic anchor or foot (anch) to facilitate or otherwise enhance non-covalent association with Projuvant or Protollin. A fragment of a microbial antigen polypeptide may comprise any portion of such a polypeptide that has at least one epitope capable of eliciting a protective immune response (cellular or humoral) against a microbial infection. Immunogenic polypeptides may also be arranged or combined and linked in a linear form, and each immunogen may or may not be reiterated, wherein the reiteration may occur once or multiple times. In addition, a plurality of different immunogenic polypeptides (e.g., protein variants, or fragments thereof) can be selected and mixed or combined into a cocktail composition to provide a multivalent vaccine for use in eliciting a protective immune response.

A variant of an antigen, including a microbial antigen or allergen as described herein, or a fragment of an antigen or variant, include molecules that are structurally similar and functionally similar. A variant or fragment of antigen or allergen, is functionally similar to the antigen or allergen if the variant or fragment is capable of eliciting an immune response at least comparable according to one or more characteristics or parameters of an immune response to that elicited by the antigen or allergen, which may be determined using methods, including animal models and in vitro assays, described herein and practiced in the art. For example, a comparable immune response may be determined by quantitative and/or qualitative determination of cytokine production, antibody production (including class and/or isotype), and protection as determined in an animal model. A comparable immune response of an antigen variant or fragment to the antigen may be indicated by statistical analysis of a particular measure (such as cytokine production or immunoglobulin production) and maybe within 5%, 10%, 15%, or 20% or 25% of the measurement. A functionally similar variant or fragment also is capable of binding to an antibody that specifically binds to the antigen or allergen.

Such variants include naturally-occurring polymorphisms or allelic variants, microbial strain variants, as well as synthetic polypeptides (or the polynucleotides encoding the variant polypeptides) that contain conservative amino acid substitutions of the amino acid sequences. A variety of criteria known to those skilled in the art indicate whether amino acids at a particular position in a peptide or polypeptide are similar. For example, a similar amino acid or a conservative amino acid substitution is one in which an amino acid residue is replaced with an amino acid residue having a similar side chain, which include amino acids with basic side chains (e.g., lysine, arginine, histidine); acidic side chains (e.g., aspartic acid, glutamic acid); uncharged polar side chains (e.g., glycine, asparagine, glutamine, serine, threonine, tyrosine, cysteine, histidine); nonpolar side chains (e.g., alanine, valine, leucine, isoleucine, proline, phenylalanine, methionine, tryptophan); beta-branched side chains (e.g., threonine, valine, isoleucine), and aromatic side chains (e.g., tyrosine, phenylalanine, tryptophan). Proline, which is considered more difficult to classify, shares properties with amino acids that have aliphatic side chains (e.g., Leu, Val, Ile, and Ala). In certain circumstances, substitution of glutamine for glutamic acid or asparagine for aspartic acid may be considered a similar substitution in that glutamine and asparagine are amide derivatives of glutamic acid and aspartic acid, respectively.

Variant polynucleotides and their encoded polypeptide products can be identified by determining whether the polynucleotides hybridize with a nucleic acid molecule having the nucleotide sequence of under highly stringent or moderately stringent conditions. As an alternative, variant polynucleotides and the encoded polypeptides can be identified by sequence comparison. As used herein, two amino acid sequences have "100% amino acid sequence identity" if the amino acid residues of the two amino acid sequences are the same when aligned for maximal correspondence. Similarly, two nucleotide sequences have "100% nucleotide sequence identity" if the nucleotide residues of the two nucleotide sequences are the same when aligned for maximal correspondence. Sequence comparisons can be performed using any standard software program, such as BLAST, tBLAST, pBLAST, or MegAlign. Still others include those provided in the Lasergene bioinformatics computing suite, which is produced by DNASTAR® (Madison, Wis.). References for algorithms such as ALIGN or BLAST may be found in, for example, Altschul, *J. Mol. Biol.* 219:555-565, 1991; or Henikoff and Henikoff, *Proc. Natl. Acad. Sci. USA* 89:10915-10919, 1992. BLAST is available at the NCBI website. Other methods for comparing multiple nucleotide or amino acid sequences by determining optimal alignment are well known to those of skill in the art (see, e.g., Peruski and Peruski, *The Internet and the New Biology: Tools for Genomic and Molecular Research* (ASM Press, Inc. 1997); Wu et al. (eds.), "Information Superhighway and Computer Databases of Nucleic Acids and Proteins," in Methods in Gene Biotechnology, pages 123-151 (CRC Press, Inc. 1997); and Bishop (ed.), Guide to Human Genome Computing, 2nd Edition, Academic Press, Inc., 1998). An antigen or allergen and a variant thereof should have at least a 50% amino acid sequence identity to and preferably, greater than 60%, 65%, 70%, 75%, 80%, 85%, 90%, or 95% identity.

Variants may be prepared readily using mutagenesis techniques known and practiced in the art. For example, site-directed mutagenesis (e.g., Kramer et al. (*Nucleic Acids Res.* 12, 9441, (1984)); the Anglian Biotechnology Ltd handbook; Kunkel *Proc. Natl. Acad. Sci. USA* 82:488-92 (1985); Kunkel et al., *Methods in Enzymol.* 154:367-82 (1987)) and random mutagenesis techniques, such as alanine scanning mutagenesis, error prone polymerase chain reaction mutagenesis, and oligonucleotide-directed mutagenesis are well known and used extensively in the art (see, e.g., Sambrook et al., *Molecular Cloning: A Laboratory Manual,* $3^{nd}$ ed., Cold Spring Harbor Laboratory Press, NY (2001)).

Methods for preparing the immunostimulatory compositions, immunomodulatory compositions, and immunogenic compositions are described herein and are known in art (see, e.g., U.S. Patent Application Publications Nos. 2001/0053368 and 2003/0044425). The antigen(s) and adjuvant are formulated at specific initial ratios (weight:weight) to optimize interaction (or cooperation) between the components resulting in non-covalent association (or nonspecific juxtaposition) of a significant portion of the two components with each other. For example, a mixture of at least one antigen with a Proteosome (Projuvant) or Protollin is prepared in the presence of detergent, and reduction of the concentration of the detergent or removal of the detergent from the mixture by diafiltration/ultrafiltration leads to association (interaction or coordination) of the antigen(s) with the adjuvant (see FIG. 3). The ratio of Proteosome or Protollin to antigen after the mixture has been dialyzed, diafiltered, or ultrafiltered may be the same or may be altered (increased or decreased) from the initial ratio. In certain embodiments, the initial or post-dialysis/diafiltration/ultrafiltration Proteosome or Protollin (the weight of Protollin equals the combined weights of the Proteosomes and liposaccharide) to antigen ratio (wt/wt) in an immunogenic composition mixture ranges from about 1:1 to about 4:1. The ratio may range from 1:1 to about 8:1 or higher. In certain other embodiments, the Proteosome or Protollin to antigen ratio (wt/wt) in the mixture ranges from about 1:1 to about 1:500, or in a range of about 1:1 to about 1:200 or about 1:2 to about 1:200, or in a range of about 1:2 to about 1:100, or in a range of about 1:5 to about 1:50, or in a range of about 1:2 to about 1:20. The detergent-based solutions of the two components may contain the same detergent or different detergents, and more than one detergent may be present in the mixture subjected to ultrafiltration/diafiltration. Suitable detergents include TRITON®, EMPIGEN® BB, and Mega-10. Other detergents can also be used (e.g., octoglucoside). The detergents serve to solubilize the components used to prepare the composition. The use of a mixture of detergents may be particularly advantageous. The detergent(s) are removed or the concentration is reduced by diafiltration/ultrafiltration prior to final formulation.

Also contemplated are methods for treating or preventing a microbial infection, by administering an immunostimulatory composition described herein for eliciting a nonspecific protective immune response. In another embodiment, a method is provided for treating or preventing a microbial infection by administering an immunostimulatory composition for eliciting an innate immune response and administering an immunogenic composition for eliciting an adaptive immune response. Also contemplated are methods for altering an inflammatory response, or treating or preventing an allergic reaction, using immunomodulatory and/or immunogenic compositions of this disclosure. An immunostimulatory composition, immunomodulatory composition, or immunogenic composition may further include a pharmaceutically acceptable vehicle, carrier, diluent, and/or excipient, in addition to one or more microbial antigens (or immunogens) or fragment or fusion thereof and, optionally, other components. For example, pharmaceutically acceptable carriers or other components suitable for use with immunostimulatory compositions, immunomodulatory compositions, or immunogenic compositions include a thickening agent, a buffering agent, a solvent, a humectant, a preservative, a chelating agent, an additional adjuvant, and the like, and combinations thereof.

In addition, the pharmaceutical compositions as described herein may further include a diluent such as water or phosphate buffered saline (PBS). In certain embodiments, the diluent is PBS with a final phosphate concentration range from about 0.1 mM to about 1 M, from about 0.5 mM to about 500 mM, from about 1 mM to about 50 mM, or from about 2.5 mM to about 10 mM; and the final salt concentration ranges from about 100 mM to about 200 mM or from about 125 mM to about 175 mM. In another embodiment, the final PBS concentration is about 5 mM phosphate and about 150 mM salt (such as NaCl). In certain embodiments, any of the aforementioned immunostimulatory, immunomodulatory, or immunogenic compositions further comprising a diluent will be sterile.

The compositions can be sterilized either by preparing them under an aseptic environment or by terminal sterilization using methods available in the art. Many pharmaceuticals are manufactured to be sterile and this criterion is defined by USP XXII <1211>. The term "USP" refers to U.S. Pharmacopeia (Rockville, Md.). Sterilization may be accomplished by a number of means accepted in the industry and listed in USP XXII <1211>, including gas sterilization, ionizing radiation, or filtration. Sterilization may be maintained by what is termed aseptic processing, defined also in USP XXII <1211>. Acceptable gases used for gas sterilization include ethylene oxide. Acceptable radiation types used for ionizing radiation methods include gamma, for instance from a cobalt 60 source and electron beam. A typical dose of gamma radiation is 2.5 MRad. When appropriate, filtration may be accomplished using a filter with suitable pore size, for example, 0.22 μm and of a suitable material, for instance TEFLON®. The preparation of Proteosomes or Protollin results in particles small enough that an immunogenic compositions can be filtered through a 0.8 μm filter, a 0.45 μm filter, or a 0.2 μm filter.

Thus, in certain embodiments the immunostimulatory, immunomodulatory, and/or immunogenic compositions of this invention can be filter sterilized. This is highly advantageous to eliminate any complications due to the presence of contaminants.

In one embodiment, a method is provided for eliciting a nonspecific protective immune response, comprising administering to a subject (or patient) in need thereof an amount of an immunostimulatory composition and under conditions sufficient to elicit, induce, or stimulate an immune response such that the amount of the immunostimulatory composition is therapeutically effective. The conditions under which an immune response is elicited in a subject include a variety of parameters and criteria described herein and understood by persons having skill in the medical art, and include but are not limited to the time of dosing, number of doses, route of administration, and the like. A nonspecific protective immune response as described herein includes an innate immune response that is not a specific antigen-dependent or antibody-dependent response (that is, does not involve clonal expansion of T cells and/or B cells) and may be elicited by any one of numerous antigens, immunogens, or microorganisms. The immunostimulatory composition comprises Proteosomes and liposaccharide (Protollin), either one of which or both may elicit a nonspecific protective response. When the immunostimulatory composition is used to elicit a nonspecific immune response or an innate immune response for treating or preventing a microbial infection, such as a bacterial infection or a viral infection, the immunostimulatory composition comprising Protollin may not contain a liposaccharide from the genus of bacteria that is the causative agent of an infection to be treated or prevented. That is, the Protollin need not have components or PAMPs from the organism that is causing an infection or that may cause an infection. By way of example, an immunostimulatory composition comprising Proteosomes obtained from *Neisseria meningitidis* and LPS obtained from *Shigella flexneri* may be used to stimulate an innate response in a subject that provides protection, that is, treats or prevents infection caused by a virus, such as an influenza virus, or by a bacteria such as *Yersinia pestis, Bacillus anthracis*, or *Chlamydia trachomatis*. Accordingly, the immunostimulatory compositions described herein may be useful for treating or preventing infections that can be caused by one of numerous different strains of a virus, such as different strains of influenza virus, or that may be caused by one of numerous different strains, serotypes, or immunotypes of a bacterial species.

The Proteosomes and liposaccharide of Protollin may be obtained from the same or different bacterial genera or species. The Proteosomes may be obtained from a Gram-negative bacteria such as a *Neisseria* species and the liposaccharide may be from another Gram-negative bacteria such as from *Shigella, Chlamydia, Plesiomonas, Porphyromonas*, or *E. coli*. In one embodiment, a method is provided for potentiating a specific immune response, comprising administering to a subject in need thereof a therapeutically effective amount of an immunostimulatory composition, wherein the immunostimulatory composition comprises Proteosomes and liposaccharide.

In another embodiment, a method is provided for treating or preventing a microbial infection, wherein after the immunostimulatory composition has been administered, an immunogenic composition is administered to the subject (or patient) in need thereof in an amount sufficient and under conditions such that the administration of both compositions effectively elicits a specific immune response. In a certain embodiment, the immunogenic composition comprises Proteosomes, liposaccharide, and an antigen such as a microbial antigen (bacterial, viral, parasitic, or fungal antigen). The immunogenic composition may comprise Proteosomes that are obtained from the same or different sources of the Proteosomes of the immunostimulatory composition, such as different Gram-negative bacteria genus and/or species. Similarly, an LPS component of the immunogenic composition and the immunostimulatory composition may be from the same or different bacteria. The immunogenic composition may comprise one antigen that is a microbial antigen, or may comprise 2, 3, 4, 5, 6, 7, or 8-10 microbial antigens. When at least two microbial antigens are contained in the immunogenic composition, the antigens may be obtained from, associated with, or known to be originally derived from the same microorganism or from different microorganisms. Alternatively, the immunogenic composition may comprise at least one antigen without Proteosomes and/or LPS, or the immunogenic composition may comprise at least one antigen and an adjuvant such as alum. The antigen may be isolated (purified) or partially isolated (or purified), or may be delivered as a live, infectious microorganism or in an attenuated form. In certain embodiments, the microbial antigen is a viral split antigen as described herein, which may contain all components of a virus. Any one of the immunogenic compositions described herein may be administered to a subject once or more than once (multiple times) after administration of an immunostimulatory composition.

The immunostimulatory and immunogenic compositions described herein may be administered to a subject (or patient) as a prophylactic treatment to prevent a microbial infection prior to exposure to the microorganism that causes the infection. A prophylactic treatment also includes administration of an immunostimulatory composition alone or followed by an immunogenic composition to prevent a microbial infection in a subject who is known to have been exposed, who is at risk for exposure, or who has likely been exposed to the causative microbial agent. An immunostimulatory composition alone or followed by an immunogenic composition may also be used to treat a subject who may have a subclinical infection (i.e., not detected according to appropriate clinical criteria) or may have a clinical infection that is or can be diagnosed clinically according to criteria known to those skilled in the art, including symptomatology, clinical chemistry, and microbiological analyses.

The ratio (wt:wt) (initial ratio or post-removal of detergent) of Proteosomes or Protollin (combined weight of Proteosomes and liposaccharide) to antigen of the immunogenic composition may range from about 4:1 to about 1:4, and may be at least 4:1 or at least 2:1. The ratio of Proteosomes (or Protollin) to antigen may be greater than 1:1, greater than 2:1, greater than 3:1 and greater than 4:1. The ratio can be as high as 8:1 or higher. Alternatively, the ratio of Proteosome (or Protollin) to antigen in the mixture is 1:1, 1:2, 1:3, 1:4, or 1:8. The Proteosome or Protollin to antigen ratio in the mixture may range from about 1:1 to about 1:500, or from about 1:1 to about 1:200 or from about 1:2 to about 1:200, or from about 1:2 to about 1:100, or from about 1:5 to about 1:50, or from about 1:2 to about 1:20.

As described herein, different sources of LPS may be used in Protollin preparations. The use of a particular source or type of LPS may depend upon the adjuvant properties of the Proteosome:LPS composition when administered by a particular route, such as intranasally, the type of immune response induced (innate and/or adaptive), the quantity or quality of cytokine production, the capability of a particular LPS type to interact with a particular host cell, the solubility properties of the LPS (i.e., the length of a O-polysaccharide chain may influence solubility of the Proteosome/LPS mixture during preparation of Protollin), as well as production methods (e.g., yield, biohazard containment requirements). Protollin may be prepared containing *S. flexneri* 2a LPS, LPS from different strains of *E. coli*, or LPS from other Gram-negative bacteria and characterized according to methods described herein and known in the art.

The ratio of Proteosome (OMPs) to LPS in a Protollin preparation may be determined by methods described herein and known in the art for determining the amount of LPS or OMPs that is free (i.e., uncomplexed) versus bound (i.e., in a OMP:LPS complex) such as capillary electrophoresis. LPS content of Protollin may be determined by a KDO assay, NMR, polyacrylamide gel electrophoresis and silver staining of the gel, and other methods practiced by a person having skill in the art. The OMP content of Protollin may be determined by any number of assays that measure protein content including but not limited to mass spectrometry methods such as LC-MS, reverse phase high pressure liquid chromatography (RP-HPLC), sodium dodecyl sulfate polyacrylamide gel electrophoresis (SDS-PAGE) (including protein staining such as with Coomassie blue or immunoblotting), N-terminal sequencing, amino acid analysis, Lowry or BCA protein assays, and MALDI-TOFMS. Residual LPS in a Proteosome preparation may also be determined by the LPS assays, such as KDO. Nucleic acids remaining in the OMP, LPS, or Protollin preparation by methods known in the art to detect nucleic acids, and the presence of detergent may be determined by HPLC.

In certain embodiments, the antigen is bacterial, for example, an anthrax Protective Antigen (PA) (see, e.g., Lindler et al., *Infect. Immun.* 66:5731-42 (1998)) or a plague antigen. The plague antigen used in the immunogenic composition may comprise an F1 antigen or a V antigen from *Yersinia pestis*, or an F1-V antigen fusion protein antigen, or a combination thereof (see, e.g., Anderson et al., *Infect. Immun.* 64:4580-85 (1996)). In other embodiments, the antigen is viral, such as a viral split antigen preparation (for example, a influenza split antigen (see U.S. Patent Application 2004/0156867) or measles split antigen). A viral split antigen is an antigen preparation that is separated or isolated from a virus particle. A viral split antigen generally comprises more than one single viral antigen and may comprise all viral antigens although not in the same proportion or quantity as may be found in an intact virus particle. A split antigen may be prepared according to procedures that enrich one or more viral antigens, that is, the proportion of a particular antigen in a split antigen preparation may be greater than in intact virus. For example, a influenza split antigen may be enriched for influenza Hemagglutinin antigen.

Other exemplary microbial antigens include, but are not limited to, lipopolysaccharide, structural polypeptides or glycoproteins, flagellar or cilia proteins, toxins, virulence factors, viral core proteins, and viral envelope proteins and glycoproteins. In certain embodiments, isolated LPS may be an antigen, for example, LPS isolated from *P. gingivalis*, which may be formulated with Proteosomes for use in stimulating an immune response to *P. gingivalis* for treating or preventing gum disease, periodontal disease, tooth decay, and the like.

In certain embodiments, the immunogenic composition is administered about between one to about ten days, one to fourteen days, or one to twenty-one days after the immunostimulatory composition, preferably at least three days after administration of the immunostimulatory composition, and elicits an adaptive immune response. Such a method for treating or preventing a microbial infection may comprise administering to a patient in need thereof an immunostimulatory composition having Proteosomes and liposaccharide in an amount and under conditions sufficient to elicit an innate or nonspecific protective immune response; and administering to a patient in need thereof a immunogenic composition having Proteosomes, liposaccharide, and an antigen, or at least two microbial antigens, in an amount and under conditions sufficient to elicit an adaptive immune response.

As described herein an innate immune response comprises host recognition of invariant molecular constituents of infectious microorganisms that represent molecular structures (PAMPs) shared by large groups of microorganisms, for example, lipopolysaccharides with the conserved lipid A structure that are found in Gram-negative bacteria or peptidoglycan common to Gram-positive bacteria. Such antigens are recognized as non-self antigens by host receptors, thus the host elicits a nonspecific immune response to destroy the non-self target. The capability of immunostimulatory compositions described herein, such as Protollin alone to stimulate innate immunity against aerosol challenge with various pathogens, such as *Chlamydia trachomatis* or *Bacillus anthracia*, may be determined according to methods described herein and known in the art, including animal models. Animals, such as rodents (mice, rat, rabbits) can be treated with Protollin prepared as described herein and then challenged with a pathogenic microorganism. Morbidity and mortality can then be determined. Animals may receive one, two, three, or more treatments with an immunostimulatory composition to determine whether and for how long the innate immune response can be maintained or re-stimulated. The capability of an immunostimulatory composition in the presence and absence of an immunogenic composition to elicit, enhance, or stimulate the innate immune response may also be examined by the ability of the compositions to upregulate MHC class I and II and B7.2 on peripheral blood B lymphocytes, dendritic, cells, and mucosal epithelial cells from wildtype mice and from TLR-2, TLR-4, and MyD88 knockout transgenic animals.

In one embodiment, the disclosure relates to a method for altering an inflammatory immune response, comprising administering to a subject (or patient) in need thereof a therapeutically effective amount of an immunomodulatory composition, wherein the immunomodulatory composition comprises Proteosomes and liposaccharide, such that the inflammatory immune response is altered. In another embodiment, a method for treating or preventing an allergic reaction comprises administering to a subject (or patient) in need thereof an amount of an immunomodulatory composition, wherein the immunomodulatory composition comprises Proteosomes and liposaccharide, such that the allergic reaction is treated, attenuated, ameliorated, or prevented. In certain embodiments when treating or preventing an allergic reaction, such as an allergen-induced reaction, the immunomodulatory composition comprising Protollin will not contain a specific allergen, or if the allergen is a bacteria, will not contain liposaccharide from the genus of bacteria that is the allergen. That is, the Protollin need not have components that are causing directly or indirectly an allergic reaction. In some embodiments, the Proteosomes and liposaccharide are obtained from the same or different bacterial genera or species. Preferably, the Proteosomes are from *Neisseria* species and the liposaccharide is obtained from *Shigella, Chlamydia, Plesiomonas, Porphyromonas*, or *E. coli*.

In another embodiment, after the immunomodulatory composition has been administered, a subject suffering from or at risk for an allergic reaction is given an amount of an immunogenic composition comprising Proteosomes, liposaccharide, and an allergen (e.g., microbial antigen or pollen) such that the allergic reaction is treated, prevented, diminished, attenuated, or ameliorated. In certain embodiments, the ratio (wt:wt) (initial and/or post-detergent removal) of Proteosomes (or Protollin, which would include the combined weight of the Proteosomes and liposaccharide) to allergen (or antigen) of the immunogenic composition ranges from about 4:1 to about 1:4, preferably the ratio at least 4:1 or at least 2:1. In other embodiments, the ratio of Proteosomes (or Protollin) to antigen of the immunogenic composition ranges from about 1:1 to about 1:500, preferably the ratio is at least 1:20, at least 1:50, or at least 1:100. In certain other embodiments, the Proteosome or Protollin to allergen (or antigen) ratio in the mixture ranges from about 1:1 to about 1:500, or in a range of about 1:1 to about 1:200 or about 1:2 to about 1:200, or in a range of about 1:2 to about 1:100, or in a range of about 1:5 to about 1:50, or in a range of about 1:2 to about 1:20. In certain embodiments, the allergen is at least one of an inhaled particle, pollen (e.g., microspores of weeds, trees, grasses, etc.), vapor, gas, food, beverage (or a component thereof), drug, toxin, microbial antigen (e.g., viral, viral split antigen, bacterial, parasitic, fungal, and combinations thereof), dander, animal-derived compounds, dust (e.g., dust having LPS or dust mite feces), polypeptide, carbohydrate, nucleic acid, or any other agent capable of eliciting an allergic reaction. The immunogenic composition may be administered about one to about ten days, one to twenty days, or one to thirty days after the immunomodulatory composition, or about three days after, such that an inflammatory immune response or an allergic reaction is altered.

The immunostimulatory, immunogenic, and/or immunomodulatory compositions described herein may induce specific anti-antigen immune responses or immunomodulatory effects, including one or more of the following. A specific humoral response may be elicited or stimulated that results in production of antigen specific antibodies, which may include any class of immunoglobulin, including IgG, IgA, IgM, and/or IgE, and isotypes of the classes. For example, the presence of specific IgG, IgA (particularly in mucosal secretions), and IgE in serum, nasal wash, lung lavage, or other tissues may be determined by any of a variety of immunoassays described herein and known in the art, including but not limited to, ELISA, immunoblot, radioimmunoassay, immunohistochemistry, fluorescence activated cell sorting (FACS), Ochterlony, and the like. For detection of antigen or microorganism specific antibodies in an immunoassay, the biological sample may be permitted to interact with or contact an antigen that is purified, isolated, partially isolated, or a fragment thereof, or to interact with or contact a microorganism, which may be fixed (such as with ethanol or formaldehyde) or unfixed or non-denatured. Mucosal secretions include those collected from the respiratory tract, including the nasopharynx and lungs. Functional assays may also be performed, such as the ability of an antigen-specific antibody to neutralize a toxin (such as a macrophage protection assay), facilitate phagocytosis or opsonization of a microorganism, or to prevent entry of a microorganism into a host cell, or to prevent entry, fusion, or propagation of a microorganism such as a virus in a host cell. Such methods are described herein and are routinely practiced by skilled artisans.

Cell-mediated immunity (CMI) or immune response in a subject who has received one or more of the immune compositions described herein may also be determined using methods described herein and known in the art. A cell mediated immune response includes determining whether an immune response has shifted from a predominantly Th2 response to a balanced or mixed Th1 and Th2 response (due to an increase in Th1 response or concomitant increase in Th1 and decrease in Th2 response), or to a predominantly Th1 response. Similarly, a shift from a Th1 response to a balanced or mixed Th1/Th2 response or an increased or predominant Th2 response may be determined. For example, levels of Th1 cytokines, such as IFN-γ, IL-2, and TNF-β, and Type 2 cytokines, such as IL-4, IL-5, IL-9, IL-10, and IL-13, may be determined according to methods described herein and practiced in the art, including ELISA, ELISPOT, and flow cytometry (to measure intracellular cytokines). Type 1 responses are predictive of induction of other CMI-associated responses, such as development of cytotoxic T cells (CTLs), which are indicative of Th1 immunity. Immune cell proliferation and clonal expansion resulting from an antigen-specific elicitation or stimulation of an immune response may be determined by isolating lymphocytes, such as spleen cells or cells from lymph nodes, stimulating the cells with antigen, and measuring cytokine production, cell proliferation and/or cell viability, such as by incorporation of tritiated thymidine or non-radioactive assays, such as MTT assays and the like.

In any of these aforementioned methods, the immunomodulatory compositions, immunostimulatory compositions, and the immunogenic compositions may further comprise a pharmaceutically acceptable carrier, excipient, or diluent as described herein. A pharmaceutical composition may be a sterile aqueous or non-aqueous solution, suspension or emulsion, which additionally comprises a physiologically acceptable carrier (i.e., a non-toxic material that does not interfere with the activity of the active ingredient). Such compositions may be in the form of a solid, liquid or gas (aerosol). Alternatively, compositions of the present invention may be formulated as a lyophilizate. Pharmaceutical compositions within the scope of the present invention may also contain other components, which may be biologically active or inactive. Such components include, but are not limited to, buffers (e.g., neutral buffered saline or phosphate buffered saline), diluents, stabilizers, dyes, flavoring agents, and suspending agents and/or preservatives.

Any suitable carrier known to those of ordinary skill in the art may be employed in the pharmaceutical compositions of the present invention. Carriers for therapeutic use are well known, and are described, for example, in *Remingtons Pharmaceutical Sciences*, Mack Publishing Co. (A. R. Gennaro ed. (1985)). In general, the type of carrier is selected based on the mode of administration. Pharmaceutical compositions may be formulated for any appropriate manner of administration, including, for example, topical, oral, nasal, intrathecal, rectal, vaginal, sublingual or parenteral administration, including subcutaneous, intravenous, intramuscular, intrasternal, intracavernous, intrameatal or intraurethral injection or infusion. For parenteral administration, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, kaolin, glycerin, starch dextrins, sodium alginate, carboxymethylcellulose, ethyl cellulose, glucose, sucrose and/or magnesium carbonate, may be employed.

A pharmaceutical composition (e.g., for oral administration or delivery by injection) may be in the form of a liquid (e.g., an elixir, syrup, solution, emulsion or suspension). A liquid pharmaceutical composition may include, for example, one or more of the following: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

As used herein, the terms treat and ameliorate refer to the therapeutic administration of a desired composition or compound, in an amount and under conditions sufficient to treat, inhibit, attenuate, ameliorate, reduce, prevent or alter at least one aspect or marker of a disease, in a statistically significant manner or in a clinically significant manner. A therapeutically effective amount of an immunomodulatory composition, immunostimulatory composition, or immunogenic composition is the amount of the composition that treats at least one aspect or marker of a disease as described herein.

The compositions described herein that comprise one or more immunomodulatory composition, immunostimulatory composition, and immunogenic composition may be in any form that allows the composition to be administered to a subject, such as a human or animal. For example, compositions may be prepared and administered as a liquid solution or prepared as a solid form (e.g., lyophilized), which may be administered in solid form, or resuspended in a solution in conjunction with administration. The compositions may be formulated to allow the active ingredients contained therein to be bioavailable upon administration to a subject or patient or may be bioavailable via slow release. Compositions that will be administered to a subject or patient take the form of one or more dosage units, for example, a drop may be a single dosage unit, and a container of one or more compositions may hold a plurality of dosage units. In certain preferred embodiments, any of the aforementioned pharmaceutical compositions comprising an immunostimulatory composition, or an immunostimulatory composition with an immunogenic composition that comprises at least one antigen (or immunogen) or a cocktail of immunogens, or an immunomodulatory composition are in a container, preferably in a sterile container.

The design of a particular protocol for administration, including dosage levels and timing of dosing are determined by optimizing such procedures using routine methods well known to those having ordinary skill in the art. Pharmaceutical compositions may be administered in a manner appropriate to the disease to be treated (or prevented). An appropriate dose and a suitable duration and frequency of administration will be determined by such factors as the condition of the patient, the type and severity of the patient's disease, the particular form of the active ingredient and the method of administration. In general, an appropriate dose and treatment regimen provides the compositions in an amount sufficient (therapeutically effective amount) to provide therapeutic and/or prophylactic benefit (e.g., an improved clinical outcome, such as more frequent complete or partial eradication of the infection, or longer disease-free and/or overall survival, or a lessening of symptom severity). For prophylactic use, a dose should be sufficient to prevent, delay the onset of, or diminish the severity of a disease associated with the particular infectious microorganism.

In one embodiment, any one of the immunomodulatory composition, immunostimulatory composition or immunogenic composition is administered nasally. Other routes of administration include enteral, parenteral, transdermal/transmucosal, sublingual, nasal, and by inhalation. The term enteral, as used herein, is a route of administration in which the immunogenic composition is absorbed through the gastrointestinal tract or oral mucosa, including oral, rectal, and sublingual. The term parenteral, as used herein, describes administration routes that bypass the gastrointestinal tract, including intraarterial, intradermal, intramuscular, intranasal, intraocular, intraperitoneal, intravenous, subcutaneous, submucosal, and intravaginal injection or infusion techniques. The term transdermal/transmucosal, as used herein, is a route of administration in which any of the compositions described herein is administered through or by way of the skin, including topical. The terms "nasal" and "inhalation" encompass techniques of administration in which an immunogenic composition is introduced into the pulmonary tree, including intrapulmonary or transpulmonary. Preferably, the compositions of the present invention are administered nasally.

Furthermore, the immunogenic compositions of this invention can be used to enhance immunity, or as a follow on immunization or tolerance induction, when given together with another vaccine, such as a live attenuated vaccine, or a non-live, subunit vaccine. For example, compositions comprising one or more antigen or fragment or fusion thereof with Projuvant or Protollin may be used as a priming or boosting immunization (by mucosal or parenteral routes) prior to or subsequent to administering a different vaccine.

All U.S. patents, U.S. patent application publications, U.S. patent applications, foreign patents, foreign patent applications and non-patent publications referred to in this specification and/or listed in the Application Data Sheet, are incorporated herein by reference, in their entirety. The invention having been described, the following examples are intended to illustrate, and not limit, the invention.

EXAMPLES

Example 1

Preparation of Proteosomes

Immunogens (e.g., microbial antigens or allergens) may be formulated with Proteosomes to form an immunogenic composition of the instant invention capable of eliciting a protective immune response or tolerance in a human or animal subject. Proteosomes are useful as an adjuvant and are comprised of outer membrane proteins purified from Gram-negative bacteria. Methods for preparing Proteosomes are described in, for example, Mallett et al. *Infect. Immun.* 63:2382, 1995; U.S. Pat. No. 6,476,201 B1; U.S. Patent Application Publication No. 2001/0053368; and U.S. Patent Application Publication No. 2003/0044425. Briefly, a paste of phenol-killed Group B type 2 *Neisseria meningitidis* was extracted with a solution of 6% EMPIGEN® BB (EBB) (Albright and Wilson, Whithaven, Cumbria, UK) in 1 M calcium chloride. The extract was precipitated with ethanol, solubilized in 1% EBB-Tris/EDTA-saline, and then precipitated with ammonium sulfate. The precipitated Proteosomes were re-solubilized in 1% EBB buffer, diafiltered, and stored in a 0.1% EBB buffer at -70° C.

Figure 1B:
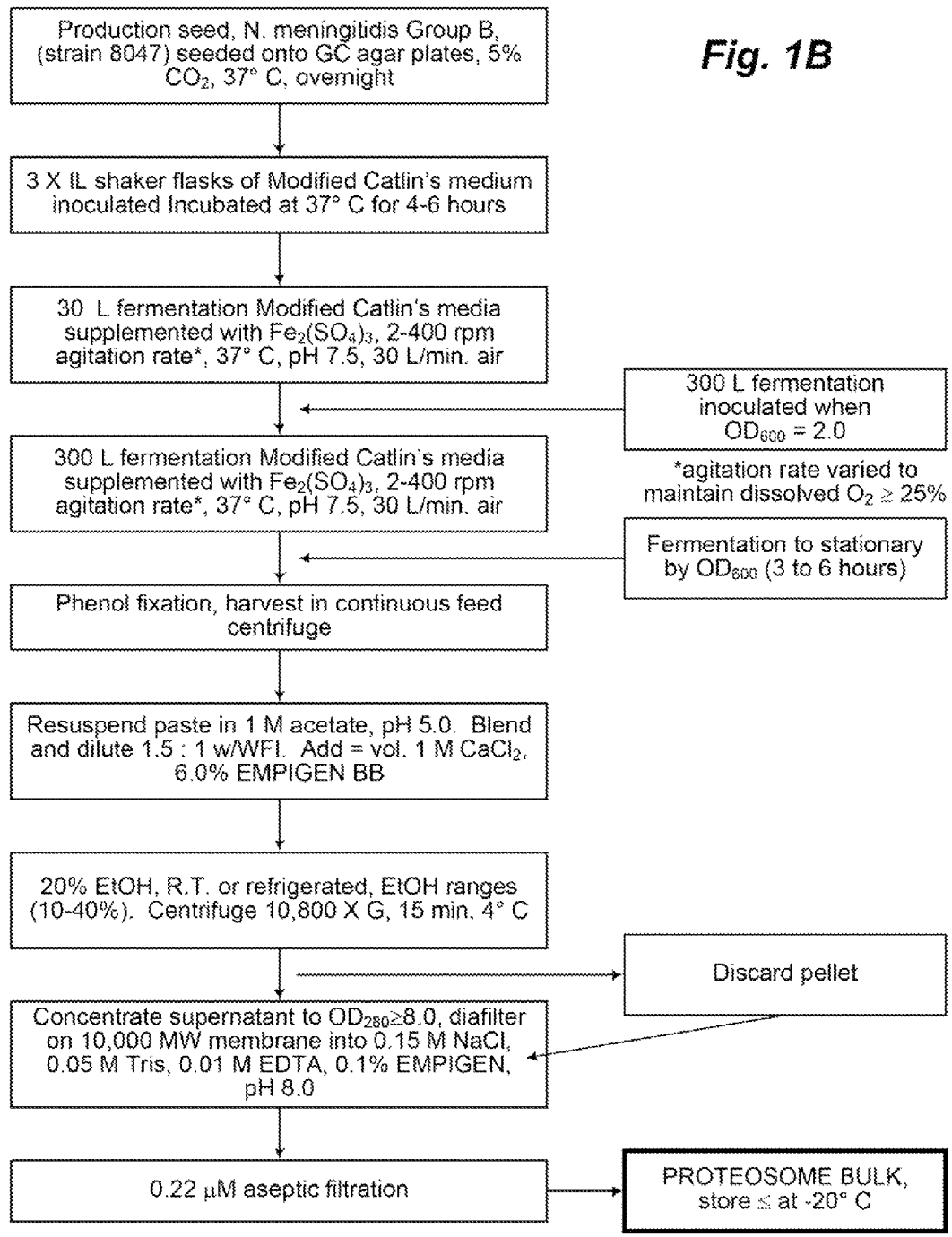

A flow chart of this process, which resulted in Proteosomes having a liposaccharide content of between about 0.5% and about 5%, is shown in Flowchart 1A (FIG. 1A). Proteosomes may also be prepared by omitting the ammonium sulfate precipitation step to shorten the process. The resultant Proteosomes having a liposaccharide content of between about 12% and about 25%, and may, depending upon the materials, be between about 15% and about 20%, as shown in Flowchart 1B (FIG. 1B). A person having ordinary skill in the art could adjust methods for preparing formulations comprising Projuvant or OMP-LPS (Protollin) compositions as described herein to optimize particular characteristics of the vaccine components.

Example 2

Preparation of Liposaccharides

The example in Flowchart 2 (FIG. 2) shows the process for the isolation and purification of LPS (e.g., non-detoxified) from *S. flexneri* or *P. shigelloides*. This process can similarly be used for preparing LPS from one or more other Gramnegative bacteria, including *Shigella, Plesiomonas, Porphyromonas, Escherichia*, and *Salmonella* species. Following growth of bacteria by fermentation in 300 L, the bacteria were sedimented and the cell paste was re-hydrated with 3 ml 0.9 M NaCl, 0.005 M EDTA, and 10 mg lysozyme per gram of bacterial paste. Lysozyme digestion was allowed to proceed for 1 hour at room temperature. Then 50 U/ml BENZONASE® (DNase) (Merck Chemicals) in 0.025 M $MgCl_2$ was added, and DNase digestion was allowed to proceed at room temperature for 30 minutes. The suspension was then cracked by passage through a microfluidizer at 14,000 to 19,000 psi. Fresh DNase (50 U/ml) was added, and digestion of the suspension was allowed to proceed for an additional 30 minutes at room temperature. The digested cell suspension was heated to 68° C. in a water bath. An equal volume of 90% phenol (also heated to 68° C.) was then added, and the mixture was incubated with shaking at 68° C. for 30 minutes. The mixture was centrifuged at 4° C. to separate the aqueous and organic phases. The aqueous phase was harvested and the organic phase was re-extracted with WFI (water for injection) at 68° C. for 30 minutes. The mixture was centrifuged at 4° C., the second aqueous phase was harvested, and the two harvested aqueous phases were combined. To precipitate nucleic acids, 20% ethanol with 10 mM $CaCl_2$ was added to the pooled aqueous phases. The mixture was stirred at 4° C. overnight. Precipitated nucleic acids were then sedimented by centrifugation at 10,000 x g for 30 minutes. The supernatant was harvested, concentrated, and diafiltered using a 30,000 MW hollow fiber cartridge into 0.15 M NaCl, 0.05 M Tris, 0.01 M EDTA, and 0.1% EMPIGENE® BB, pH 8.0 (TEEN buffer). The LPS was then sterile-filtered using a 0.22 µm MILLIPAK® 60 filter unit, aliquoted into sterile storage containers, and frozen at −80° C. Stability studies indicated that bulk LPS has a storage life of at least 2 years.

Example 3

Preparation and Characterization of Proteosome:Liposaccharide Adjuvant

Figure 3:
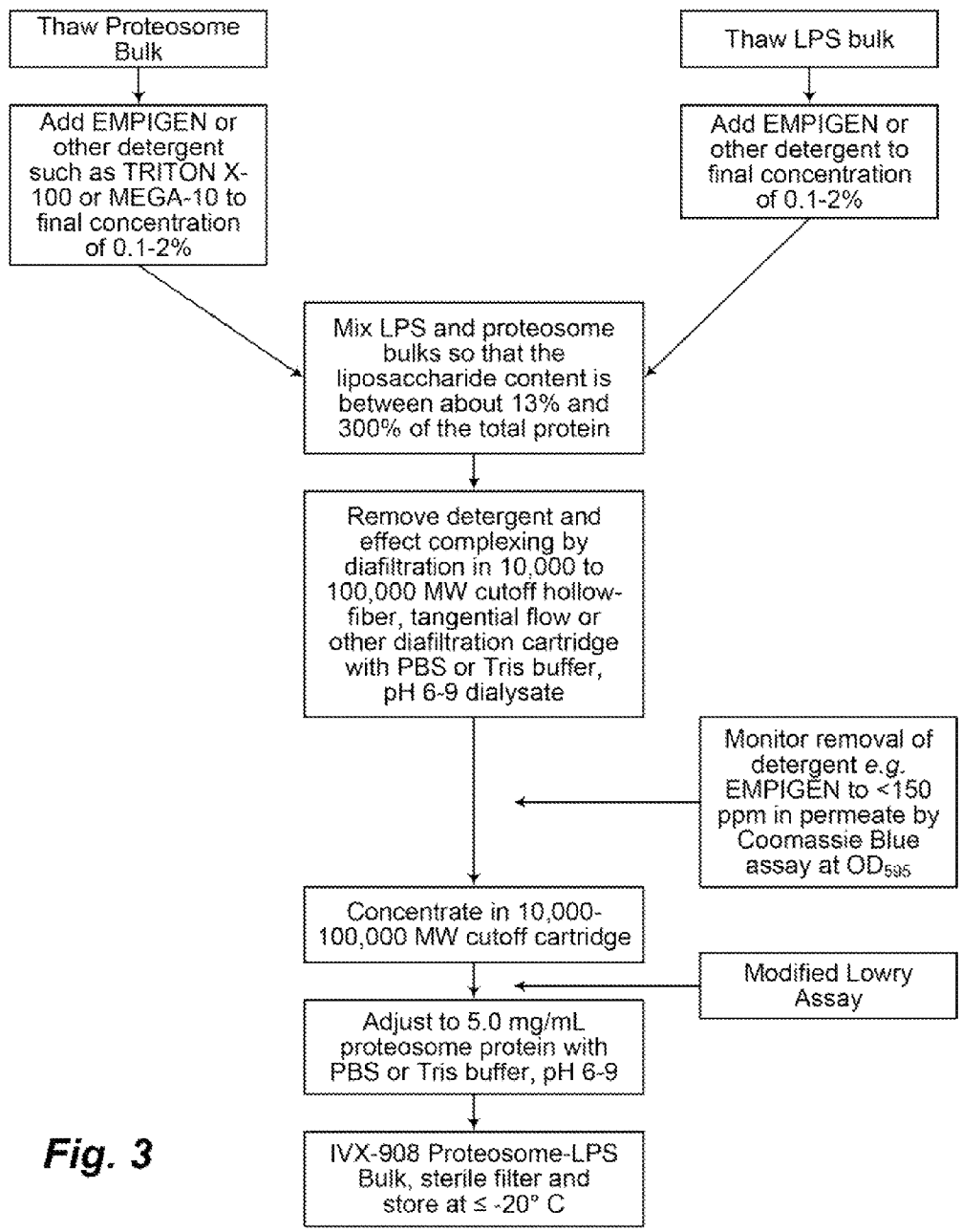
FIG. 3 presents a scheme for the manufacture of IVX-908 Proteosome-LPS adjuvant, which is also called Protollin™ (Flow Chart 3).

A Proteosome adjuvant formulation was prepared by admixing Proteosomes with LPS (Protollin). The LPS can be derived from any of a number of one or more Gram negative bacteria, such as *Shigella, Plesiomonas, Escherichia*, or *Salmonella* species (see Example 2), which is mixed with the Proteosomes of Example 1, as described in Flowchart 3 (FIG. 3). Briefly, Proteosomes and LPS were thawed overnight at 4° C. and the detergent concentration was adjusted to 1% EMPIGEN® BB in TEEN buffer. The Proteosomes and LPS were mixed for 15 minutes at room temperature in quantities that resulted in a final wt/wt ratio of between about 10:1 and about 1:3 of Proteosome:LPS. The Proteosome:LPS mixture was diafiltered on an appropriately sized (e.g., Size 9) 10,000 MWCO (molecular weight cut-off) hollow fiber cartridge into TNS buffer (0.05 M Tris, 150 mM NaCl pH 8.0). The diafiltration was stopped when EMPIGEN® content in the permeate was <50 ppm, which was determined by EMPIGEN® Turbidity Assay or by a Bradford Reagent Assay manufacturer's and standard protocols. The bulk adjuvant (referred to herein as OMP-LPS) was concentrated and adjusted to 5 mg/ml protein. The protein content was determined by a standard Lowry assay. The adjuvant was sterile-filtered using a 0.22 µm MILLIPAK 20 filter unit. The bulk adjuvant was aliquoted into sterile storage containers and frozen.

The OMP-LPS adjuvant was tested for (1) EMPIGEN® (400 ppm) using reverse-phase HPLC; (2) protein content by a Lowry assay; and (3) LPS content by measurement in a 2-keto-3-deoxyoctonate (KDO) assay. The OMP-LPS composition was further characterized for particle size distribution as determined by quantitative number weighted analysis using a particle seizer (e.g., Brookhaven Instruments model 90 plus or similar machine) (10-100 nm). However, the particle size for the complex may increase or modulate with varying (e.g., higher) Proteosome to LPS ratio. These Proteosome:LPS complexes have been termed Protollin. Stability data indicated that this formulation is stable for longer than 2 years.

Protollin has been prepared using other sources of LPS. Two Protollin preparations were made using LPS from two different strains of *E. coli* and had similar adjuvant activity. Protollin is also prepared using *N. meningiditis* LPS. *N. meningitis* LPS is frequently called LOS denoting lipooligosaccharide because the O-side chain of *N. meningiditis* liposaccharide is shorter than that of other Gram-negative bacteria such as *E. coli* and *Shigella*. Production of Protollin with *N. meningiditis* LPS (Protollin-Nm) is different from all other versions of Protollin. During the production of *N. meningiditis* Proteosome OMPs, LPS is removed by ammonium sulfate precipitation techniques so that Proteosome particles have less than 2.5% *N. meningiditis* LPS. If the LPS is not removed at this step, the resultant Proteosome particles have about 20-25% LPS, resulting in an OMP:LPS ratio ranging from about 5:1 to about 4:1. Thus, Protollin-Nm is produced in a single step, thereby eliminating further purification of the Proteosome particles. An aliquot of each Protollin is retained for use in, for example, a spin-down assay to verify Proteosome OMP complexing with LPS. Each of these versions of Protollin is tested in mice for adjuvant activity after formulation with rPA (recombinant Protective Antigen).

Example 4

Immunization with Protollin Formulated with Plague Antigen F1-V

This Example describes the ability of Proteosome:LPS (Protollin) compositions formulated with plague antigen (F1-V) to elicit an immune response capable of protecting against a lethal challenge with *Yersinia pestis*. The F1-V immune response was assessed by immunizing groups of 20 6-8 week old female Swiss-Webster mice (Charles River, St-Constant, Quebec) on days 0 and 21. Freshly thawed aliquots of Protollin and F1-V fusion protein (U.S. Army Medical Research Institute of Infectious Disease) solutions were mixed less than 16 hours prior to immunization. For nasal administration, mice were first lightly anesthetized by isoflurane inhalation. Twenty-five microliters of vaccine or appropriate control samples (Protollin alone or F1-V alone) were applied to the nares (12.5 µl per nostril) of each mouse. In parallel, a group of mice were immunized intramuscularly (i.m.) by injection into hind limbs with 25 µl F1-V adsorbed to 500 mg of ALHYDROGEL®. Control i.m. injections were also performed. Thirty-five and 55 days thereafter, 10 mice from each group were euthanized by asphyxiation with $CO_2$ and exsanguination. Serum, nasal wash, and lung lavage samples were obtained and stored at −80° C. Spleens were processed for in vitro restimulation and assessment of released cytokines The remaining 10 mice from each group were challenged on day 35 or 55 by inhalation of 170-250 $LD_{50}$ of aerosolized *Y. pestis* (Colorado 92 strain) to assess protection. Mice were monitored for 28 days after challenge for determination of morbidity and mortality.

Figure 4A:
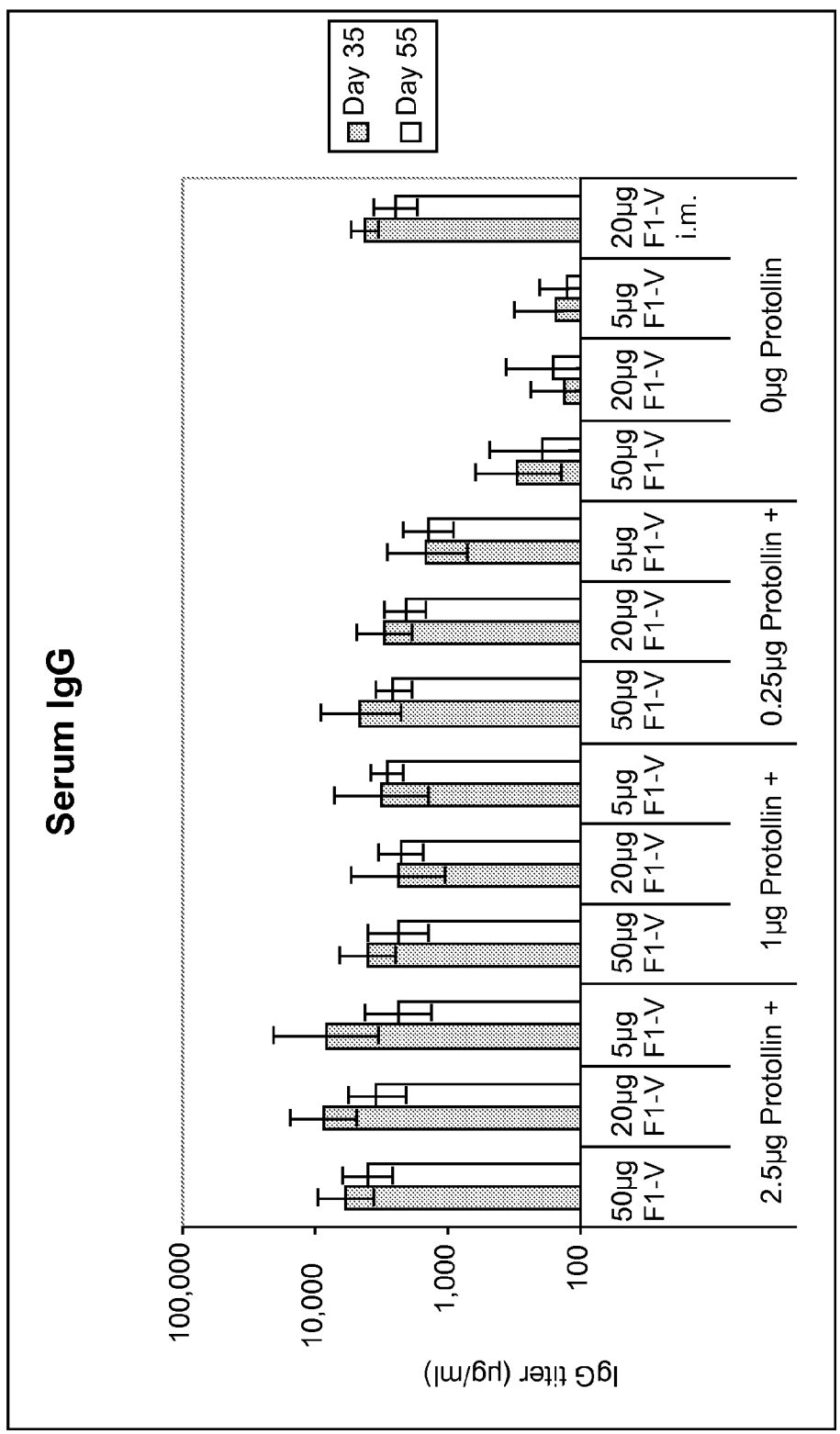
FIGS. 4A-4C show serum IgG, lung IgA, and lung IgG titers, respectively, from mice immunized twice intranasally with 50 µg, 20 µg, or 5 µg of F1-V with Protollin (2.5, 1, or 0.25 µg) or without Protollin, or injected intramuscularly with 20 µg F1-V adsorbed onto alum (ALHYDROGEL®). Half the mice were euthanized on day 35 post-primary immunization, and the remainder were euthanized on day 55. Titers are expressed as the geometric mean of specific antibody concentrations (µg/ml for serum IgG; ng/ml for lung IgA and lung IgG); 95% confidence limits are shown.
Figure 4B:
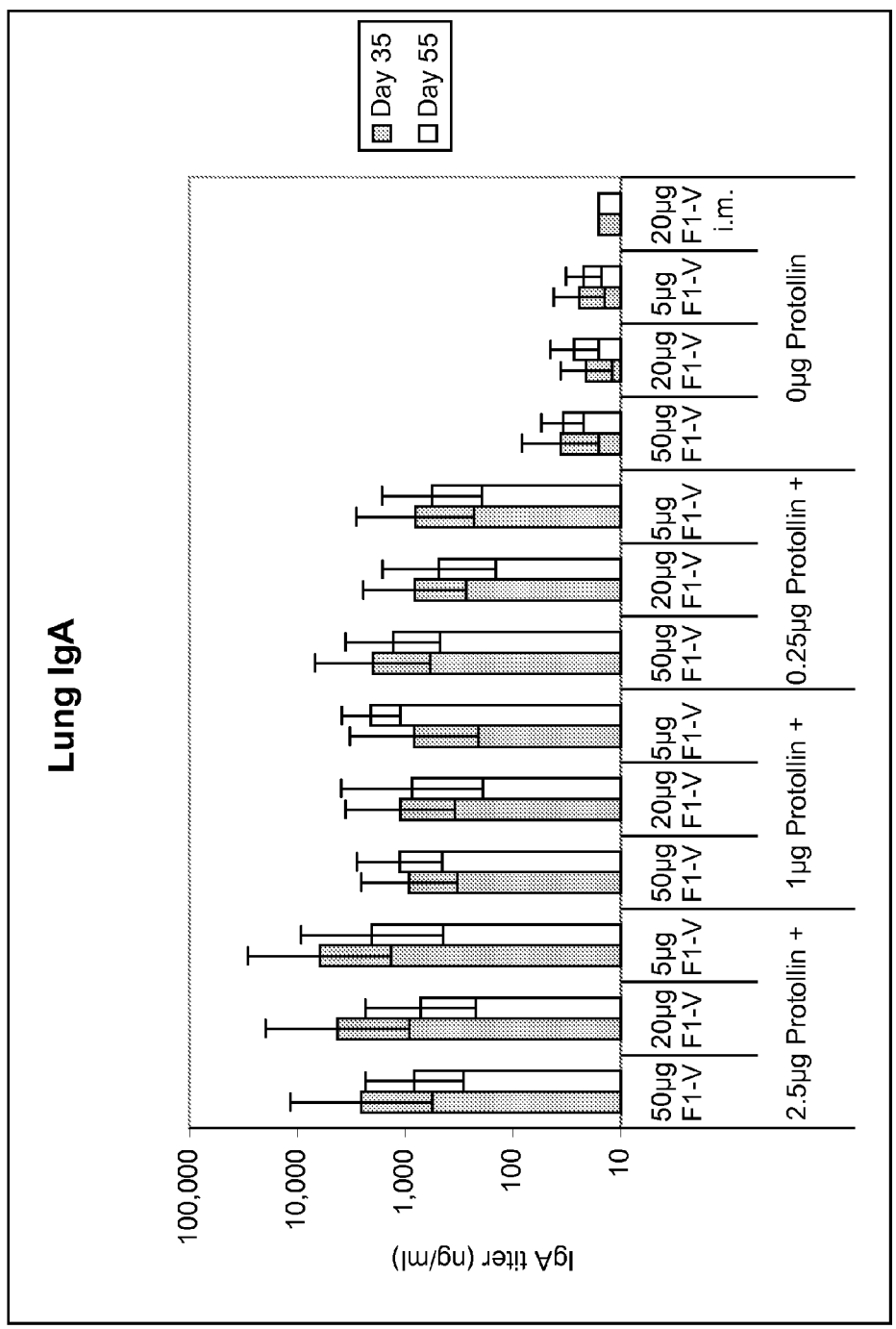
Figure 4C:
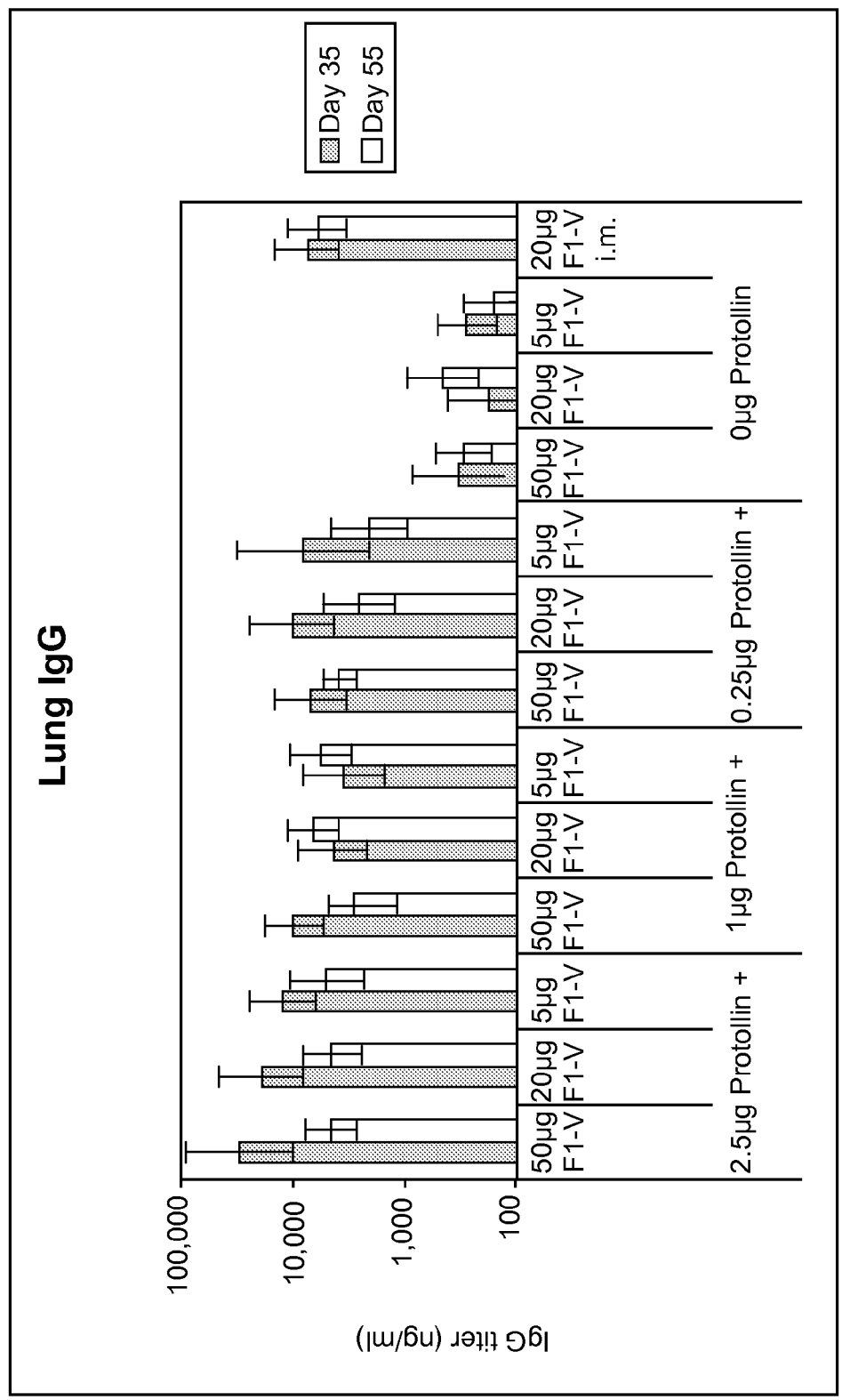

Antibodies present in serum and lung lavage fluid samples were obtained from mice immunized intranasally with two doses of F1-V antigen formulated with Protollin and compared with samples from mice immunized intranasally with F1-V alone or with mice immunized intramuscularly with ALHYDROGE®-adsorbed F1-V. The results are shown in FIG. 4. All combinations of Protollin and F1-V were highly immunogenic and elicited F1-V specific serum IgG titers of between 1 and 9 mg/ml (FIG. 4A). On both sampling days a trend towards lower titers elicited by the lower F1-V and/or Protollin concentrations was observed, but no significant differences were measured in the specific IgG titers elicited by any combination of F1-V and Protollin concentrations or those elicited by intramuscular injection of 20 μg of F1-V adsorbed onto ALHYDROGEL (P >0.05). All specific serum IgG titers in mice immunized with F1-V formulated vaccines were significantly higher than titers measured in animals that received nasal administration of unformulated F1-V controls (P <0.001). No F1-V specific antibodies were detected in serum from control mice.

The levels of specific anti-F1-V, anti-F1, and anti-V antibodies present in lung lavage samples were determined by ELISA performed according to standard methodologies using F1-V fusion protein, F1 polypeptide, and V polypeptide as antigens (U.S. Army Medical Research Institute of Infectious Disease). IgG and IgA antibody titers were determined on individual samples by ELISA as previously described (Plante et al., *Vaccine* 20:218 (2001)). Briefly, ELISA plates were coated with F1-V, F1, or V at pre-determined concentrations. Bound antibody is detected with HRP-conjugated anti-mouse IgG or IgA. Data are expressed as geometric means of antibody concentrations in individual mouse samples, and the significance of the data is assessed by ANOVA analysis using Tukey-Kramer pair-wise comparisons. All groups of mice immunized intranasally with F1-V antigen plus Protollin had high titers of F1-V specific lung IgA as shown in FIG. 4B, confirming that immunization by mucosal (e.g., intranasal) routes efficiently elicits mucosal antibodies. ANOVA analysis indicated no significant differences in the IgA titers among groups of mice that were immunized with different combination of F1-V plus Protollin. Animals that received unformulated F1-V alone nasally had barely detectable IgA levels. Secretory IgA was not detected in samples from mice injected i.m. with ALHYDROGEL-adsorbed F1-V.

Sera and lung lavage fluid from all mice immunized with a 20 μg dose of F1-V antigen were examined in an ELISA to determine if antibodies in sera specifically bound to F1 or V or both components. In all instances and at both sampling times, serum IgG and lung lavage fluid IgA antibodies that recognized F1 and V portions of the F1-V antigen were detected (Table 1). Binding of lung lavage and serum antibodies from mice immunized with Protollin compositions to the F1 and V portions of the F1-V antigen indicated that the immune response was primarily directed against the V component of the F1-V fusion protein (Table 1). Lung lavage samples also contained significant titers of F1-V specific IgG, even though the titers represented only a small percent of the serum titers (range 0.11%-0.56%; median 0.175%).

TABLE 1

Ratio of Anti-F1 to anti-V Antibodies in Serum and Lung Lavage Fluids of Mice Immunized with Several Formulations of Plague Antigen F1-V

|  | F1-V + 2.5 μg Protollin | F1-V + 1 μg Protollin | F1-V + 0.25 μg Protollin | F1-V i.n. | F1-V + Alhydrogel i.m. |
|---|---|---|---|---|---|
| Serum IgG d35 | 0.31 | 0.30 | 0.34 | 0.31 | 0.65 |
| Serum IgG d55 | 0.25 | 0.26 | 0.33 | 0.58 | 0.29 |
| Lung IgA d35 | 0.42 | 0.39 | 0.33 | N/A | N/A |
| Lung IgA d55 | 0.49 | 0.29 | 0.32 | N/A | N/A |
| Lung IgG d35 | 0.40 | 0.53 | 0.44 | N/A | 1.02 |
| Lung IgG d55 | 0.48 | 0.48 | 0.46 | N/A | 1.03 |

Example 5

Determination of Cytokine Profile after Immunization with Protollin:Plague Antigen To compare the phenotype (type 1 or type 2) of the adaptive immune response elicited by intranasally administered Protollin or injected ALHYDROGEL® adjuvanted F1-V vaccine, splenocytes from selected groups of immunized mice (see Example 4) were re-stimulated in vitro with F1-V. Spleens from each group of mice were pooled and processed into single cell suspensions according to standard methods. The splenic cell suspensions were then incubated with different concentrations of F1-V. Cytokines released into culture supernatants were determined by quantitative ELISA using OPTEIA kits (BD Biosciences, San Jose, Calif.). The amounts of IFN-γ, TNF-α, and IL-5 cytokines released into culture supernatants were determined. Splenocytes from mice immunized intranasally with F1-V (50 μg) mixed with Protollin (1 μg) responded to in vitro re-stimulation by secreting high levels of both IFN-γ and TNF-α; a very low amount of IL-5 was also detected. In contrast, splenocytes from mice immunized by injection of F1-V (20 μg) adsorbed onto Alhydrogel responded by secreting comparatively lower amounts of IFN-γ and TNF-α, although a significant amount of IL-5 was detected. Thus, the cytokine profile elicited by nasal administered of Protollin formulated (adjuvanted) with F1-V antigen was consistent with eliciting a type 1 immune response, whereas the cytokine profile induced by i.m. injection of F1-V antigen formulated with ALHYDROGEL® is more consistent with a response biased toward a type 2 phenotype.

Example 6

Challenge of Immunized Mice with Aerosolized Live *Y. pestis*

Figure 5A:
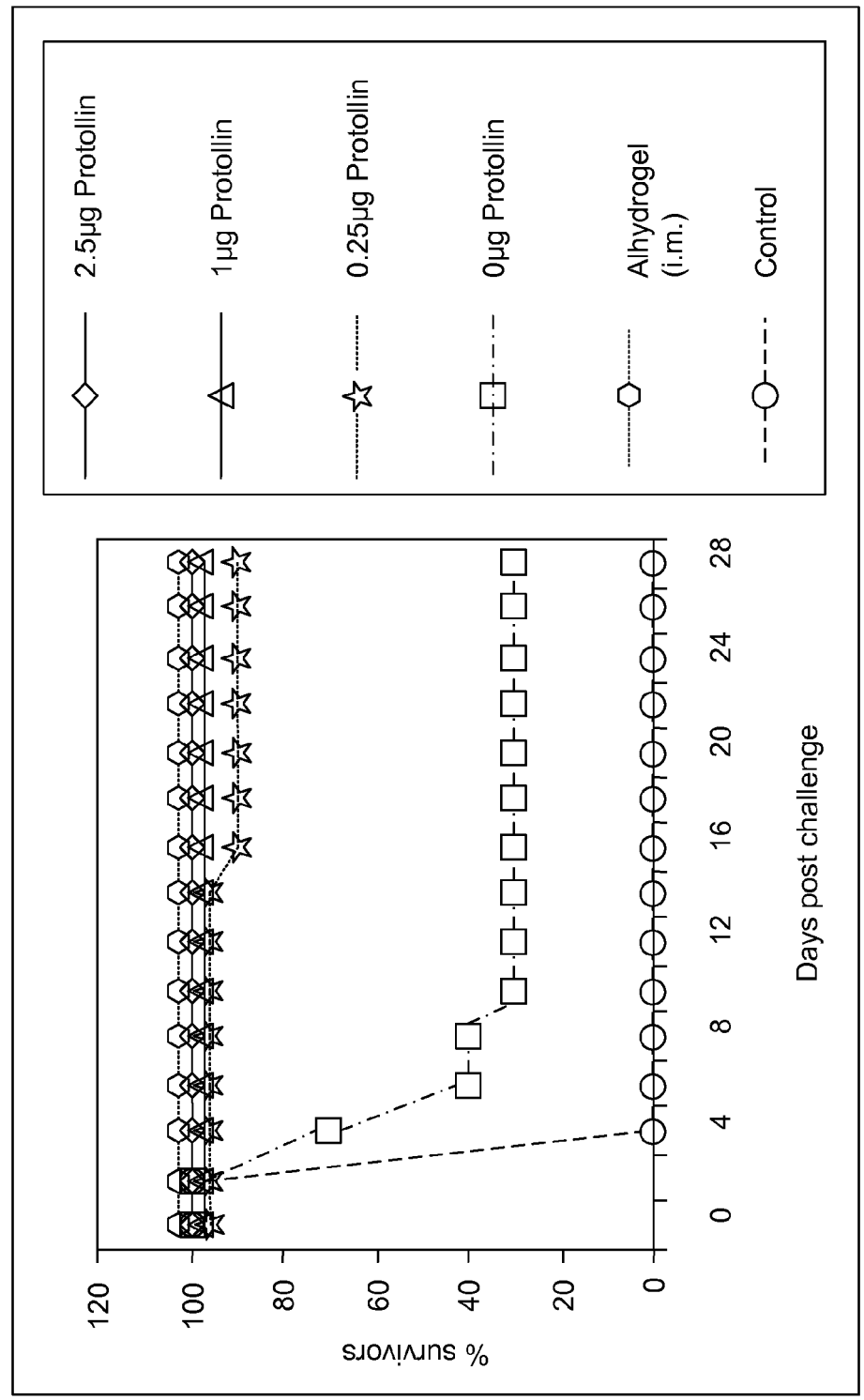
FIGS. 5A-5D show the survival mice after challenge with lethal doses of aersolized Yersinia pestis. Mice were immunized twice with 20 µg of F1-V intranasally with or without Protollin, or with 20 µg of F1-V intramuscularly adsorbed onto ALHYDROGEL®, and then were challenged by whole body exposure to 169 $LD_{50}$ of Y. pestis 35 days (FIG. 5A) or 55 days (FIG. 5B) post-primary immunization. In a second study, mice immunized with 50 µg of F1-V intranasally with or without 1 µg of Protollin, or intramuscularly adsorbed onto ALHYDROGEL®, were challenged by whole body exposure to 254 $LD_{50}$ of Y. pestis 55 days post primary immunization (FIG. 5C).

This Example describes immune protection provided by intranasal immunization with F1-V formulated with Protollin. Mice that received F1-V combined with Protollin were challenged by whole-body exposure to live aerosolized *Y. pestis* (see Example 4). The level of protection from challenge indicated by survival of animals was compared with protection of mice that were injected with F1-V adsorbed onto Alhydrogel and mice that received intranasal administration of F1-V alone or Protollin alone. On day 35 and at a challenge dose of 169 LD$_{50}$ Y. pestis, mice immunized intranasally with 5, 20, or 50 µg of F1-V plus 1 or 2.5 µg of Protollin all survived, as did mice injected with F1-V adsorbed onto Alhydrogel. Survival of mice immunized nasally with 5, 20, or 50 µg of F1-V and 0.25 µg of Protollin was 90%, 100%, and 90%, respectively, while survival of mice immunized nasally with the same doses of F1-V without Protollin was only 30%, 40% and 40%, respectively. None of the control mice that received Protollin alone survived longer than 4 days post challenge. Survival for all mouse groups immunized with F1-V formulated with Protollin was highly significant compared to survival in control mice or mice immunized with F1-V alone (P≤0.05 or better using Fisher's Exact Probability Test). The results for mice immunized with 20 µg doses of F1-V are shown in FIG. 5A, and the results for animals immunized with 5 µg doses of F1-V are shown in FIG. 5D.

Figure 5B:
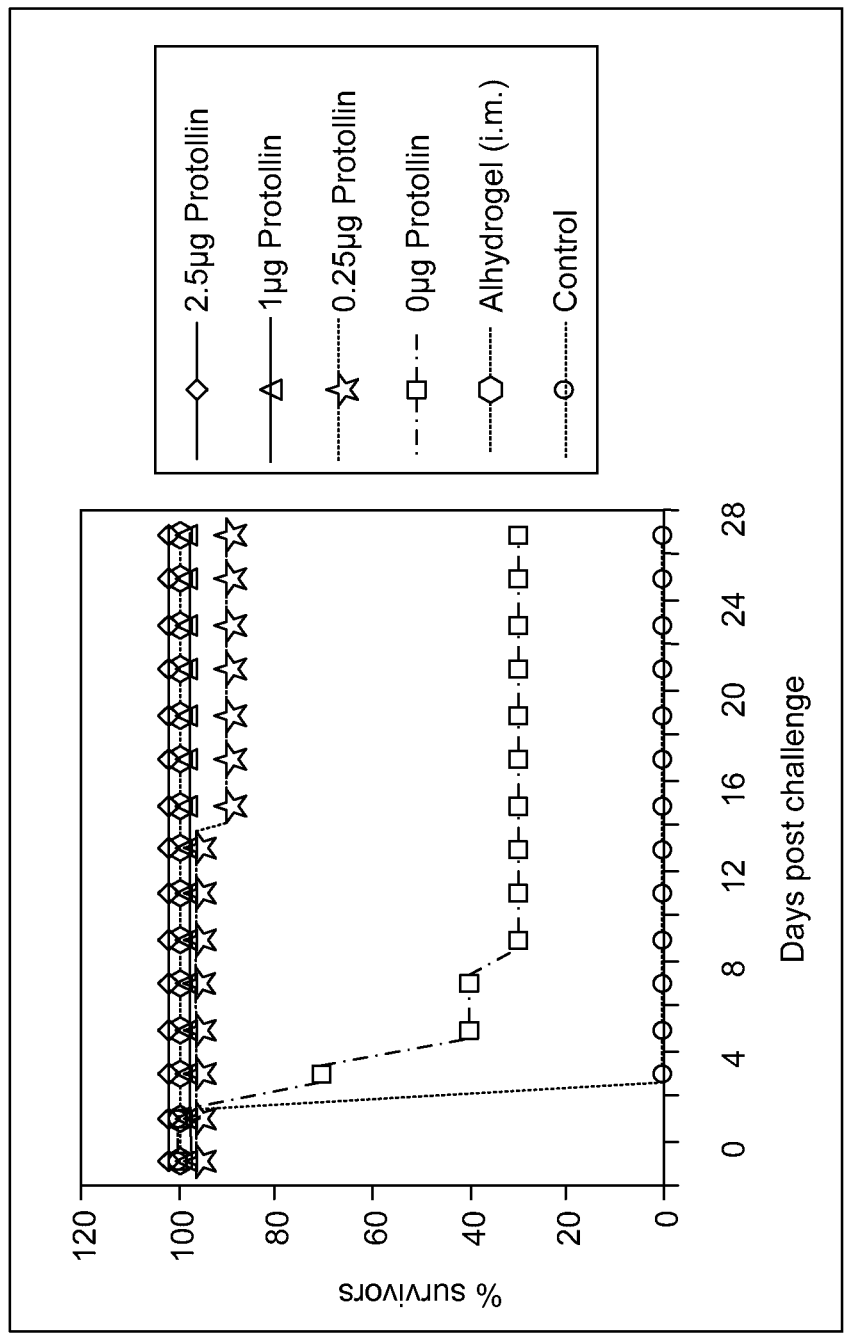

Similar results were obtained when animals were challenged on day 55 (FIG. 5B). All mice immunized with 2.5 µg Protollin formulated with F1-V and mice immunized by injection of F1-V adsorbed onto Alhydrogel survived challenge by Y. pestis. All mice immunized with 1 µg of Protollin formulated with 50 µg or 20 µg of F1-V also survived, while 90% of animals that received all other combinations of Protollin and F1-V survived. In all mice immunized with formulated F1-V (F1-V plus Protollin), the observed protection was highly significant (P≤0.01 or better) compared to mice immunized with unformulated F1-V (10-30% protection) or the Protollin only control group of mice in which no animals survived.

Figure 5C:
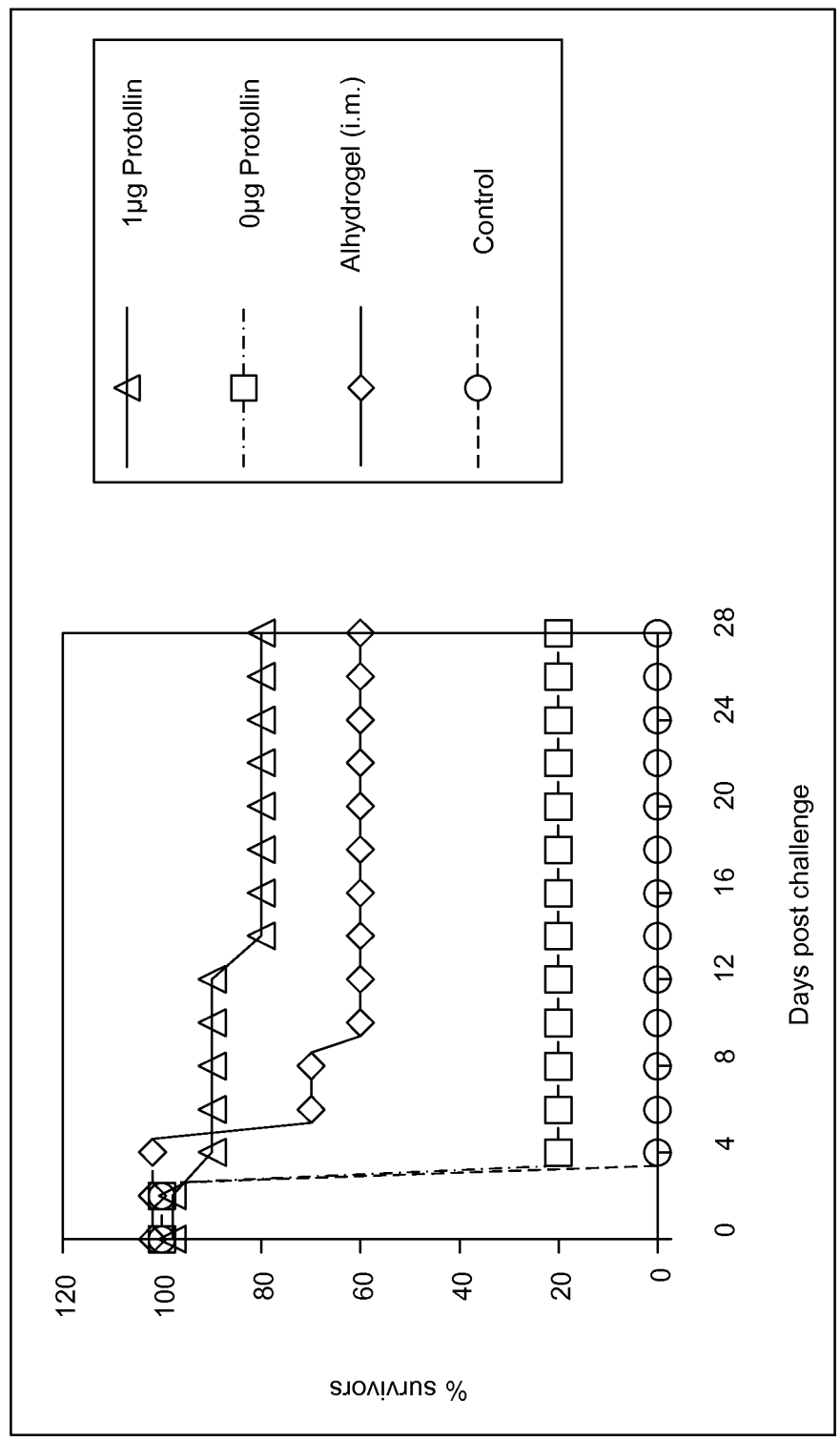
Figure 5D:
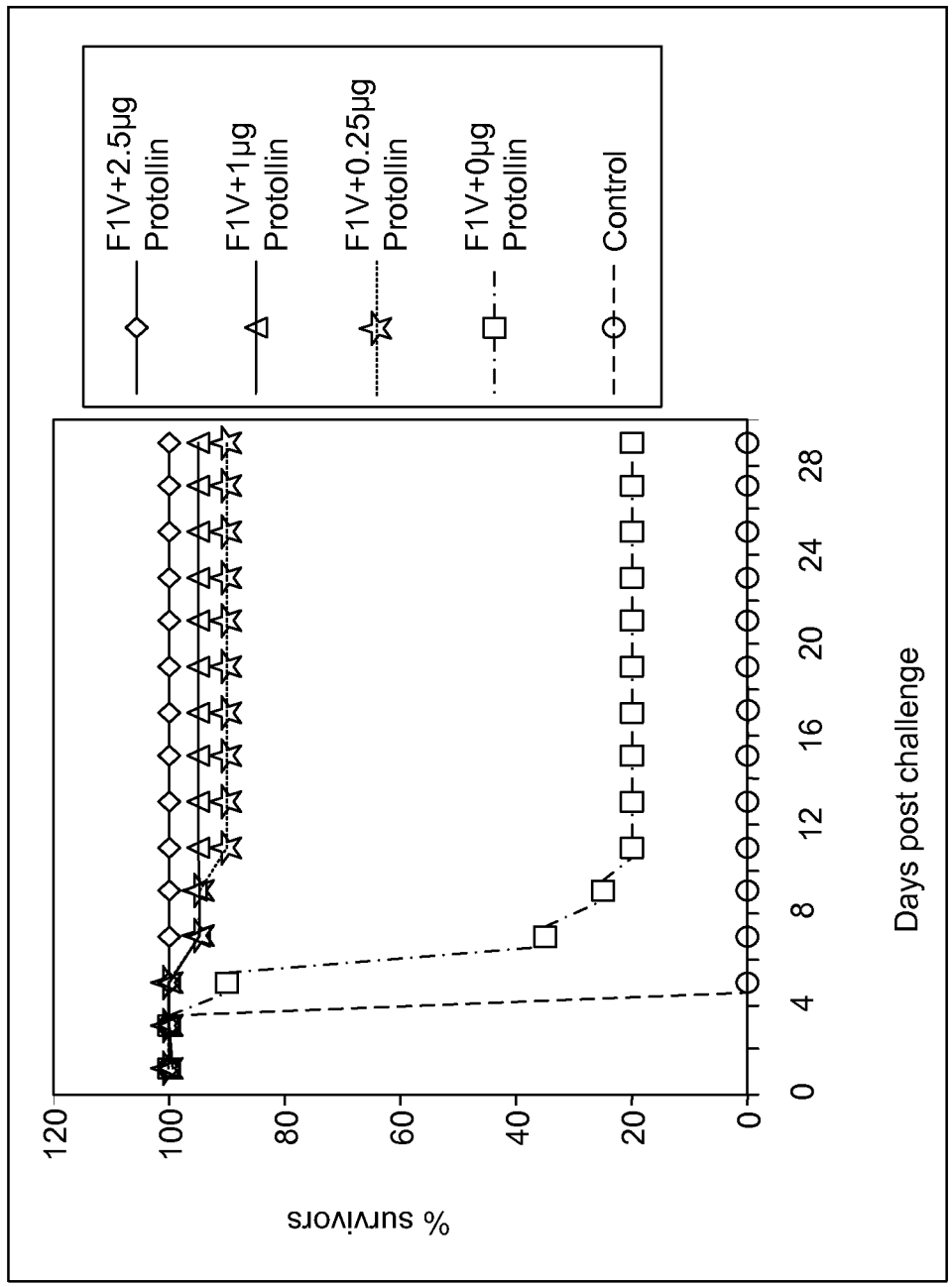

Mice immunized nasally with 50 µg of F1-V with or without 1 µg of Protollin, or that were injected with 20 µg of F1-V adsorbed onto Alhydrogel, were challenged on day 55 by whole body exposure to 254 LD$_{50}$ aerosolized live Y. pestis. The results are presented in FIG. 5C. Eighty percent of the mice that were immunized with 50 µg F1-V plus 1 µg Protolin survived; 60% of mice that were immunized with 20 µg of F1-V adsorbed onto Alhydrogel survived; and 20% of animals that that received F1-V only survived lethal challenge. Control mice given Protollin alone all died. Immunization with formulated F1-V induced significant protection against death compared to control mice (P≤0.001 for nasal F1-V plus Protollin; P≤0.01 for i.m. injected F1-V). Nasal immunization with F1-V plus Protollin offered significantly protection against death than immunization with F1-V alone (P≤0.05). Survival of mice injected with F1-V adsorbed onto Alhydrogel was not significantly better than survival of animals immunized intranasally with F1-V without Protollin (P=0.095).

Example 7

Protection of Mice by Protollin Anthrax Immunogenic Formulations

In this Example, Protollin formulated with Protective Antigen (PA) of Bacillus anthracis (see Example 8) was assessed for its capability to induce an immune response exemplified by a statistically significant reduction in PA-mediated macrophage killing. Mice were immunized nasally on days 0 and 14 with 5 or 25 µg rPA (List Biological Laboratories) admixed with 1 µg of Protollin.

Figure 6A:
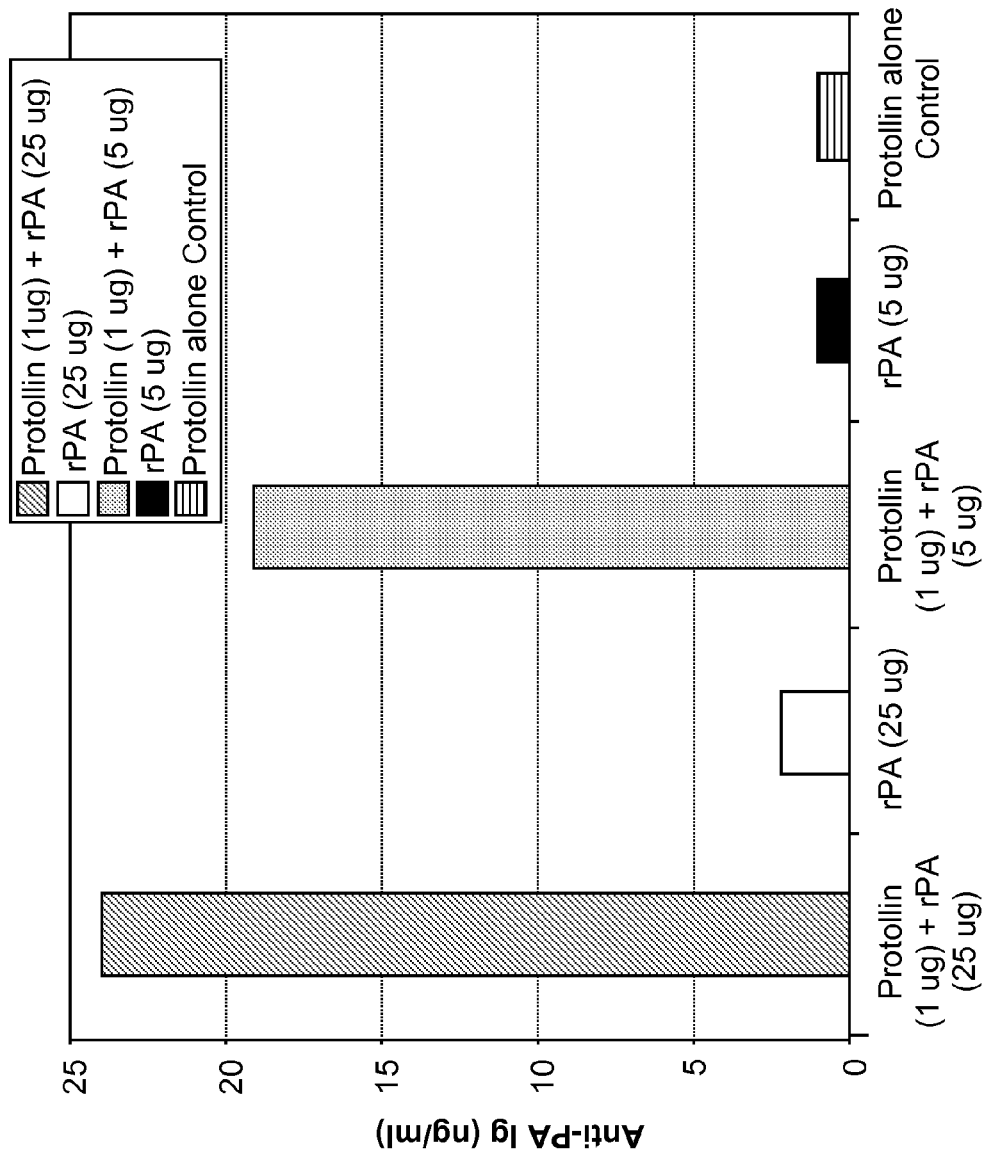
FIG. 6A shows serum IgG levels and FIG. 6B shows lung IgA levels in mice immunized nasally on days 0 and 14 with 5 or 25 µg of recombinant Protective Antigen (rPA) from Bacillus anthracis admixed with Protollin (1 µg) or without Protollin.
Figure 6B:
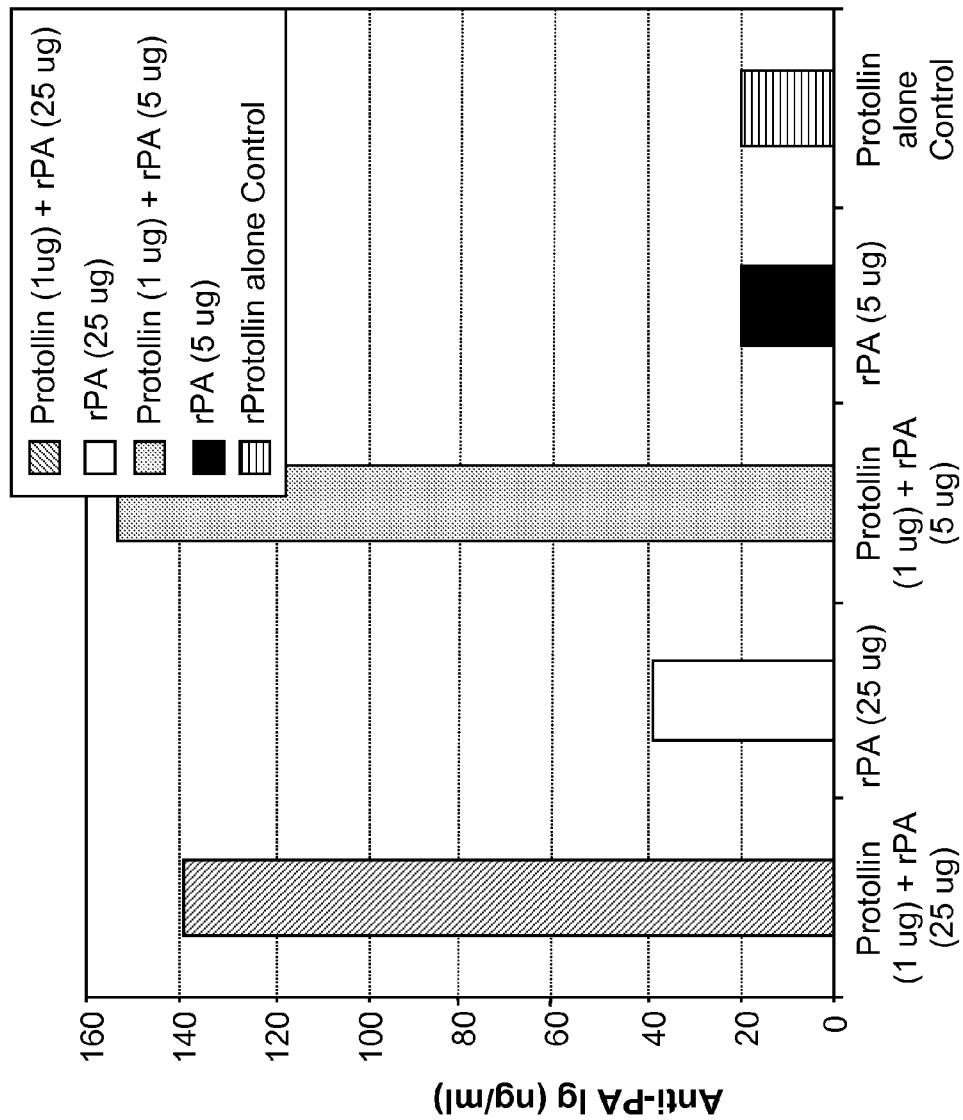

A standard ELISA protocol was used to detect IgG and IgA I serum and lung lavage samples. Briefly, serial dilutions of the test samples (serum and lavage fluids) were added to the wells of ELISA plates that were coated with purified rPA. Antigen-specific antibodies that adhered to the immobilized antigen were detected with anti-mouse constant region antibody conjugated to horseradish peroxidase (HRP). Following incubation of the HRP antibody conjugate, the wells were washed, TMB substrate was added, and the amount of bound HRP antibody was detected by measuring absorbance at 490 nm. Antibody concentrations in the test samples were calculated from standard curves that were run in parallel, using purified standard antibodies for IgA and IgG. ELISA data were expressed as geometric means at 95% confidence levels according to a statistical analysis using log-transformed data. Animals that received Protollin plus PA showed specific anti-PA serum IgG and lung IgA levels that were significantly higher than those of mice that were intranasally administered 5 or 25 µg of rPA alone (p<0.05) (FIG. 6A-B). Mucosal IgA levels in animals treated with the Protollin alone or rPA alone were below the detection level of this assay.

Figure 7A:
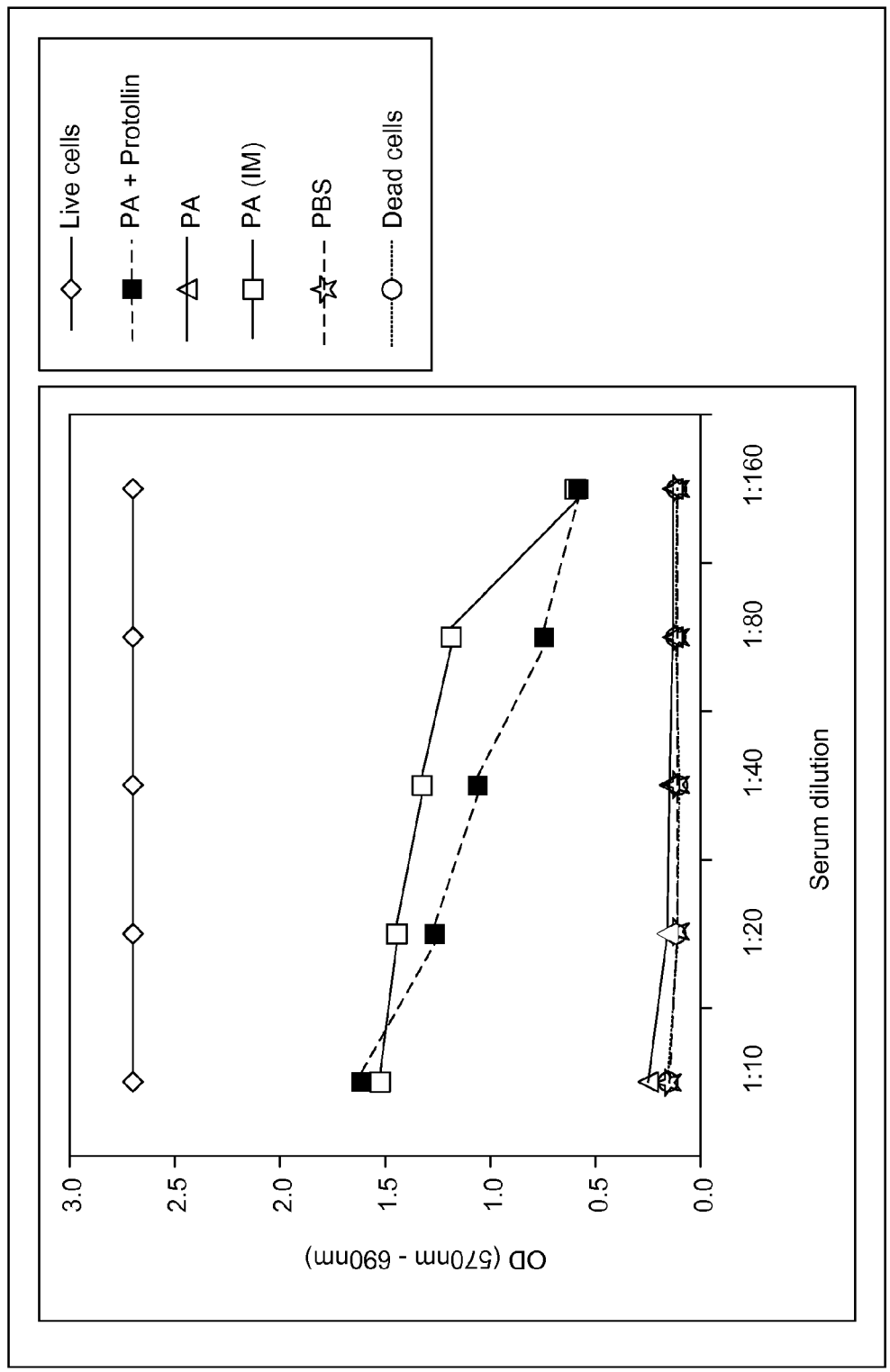
FIGS. 7A and 7B illustrate neutralization of PA-mediated killing of macrophages by serum and lung lavage fluid, respectively, obtained from mice that were immunized with rPA admixed with Protollin (PA+Protollin); rPA alone (PA); or rPA administered intramuscularly (PA (IM)) (figure legend in FIG. 7B defines symbols used in both FIGS. 7A and 7B).
Figure 7B:
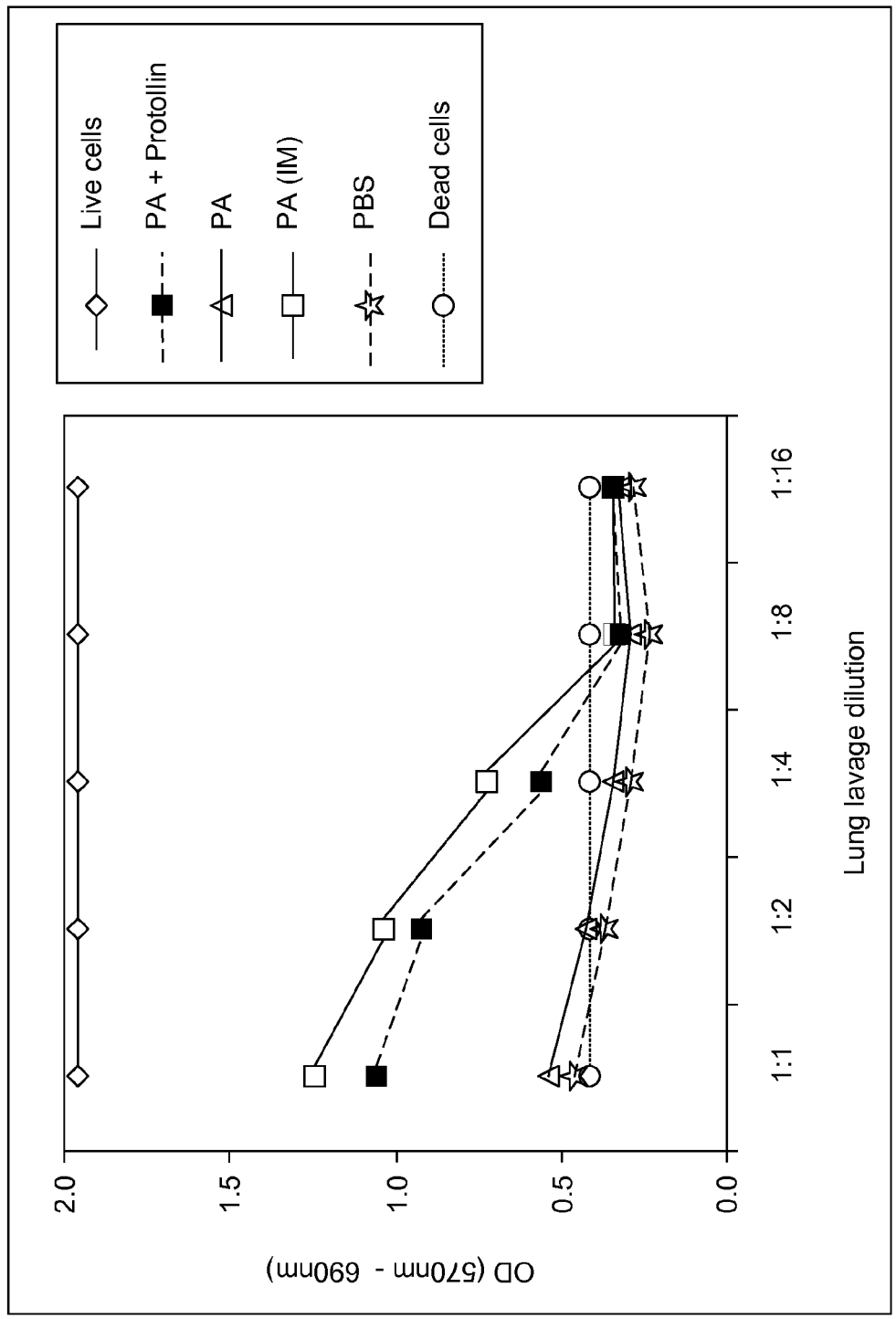

The capability of specific anti-PA antibodies to neutralize PA-mediated macrophage killing was evaluated using a cell culture assay system using serum and lung lavage fluid samples from the animals. RAW264.7 macrophages (ATCC, Manassas, Va.) (2×10$^5$ cells per well) were plated in sterile 96-well plates and incubated at 37° C. for 24 hours in 5% CO$_2$. Serial dilutions of serum or lung lavage fluid samples from the PA-immunized animals were incubated with a PA solution (4 µg/ml in rPMI cell culture media supplemented with 10% fetal bovine serum) 1 hour at 37° C., after which the mixtures were added to the wells containing RAW264.7 cells. A solution of Lethal Factor (LF) was added to the wells, and the plates were incubated at 37° C. in 5% CO$_2$ for 4 hours. A solution of MTT (3-(4,5-dimethylthiazol-2-yl)-2,5-diphenyltetrazolium bromide) (Sigma-Aldrich, St. Louis, Mo.) to measure cell viability was then added to each well, and the plates incubated for 4 hours at 37° C. in 5% CO$_2$. The reaction was stopped by adding 20% SDS in 50% DMF (dimethylformamide), pH 4.3. Optical density is measured with an ELISA plate reader (Molecular Devices, Menlo Park, Calif.) at 570 nm (reference at 690 nm). The assay is linear in for cell concentrations in the range of 10$^4$ to 10$^5$ cells/well. The nasal vaccine, rPA+Protollin, elicited comparable levels of antibodies that neutralized rPA activity as did the IM alum-adjuvanted vaccine (FIG. 7).

Example 8

Preparation of Anthrax Vaccine Formulations

Nasal Protollin anthrax vaccines are made by admixing the anthrax PA antigens with soluble pre-formed Proteosome plus LPS (i.e., Protollin) prior to immunization. Both rPA and rPA-anch (rPa with a hydrophobic anchor sequence) antigens are evaluated with several different formulations of Protollin to determine the formulation(s) with preferred immunogenic antigen and Protollin components. Control formulations consist of, for example, Protollin alone or mixed with at least one and preferably two control antigens, including a recombinant streptococcal protein with or without a hydrophobic anchor sequence (anch). Accordingly, formulations of Protollin that are evaluated have different sources of LPS, varied Proteosome:LPS ratios, and varied Protollin:rPA antigen ratios. rPA-anch is also formulated with Proteosome proteins that have very low levels of LPS (<2% by weight) using the dialysis or diafiltration methodology described herein, which is designed to remove or reduce the concentration of detergent in which the Proteosome adjuvant is stored. These Proteosome adjuvant preparations do not have exogenous LPS added. The Proteosome preparations used to formulate Protollin as described in this example have been used in extensive pre-clinical toxicity studies as well as Phase 1 and Phase 2 human clinical trials to evaluate safety, immunogenicity, and efficacy of a Proteosome nasal influenza vaccine.

The preferred LPS bacterial type and source and the preferred ratio of OMP:LPS formulation is determined by immunogenicity studies. After fermentation of the preferred bacteria, LPS is purified and analyzed. The purified LPS is then mixed with Proteosome OMP particles at the selected ratio to form a OMP:LPS complex, Protollin. The extent of complex formation of the LPS and OMPs is determined according to "free-vs.-bound" assays using capillary electrophoresis, LPS "spiking" studies, and other analyses practiced in the art. Protollin is analyzed for LPS content using KDO, NMR, and silver stain PAGE, and analyzed for Proteosome OMP content using LC-MS, RP-HPLC, SDS-PAGE (Coomassie Blue stain & Western immunoblot using monoclonal and polyclonal antibodies), N-terminal sequencing, amino acid analysis, total protein by Lowry or BCA, and MALDI-TOFMS for example. The presence of residual LPS, nucleic acids, and detergents is determined using various techniques including KDO to determine LPS content and HPLC to determine the presence of detergent.

Example 9

Evaluation of Serum and Mucosal Immune Response

An ELISA is performed to determine total immunoglobulin and *B. anthracis* Protective Antigen (PA)-specific IgG, IgA, and IgM titers in biological samples obtained from animals (mice, rabbits) immunized with test immunostimulatory or immunogenic formulations as described herein. Samples include serum, nasal and lung mucosal washes. A standard ELISA protocol is used to determine linearity, specificity, sensitivity, and reproducibility. Briefly, serial dilutions of the test samples (serum and lavage fluids) are added to the wells of ELISA plates that are coated with purified rPA, or derivatives thereof. Antigen-specific antibodies that adhere to the immobilized antigen are detected with animal (for example, and anti-rabbit or anti-mouse constant region antibody) and antibody-subtype specific horseradish peroxidase (HRP) conjugated antibodies. Following incubation of an HRP antibody conjugate, the wells are washed, TMB substrate is added, and the amount of bound HRP antibody is detected by measuring absorbance at 490 nm. Antibody concentrations in the test samples are calculated from standard curves that are run in parallel, using purified standard antibodies for IgA, IgM, and/or IgG (including mouse isotypes, IgG1 and IgG2a). When appropriate, specific antibody levels in mucosal wash fluid samples are standardized and normalized by expressing the specific antibodies detected in comparison to the total amount of IgA or IgG in the sample. ELISA data are expressed as geometric means at 95% confidence levels according to a statistical analysis using log-transformed data.

Example 10

Macrophage Protection Assay to Evaluate for Anthrax Neutralizing Antibodies

This Example describes an assay that is used to measure neutralizing antibodies from animals immunized with Proteosome vaccines. In vitro assays are designed to measure inhibition of anthrax toxin cytotoxicity by serum samples obtained from immunized animals. Serial dilutions of the serum samples are added in combination with lethal quantities of anthrax PA and Lethal Factor (LF) (List Biological Laboratories, Cambell, Calif.) to J774A.1 macrophage cells or other macrophage cell line for 3 hours at 37° C. in a 96-well plate. Cell viability is measured chromatographically by adding one-tenth volume solution of 5 mg/ml MTT. After an incubation of 4 h at 37° C., the assay plates are analyzed spectrophotometrically at 570 nm using an ELISA plate reader (Molecular Devices, Menlo Park, Calif.). The assay is linear for cell concentrations in the range of $10^4$ to $10^5$ cells/well.

Example 11

Cell Mediated Immunity Assay to Evaluate Immunization Against Anthrax

Cellular immune responses that are induced following immunization with the Proteosome-based PA vaccines are studied using a variety of methods. For example, T cell-derived cytokines are assessed on PA-re-stimulated purified or enriched T cells isolated from mouse spleen and/or mediastinal lymph nodes. The presence and levels of Type 1 (e.g., IFN-γ) and type II (e.g., IL-4 and IL-5) cytokines are determined by one or more methods including ELISA, ELISPOT. The presence and levels of intracellular cytokines is determined by standard flow-cytometry methods. Techniques that measure proliferation of PA-re-stimulated PBMC T cells are used to evaluate cell-mediated immune responses in rabbits due to unavailability of reagents that are specific for rabbit cytokines.

T lymphocyte proliferation assays are used to measure the effect of immunization on clonal expansion and determine the presence of memory lymphocytes in animals from various animal models. Following animal sacrifice, mediastinal and cervical lymph nodes are surgically removed using standard techniques, the lymphocytes are isolated and then cultured with and without PA. Proliferation is measured by uptake of $^3$H-thymidine. Cells from animals immunized with sham vaccine will be used as negative controls. Assay results are used to determine the effect of immunization on T cell differentiation in the lymph nodes, particularly in relation to mucosal immunity. The results are also correlated with efficacy of immunization determined in anthrax challenge animal studies.

Example 12

Methods for Collecting Nasal Wash and Lung Lavage

Lung and nasal washes from mice and rabbits were collected to analyze the immune response to immunostimulatory or immunogenic formulations. In mice, nasal washes and lung lavage were performed by cannulating the trachea and pumping 1 ml PBS supplemented with 0.1% bovine serum albumin and protease inhibitors (General Use Protease Inhibitor Cocktail; Sigma-Aldrich Chemicals containing 0.2 mM AEBSR, 1 μg/ml aprotinin, 3.25 μM bestatin, 10 μM Leupeptin) upwards through the trachea. Fluid emerging from the nostrils was collected, vortexed, and then centrifuged to remove tissue and cell debris. The supernatants were stored at −70° C. A cannula was reinserted into the trachea and directed toward the lung for collection of lung fluids. Lungs were lavaged twice with 1.0 ml protease supplemented PBS; the fluid was collected and vortexed; and the cell debris removed by centrifugation. Lung and nasal washes were stored at −70° C. Rabbit mucosal fluids were similarly collected, adjusting the volumes as appropriate. In certain experiments, after collecting mucosal samples, cervical and mediastinal lymph nodes were surgically removed and mononuclear cells isolated and cultured for ELISPOT antibody, cytokine, and CMI assays as described herein.

Example 13

Eliciting Innate Immunity in Rabbits with Protollin

Protollin has adjuvant activity related to both Proteosomes and LPS. Capability of Protollin alone (without antigen) to stimulate innate immunity against aerosol challenge with various pathogens, such as *Chlamydia trachomatis* or *Bacillus anthracis*, is determined. Rabbits are challenged via aerosol with 100 or 200 $LD_{50}$ of anthrax spores within a few days, or longer, after receiving Protollin. Rabbits that survive the anthrax challenge are immunized again with Protollin to determine if protection can be prolonged or innate immunity restimulated.

Example 14

Induction of an Immune Response by Proteosome:LPS Formulations Against Challenge with Chlamydia Trachomatis

*Chlamydia* LPS is highly conserved among various *Chlamydia* strains and data suggest that antibodies specific for *Chlamydia*-genus specific LPS may protect against *Chlamydia* infection (Peterson et al., *Infect. Immun.* 66: 3848, 1998). *Chlamydia* LPS was produced in a recombinant *Escherichia coli* that synthesizes both *E. coli* LPS and a rough 'chlamydia-like' mutant (rLPS) in equal proportions (C.t./*E. coli* rLPS) (purchased from GlycoTech, Kukels, Germany). A murine lung model for *Chlamydia* infection was used to evaluate the immune response effected by C.t./*E. coli* rLPS formulated with Protollin.

Proteosome:LPS compositions were prepared using a dialysis procedure with C.t./*E. coli* rLPS. Proteosomes alone (solubilized in 0.1% Empigen® BB detergent) or solubilized with LPS (solubilized in 1% Empigen® BB detergent) at a final concentration of 1 mg/ml Proteosomes were added to SpectraPor® dialysis tubing with a 1,000 MW cutoff. Dialysis was performed against phosphate buffered saline (PBS) for 10 days or longer. The duration of dialysis can be adjusted to retain varying amounts of detergent in the vaccine formulation including, for example, concentrations from 250, 500, 750, 1000 ppm, or more, or even lower amounts (e.g., 50 ppm). The concentration of LPS in the dialyzed samples was determined by measuring 3-Deoxy-D-manno-octulosonate, and the concentration of protein was determined using the standard Lowry method. A mixture of Proteosomes and C. tr./*E. coli* LPS prior to dialysis was approximately at a ratio of 1:2.7 (weight Proteosomes:weight C. tr./*E. coli* LPS), which resulted in a ratio of approximately 1:1.8 post-dialysis. A mixture of Proteosomes and *E. coli* LPS prior to dialysis was 1:1.35 and was approximately 1:1.4 after dialysis.

In order to determine whether *Chlamydia* LPS provided in a proteosome formulation is able to protect mice specifically against a live *Chlamydia* bacterial challenge, groups of 16 mice (6-8 weeks-old) were anesthetized and then immunized intranasally on days 0 and 22 with Proteosome:C.t./*E. coli* rLPS. Mice were also treated with Proteosome:*E. coli* LPS, or Proteosome:*Plesiomonas shigelloides* LPS. The Proteosome: LPS formulations were given at Proteosome:LPS ratios and doses described in Table 2. Other groups of mice were given either 400 infection units (IFUs) of live CT MoPn (positive control) or HeLa cell extract (negative control; corresponding to the volume of extract required to purify 400 IFUs of mouse pneumonitis strain of *C. trachomatis* (CT MoPn) grown in infected HeLa cells) as a single dose on day 0. All immunizations were given in volumes of 25 μl (12.5 μl/nostril).

Blood was aseptically collected from the retroorbital sinuses of each mouse on day −1 and day 30. Bronchoalveolar lavages were performed on day 30 on 6 mice per group. On day 34, each of the remaining 10 mice/group was given an intranasal challenge with 5,000 IFUs of live CT MoPn. Daily body weights of these mice were measured for 10 consecutive days. Cardiac exsanguination and lung collection were performed on mice sacrificed during this 10-day period. The quantity of *Chlamydia* IFUs in the lungs was determined by applying lung and lavage samples to HeLa cells and identifying *Chlamydia* elementary bodies (EB) using fluorescent specific anti-*Chlamydia* monoclonal antibodies.

Mice that were immunized nasally with 400 IFUs CT MoPn (group 2 Ct400) were highly protected against body weight loss (BW max loss) (Table 3; P=0.001326). None of the mice in this group had detectable *C. trachomatis* in their lungs (Table 4; $P=4\times10^{-9}$) up to ten days after intranasal challenge with 5,000 IFUs CT MoPn. Control mice that received HeLa cell extract (group 1 HELA) were not protected from lethal challenge as shown by high body weight maximum losses (% reduction) and high titers of *Chlamydia* infection units (IFUs) in the lungs (Tables 3 and 4). Mice treated with proteosome preparations containing *Chlamydia* LPS, and also either *E. coli* or *P. shigelloides* LPS, showed significant protection against weight loss and bacterial growth (Tables 3 and 4).

To investigate whether protection may be due, at least in part, to specific anti-*Chlamydia* LPS antibodies, the presence of *Chlamydia* specific antibodies in sera and lung from immunized mice was determined by ELISA using inactivated whole cell *Chlamydia* as the antigen source. Sera were obtained from animals immunized with proteosome-LPS vaccines two weeks after the second immunization on Day 22. Sera from animals immunized with HeLa cell extract or CT-MoPn were obtained on day 30 after the first and only immunization. Results presented in Table 2 demonstrated that antibodies present in serum and lung from animals given Proteosomes formulated with *Chlamydia* LPS bound to whole cell *Chlamydia*.

To determine if the antibodies that bound to *Chlamydia* cross-reacted with epitopes present on *E. coli* LPS and *P. shigelloides* LPS, binding of antibodies in sera and lung from treated animals to these LPS types was also determined by ELISA. The results presented in Table 2 demonstrated that antibodies in the sera of mice immunized with each of the specific LPS types in the Proteosome:LPS formulations bound only to the corresponding LPS. Only antibodies from animals immunized with proteosome-formulated *Chlamydia* LPS bound to whole cell *Chlamydia*. Proteosome formulated with LPS from either *E. coli* alone or *P. shigelloides* failed to bind to whole cell *Chlamydia*; however, these preparations significantly protected mice against *Chlamydia* challenge (see Tables 3 and 4).

TABLE 2

Immunogenicity of Protollin Compositions Administered Intranasally to BALB/c Mice

| Group | Antigens[1] | Dose Level Ratio µg Projuvant:µg LPS | Serum Anti-LPS IgG Ab Titers[2] C. t./E. coli rLPS | E. coli LPS | P. shig. LPS | Anti-C. tr. MoPn EB Titers (ng/ml) Serum[3] IgG | Lung[4] IgA | Lung[4] IgG |
|---|---|---|---|---|---|---|---|---|
| 1 | HeLa cell extract | Not applicable | — | — | — | <40 | <12 | <2 |
| 2 | Live EBs CT-MoPn | 400 IFUs | 1280 | — | — | 10,906 | 669 | 173 |
| 3 | E. coli LPS | 12:8 | 160 | 1280 | — | <40 | 378 | <2 |
| 4 | C.t./E. coli rLPS | 1.5:1 | 640 | 40 | — | 3,158 | 1532 | 109 |
| 5 | C.t./E. coli rLPS | 1.6:8 1:5 | 320 | — | — | 2,187 | 404 | 15 |
| 6 | P. shigella LPS | 10:8.6 1:1 | — | — | >>2560 | <40 | <12 | <2 |

[1]Intranasal immunizations (25 µl, 12.5 µl/nostril) were given once at Day 0 to Group 1 (HELA cells) and group 2 (*Chlamydia trachomatis*)) or given twice, Day 0 (upper ratio) and Day 22 (lower ratio) to group 3-6 (proteosome:LPS vaccines) to anesthetized mice (16 mice/group).
[2]Anti-LPS antibody titers in sera (pools from 6 mice) obtained 5 weeks (day 30) post first immunization (2 weeks post-second immunization with proteosome-LPS vaccines) are expressed as dilution that gave an O.D. at 450 nm approximately twice greater than the background.
[3]No serum anti-*Chlamydia* IgA was detected independent of the antigen used for immunization.
[4]For groups 1 and 2, pools of homogenized lungs were analyzed. For groups 3-6, pools of lung lavages were analyzed. The lungs and lung lavages were obtained on day 30.
"—": No antibody detected.

TABLE 3

Percent Body Weight Reduction (Maximum Loss) Post-Second Treatment

| Mouse # in Group | 1 HeLa | 2 Ct400 | 3 Ec12:8 | 4 Ct12:8 | 5 Ct1.6:8 | 6 Ps10:9 |
|---|---|---|---|---|---|---|
| 1 | 29.3 | 2 | 10.6 | 11.2 | 11.7 | 15.5 |
| 2 | 19.4 | 1.1 | 32.6 | 8.7 | 7.4 | 1.7 |
| 3 | 35.5 | 9.8 | 15.1 | 5.8 | 18 | 11.4 |
| 4 | 28.6 | 16.9 | 16.2 | 7 | 20.5 | 14.2 |
| 5 | 28.3 | 14.5 | 37.7 | 16.4 | 7 | 7 |
| 6 | 30.3 | 17.6 | 17.5 | 11.7 | 12.3 | 8.1 |
| 7 | 36.9 | 6.8 | 5.9 | 36.8 | 4.2 | 6.2 |
| 8 | 23.1 | | 3.1 | 8.4 | 41.2 | 7.9 |
| 9 | 25.7 | 9 | 8.9 | 4.5 | 24.2 | 9.1 |
| 10 | 26.2 | 20.9 | 28.6 | 2.6 | 8.5 | 13.5 |
| Gmean | 27.88 | 7.89 | 13.85 | 8.79 | 12.56 | 8.25 |
| t-test log vs HeLa | | 0.001326 | 0.014 | 0.000124 | 0.00224 | $1.727 \times 10^{-5}$ |

TABLE 4

*C. trachomatis* IFUs in the Lung Post-Second Treatment

| Mouse # in Group | 1 HeLa | 2 Ct400 | 3 Ec12:8 | 4 Ct12:8 | 5 Ct1.6:8 | 6 Ps10:9 |
|---|---|---|---|---|---|---|
| 1 | 48500 | 9 | 9 | 9 | 9 | 1100 |
| 2 | 51300 | 9 | 91000 | 9 | 9 | 9 |
| 3 | 1100 | 9 | 9 | 9 | 14900 | 290 |
| 4 | 6000 | 9 | 2250 | 9 | 1500 | 9 |
| 5 | 200 | 9 | 24400 | 9 | 9 | 9 |
| 6 | 35000 | 9 | 500 | 3150 | 9 | 9 |
| 7 | 47000 | 9 | 9 | 46500 | 9 | 9 |
| 8 | 1300 | 9 | 9 | 9 | 29400 | 320 |
| 9 | 63000 | 9 | 9 | 9 | 16300 | 9 |
| 10 | 77000 | 10 | 1900 | 9 | 9 | 5000 |
| Gmean | 11304.14 | 9.10 | 221.18 | 38.02 | 149.81 | 55.38 |
| t-test log vs HeLa | | $4 \times 10^{-9}$ | 0.0088 | 0.00015 | 0.0050 | $6.71 \times 10^{-5}$ |

Ct400 - *Chlamydia*;
Ec12:8 - *E. coli* LPS;
Ct12:8 or Ct1.6:8 - *Chlamydia*/*E. coli* LPS; and
Ps10:9 - *P. shigelloides* LPS.

Example 15

Duration of Innate Immune Response Protection Against Chlamydia

The longevity of the nonspecific protection induced by immunostimulatory compositions, such as Proteosome:LPS (Protollin) or Proteosomes (projuvant), was examined. Groups of 10 mice were treated on day 0 and day 22 with (a) Proteosomes alone (Prot10), (b) Proteosomes formulated with LPS from *E. coli* (Ec10:14); (c) Proteosomes formulated with C.tr./*E. coli* LPS (Ct10:18); (d) Proteosomes formulated with LPS from *P. shigelloides* (Ps10:12); (e) live *Chlamydia* (800 IFUs) (CT800); or (f) HeLa cell mock infection (HeLa). For each treatment, different groups of mice were challenged with viable *Chlamydia* bacteria at 2, 5, 8, or 11 weeks post-second treatment. Protection was evaluated by determining maximum body weight loss (% reduction) and determining *Chlamydia* IFUs in the lung for each mouse (designated by Mouse # in Group). The data are presented in Tables 5-12.

As described in Example 14, treatment with each of the Proteosome:LPS formulations or immunization with live *Chlamydia* provided significant protection compared to the HeLa cell control groups as indicated by prevention of weight loss and/or reduction in bacterial titers in the lung. Protection of animals treated with Proteosomes alone lasted for approximately 5 weeks after the second immunization. An assay to determine the T cell proliferative response following re-stimulation with *Chlamydia* antigen was performed with mouse splenocytes. Spleens from each group of mice were pooled and processed into single cell suspensions according to standard methods. The splenic cell suspensions were then incubated with different concentrations of *Chlamydia* antigen. Cytokines (IFN-γ, IL-10, IL-2, and TNF-α) released into culture supernatants were determined by quantitative ELISA using OptEIA kits (BD Biosciences, San Jose, Calif.). In these experiments *Chlamydia*-specific splenic T cell responses induced by the Proteosome:LPS formulations were not observed in immunized mice. In the absence of *Chlamydia*-specific antibody or antigen-specific T cell responses in these immunized animals, a role for nonspecific, antigen-independent (innate) immunity is suggested as a mechanism for protecting mice from *Chlamydia* lung infection. Similarly, in the experiment described in Example 14, an antigen-specific T cell response was observed only in animals that received *Chlamydia* bacteria and not in animals that received any of the Proteosome:LPS formulations.

TABLE 5

Body Weight Maximum Loss Measured after Challenge 2 Weeks Post-Second Immunization

| | Group | | | | | |
|---|---|---|---|---|---|---|
| Mouse # in Group | 1 HeLa | 2 CT800 | 3 Ec10:14 | 4 Ct10:18 | 5 Ps10:12 | 6 Prot10 |
| 1 | 33.6 | 17 | 37 | 23.6 | 35 | 30.3 |
| 2 | 34.4 | 12.7 | 17.4 | 34.1 | 14.6 | 15.6 |
| 3 | 41.1 | 13 | 23.2 | 8.3 | 2.8 | 31.7 |
| 4 | 36.5 | 13.9 | 29.3 | 8.1 | 9.4 | 38.7 |
| 5 | 29.1 | 5.8 | 22 | 16.7 | 15.2 | 25 |
| 6 | 41.1 | 12.1 | 30.1 | 10.8 | 11.7 | 26.8 |
| 7 | 38.1 | 10.9 | 12.3 | 7.6 | 10.7 | 15.5 |
| 8 | 34.3 | 2.9 | 34.5 | 8.1 | 10.2 | 25.3 |
| 9 | 30.1 | 21.4 | 15 | 4.4 | 14.3 | 19.9 |
| 10 | 30.5 | 19.2 | 23.6 | 39.4 | 22.6 | 23.5 |
| G mean | 34.64 | 11.35 | 23.11 | 12.64 | 12.38 | 24.28 |
| t-test log vs. HELA | | $1.83 \times 10^{-5}$ | 0.003578 | 0.000393 | 0.000123 | 0.00253 |

TABLE 6

Lung *Chlamydia* IFUs Quantified after Challenge 2 Weeks Post-Second Immunization

| | Group | | | | | |
|---|---|---|---|---|---|---|
| Mouse # in Group | 1 HeLa | 2 CT800 | 3 Ec10:14 | 4 Ct10:18 | 5 Ps10:12 | 6 Prot10 |
| 1 | 465000 | 9 | 368000 | 41700 | 5300000 | 100000 |
| 2 | 4920000 | 9 | 25600 | 4200000 | 20000 | 9 |
| 3 | 1170000 | 9 | 725000 | 9 | 9 | 1200000 |
| 4 | 2270000 | 9 | 1510000 | 9 | 9 | 100000 |
| 5 | 497000 | 9 | 128000 | 272000 | 58100 | 72400 |
| 6 | 8660000 | 9 | 124000 | 69000 | 9 | 114000 |
| 7 | 2010000 | 9 | 60800 | 9 | 9 | 9 |
| 8 | 273170 | 9 | 1180000 | 9 | 9 | 437000 |
| 9 | 70100 | 9 | 44200 | 9 | 27100 | 33000 |
| 10 | 456000 | 10 | 52700 | 2850000 | 69500 | 28900 |
| G mean | 925084.91 | 9.10 | 175269.07 | 1880.56 | 962.86 | 17882.17 |
| t-test log vs. HELA | | $1.6705 \times 10^{-15}$ | 0.019655 | 0.00418 | 0.000736 | 0.010898 |

Values of 9 and 10 were used for calculations of t-test; however, *Chlamydia* was not detected.

TABLE 7

Body Weight Maximum Loss Measured after Challenge 5 Weeks Post-Second Immunization

| Mouse # in Group | Group | | | | | |
|---|---|---|---|---|---|---|
| | 1 HeLa | 2 CT800 | 3 Ec10:14 | 4 Ct10:18 | 5 Ps10:12 | 6 Prot10 |
| 1 | 24.1 | 12.9 | 8.9 | 37.2 | 20.7 | 11.6 |
| 2 | 31.7 | 20.4 | 8.2 | 12.1 | 28.6 | 11.3 |
| 3 | 31.5 | 13.5 | 32.7 | 24.9 | 13.5 | 19.8 |
| 4 | 39.4 | 15.5 | 15.2 | 14.5 | 18.9 | 26.3 |
| 5 | 40.9 | 12.1 | 22.5 | 26.2 | 25.8 | 32.2 |
| 6 | 33.8 | 4.7 | 30.2 | 26.1 | 24.3 | 11.2 |
| 7 | 25.7 | 28.9 | 2.5 | 25.1 | 15.2 | 20.9 |
| 8 | 23.3 | 17.4 | 38.3 | 18.5 | 5.2 | 15.3 |
| 9 | 40.1 | 11.8 | 24.6 | 15.9 | 10.4 | 37 |
| 10 | 39.4 | 13.4 | 13.5 | 38.9 | 10.8 | 8.3 |
| G mean | 32.31 | 13.79 | 15.47 | 22.41 | 15.58 | 17.31 |
| t-test log vs. HELA | | $5.9122 \times 10^{-5}$ | 0.01443 | 0.018168 | 0.000717 | 0.002056 |

TABLE 8

Lung *Chlamydia* IFUs Quantified after Challenge 5 Weeks Post-Second Immunization

| Mouse # in Group | Group | | | | | |
|---|---|---|---|---|---|---|
| | 1 HeLa | 2 CT800 | 3 Ec10:14 | 4 Ct10:18 | 5 Ps10:12 | 6 Prot10 |
| 1 | 61200 | 9 | 9 | 573000 | 29200 | 9 |
| 2 | 1220000 | 9 | 9 | 172000 | 38900 | 9 |
| 3 | 4620 | 9 | 75600 | 686000 | 20000 | 96900 |
| 4 | 2570000 | 9 | 41900 | 97000 | 26300 | 217000 |
| 5 | 5910000 | 9 | 62300 | 181000 | 40000 | 121000 |
| 6 | 1420000 | 9 | 9710000 | 863000 | 69300 | 9 |
| 7 | 200000 | 9 | 9 | 157000 | 82800 | 52300 |
| 8 | 9 | 9 | 7000000 | 9 | 9 | 83300 |
| 9 | 538000 | 9 | 889000 | 9 | 9 | 339000 |
| 10 | 889000 | 10 | 9 | 409000 | 9 | 9 |
| G mean | 151583.48 | 9.10 | 6156.61 | 37381.58 | 3162.18 | 2749.09 |
| t-test log vs. HELA | | $4.179 \times 10^{-7}$ | 0.1725 | 0.4684 | 0.0456 | 0.0615 |

Values of 9 and 10 were used for calculations of t-test; however, *Chlamydia* was not detected.

TABLE 9

Body Weight Maximum Loss Measured after Challenge 8 Weeks Post-Second Immunization

| Mouse # in Group | Group | | | | | |
|---|---|---|---|---|---|---|
| | 1 HeLa | 2 CT800 | 3 Ec10:14 | 4 Ct10:18 | 5 Ps10:12 | 6 Prot10 |
| 1 | 35.1 | 9 | 23.7 | 7.5 | 14 | 35.6 |
| 2 | 34 | 10.2 | 11.6 | 10.8 | 26.9 | 25.6 |
| 3 | 16.1 | 7.6 | 21.2 | 9.9 | 12.8 | 31.7 |
| 4 | 15.2 | 13.2 | 8.7 | 18.1 | 21.9 | 25.2 |
| 5 | 34.7 | 18.7 | 15.9 | 18.1 | 17.5 | 9.5 |
| 6 | 36.4 | 8.2 | 34.9 | 6 | 24.5 | 20.3 |
| 7 | 32.2 | 12.4 | 10.6 | 11.7 | 27.4 | 33.2 |
| 8 | 33.5 | 20.8 | 26.4 | 26.2 | 6.7 | 25.5 |
| 9 | 32.1 | 10.2 | 9.7 | 5.1 | 16.7 | 15.3 |
| 10 | 38.6 | 13.9 | 7.7 | 18.7 | 14.4 | 13.6 |
| G mean | 29.46 | 11.78 | 15.03 | 11.65 | 16.98 | 21.84 |
| t-test log vs. HELA | | $9.657 \times 10^{-6}$ | 0.00314 | 0.000218 | 0.00505 | 0.1013 |

TABLE 10

Lung *Chlamydia* IFUs Quantified after Challenge 8 Weeks Post-Second Immunization

| Mouse # in Group | Group | | | | | |
|---|---|---|---|---|---|---|
| | 1 HeLa | 2 CT800 | 3 Ec10:14 | 4 Ct10:18 | 5 Ps10:12 | 6 Prot10 |
| 1 | 6840000 | 9 | 11200 | 9 | 92400 | 355000 |
| 2 | 226000 | 9 | 9 | 129000 | 257000 | 157000 |
| 3 | 9 | 9 | 14200 | 9 | 9 | 4260000 |
| 4 | 9 | 9 | 3340 | 137000 | 5770 | 69200 |
| 5 | 2040000 | 9 | 57700 | 352000 | 15600 | 6650 |
| 6 | $5.33 \times 10^7$ | 9 | 1710000 | 3530 | 18500 | 198000 |
| 7 | 1210000 | 10000 | 9 | 9 | 345000 | 7140000 |
| 8 | $1.44 \times 10^7$ | 9 | 28200 | 15300 | 3040 | 124500 |
| 9 | 667000 | 9 | 9 | 9 | 47300 | 163000 |
| 10 | 2210000 | 9 | 9 | 18800 | 16700 | 65600 |
| G mean | 226134.74 | 18.15 | 1255.06 | 1451.26 | 14026.81 | 214441.56 |
| t-test log vs. HELA | | $9.626 \times 10^{-5}$ | 0.0344 | 0.0395 | 0.1809 | 0.978 |

Values of 9 and 10 were used for calculations of t-test; however, *Chlamydia* was not detected.

TABLE 11

Body Weight Maximum Loss Measured after Challenge 11 Weeks Post-Second Immunization

| Mouse # in Group | Group | | | | | |
|---|---|---|---|---|---|---|
| | 1 HeLa | 2 CT800 | 3 Ec10:14 | 4 Ct10:18 | 5 Ps10:12 | 6 Prot10 |
| 1 | 28.3 | 11.3 | 11.5 | 18.2 | 21.2 | 16.9 |
| 2 | 19.9 | 7.9 | 21.1 | 32.7 | 15.8 | 22.5 |
| 3 | 29.4 | 8.6 | 22.6 | 25.5 | 24.8 | 16.8 |
| 4 | 39.3 | 13.2 | 9 | 23.3 | 8.8 | 33.3 |
| 5 | 30.7 | 15.7 | 6.2 | 23.7 | 5.3 | 16.1 |
| 6 | 19 | 15.1 | 39.1 | 38.4 | 6.8 | 35.7 |
| 7 | 38.8 | 12.4 | 22.3 | 25.6 | 12.5 | 38 |
| 8 | 34 | 17.7 | 15.8 | 28.6 | 15.5 | 27.9 |
| 9 | 19.7 | 15.5 | 24 | 24.6 | | 18.5 |
| 10 | 27.2 | 13.3 | | 38.1 | | 26.9 |
| G mean | 27.72 | 12.69 | 16.70 | 27.19 | 12.26 | 24.04 |
| t-test log vs. HELA | | $3.74 \times 10^{-6}$ | 0.02195 | 0.8653 | 0.000739 | 0.30697 |

TABLE 12

Lung *Chlamydia* IFUs Quantified after Challenge 11 Weeks Post-Second Immunization

| Mouse # in Group | Group | | | | | |
|---|---|---|---|---|---|---|
| | 1 HeLa | 2 CT800 | 3 Ec10:14 | 4 Ct10:18 | 5 Ps10:12 | 6 Prot10 |
| 1 | 192000 | 9 | 9 | 2310 | 29100 | 9 |
| 2 | 9090 | 9 | 153000 | 576000 | 17500 | 28300 |
| 3 | 476000 | 9 | 338000 | 20800 | 17900 | 5000 |
| 4 | 2225000 | 9 | 38000 | 31700 | 9 | 2100000 |
| 5 | 2890000 | 9 | 8000 | 5000 | 9 | 100000 |
| 6 | 21800 | 9 | 2500000 | 414000 | 9 | 3270000 |
| 7 | $1.12 \times 10^7$ | 9 | 6430 | 10000 | 30800 | 3330000 |
| 8 | $4.17 \times 10^7$ | 9 | 18600 | 45000 | 30000 | 95500 |
| 9 | 17500 | 9 | 37400 | 11400 | | 10000 |
| 10 | 216000 | 10 | | 680000 | | 1500000 |
| G mean | 427705.51 | 9.10 | 22671.14 | 38034.29 | 1254.65 | 72783.09 |
| t-test log vs. HELA | | $5.44 \times 10^{-10}$ | 0.0597 | 0.0421 | 0.00259 | 0.268 |

Values of 9 and 10 were used for calculations of t-test; however, *Chlamydia* was not detected.

Example 16

Protollin Stimulates Protective Innate Immunity Against Influenza Virus Infection Experiment 1

Figure 8A:
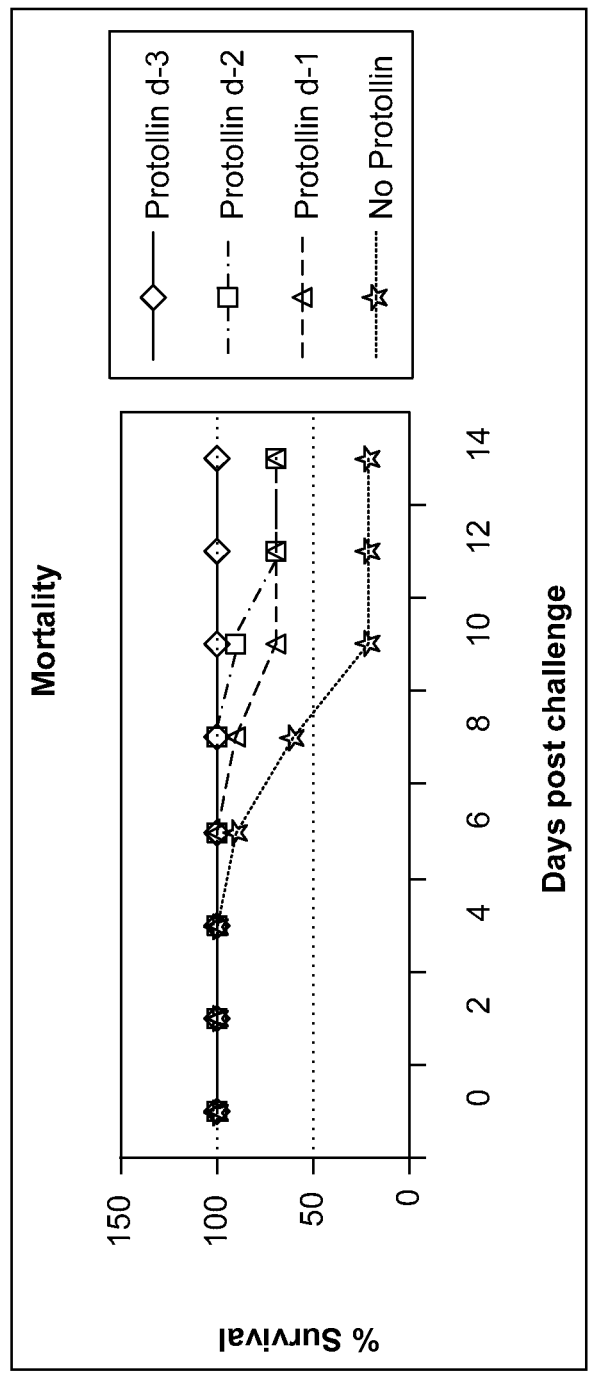
FIG. 8A shows mortality and FIG. 8B illustrates morbidity (percent weight change) of mice that were immunized with Protollin 1 day (d-1), 2 days (d-2), or 3 days (d-3) prior to challenge by inhalation administration of mouse-adapted A/H3 influenza virus.
Figure 8B:
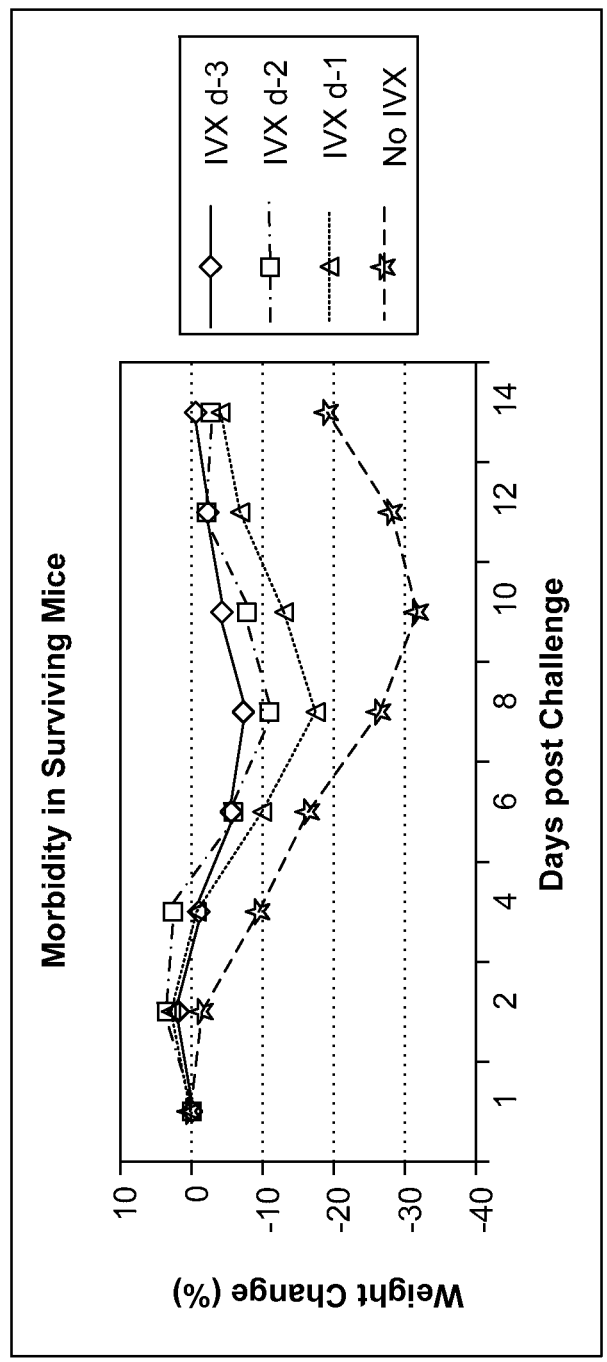

Mice were given a single intranasal dose of Protollin (containing approximately 5 µg each of *Neisseria* OMPs and *S. flexneri* LPS) on day 1, 2, or 3 prior to intranasal challenge with 25 $LD_{50}$ mouse-adapted A/H3 influenza virus (Hong Kong). The virus was propagated according to standard methods (original seed stock was a generous gift from Dr. Phil Wyde (Baylor University, Waco, Tex.)). Mice were weighed prior to challenge and every 2 days after for a total of 14 days. Morbidity was assessed by weighing individual survivors and expressing weight change as the percent of weight on the day of challenge (see FIG. 8B). The day of any death was also recorded (see FIG. 8A). All mice that received Protollin 3 days prior to challenge survived and also lacked acute morbidity (maximum weight loss was 7%). Seventy percent survival was observed in the groups of animals that received Protollin 1 or 2 days prior to challenge; however, animals in both groups suffered 15-18% weight loss. The statistical significance of delay to time of death for each group as a whole was assessed by the Wilcoxon signed-rank test. All mice that received Protollin 72 hours prior to challenge survived. Compared to the survival data for the negative control group (no Protollin), survival of mice given Protollin on day 3 prior to challenge was highly significant (P≤0.001; Fisher's Exact Probability test). Seventy percent of mice that received Protollin either 1 or 2 days prior to challenge survived (P≤0.07 compared with the negative control group). While the absolute number of survivors in these two groups was not significantly different from the number of survivors in the control group, the time to death was significantly prolonged in both groups compared to control mice (P≤0.05 or ≤0.01 respectively in the groups given Protollin 1 or 2 days prior to challenge).

Morbidity was monitored in surviving mice in all groups, using loss of body weight (relative to the day of challenge) as a surrogate of morbidity resulting from infection. All mice lost weight during the period of monitoring although the mice given Protollin lost less weight than control mice given PBS. Weight loss was also dependent on the time between Protollin administration and challenge. Mice given Protollin 3 days prior to challenge suffered less weight loss than those given Protollin 2 days before challenge, and the animals given Protollin 2 days before challene lost less weight than those given Protollin one day before challenge. Until day 8 (after which time the limited numbers of survivors in the control group made statistical comparisons unreliable), control mice lost significantly more weight than mice that received Protollin (on days 4 and 6 post challenge, P≤0.001 vs all mice given Protollin; on day 8 post challenge, P≤0.01 and P≤0.05, respectively, vs mice given Protollin 3 days or 2 days prior to challenge). These results showed that Protollin induced innate responses that protected mice against death following lethal, live virus challenge and significantly reduced morbidity associated with infection.

Experiment 2

In addition, duration of protection within a limiting dose range was analyzed. A single dose of 3, 1, or 0.3 µg Protollin was administered to groups of mice (10 animals per group) on day 15, 12, 9, 6, or 3 prior to challenge with 25 $LD_{50}$ of a mouse-adapted A/H3 influenza virus. Humane endpoint indicators for this experiment were based on body weight, appearance, and behavior. Animals were scored from 0-3 in each category as follows. For body weight, a score of 0 indicated no loss of start-of-study body weight; 1 indicated 10% or less loss of start-of-study body weight; 2 indicated 11-19% loss of start-of-study body weight; and 3 indicated 20% or more loss of start-of-study body weight. For appearance, a score of 0 indicated normal appearance; a score of 1 indicated fur erected; a score of 2 indicated fur erected oily, nasal and/or ocular discharge; a score of 3 indicated hunched back, severe dehydration. For behavior, a score of 0 indicated normal behavior; a score of 1 indicated abnormal gait and weakness; a score of 2 indicated activity decreased, severe tremors; and a score of 3 indicated inactive. Mice with a score of 3 or more in single or combined symptoms were euthanized.

All mice in the control group (no Protollin) and the groups given 0.3 µg Protollin met endpoint criteria six days post-challenge and were euthanized. Of the animals receiving 1 µg Protollin, all were euthanized 6 days post challenge with the exception of animals in the group dosed 3 days prior to challenge, in which 5 mice survived until 8 days post challenge. Compared to the control group, survival of animals in this group constituted a significant delay in the time to death (P<0.05 for the group as a whole).

In the groups given 3 µg Protollin, 30% of animals dosed 6 days prior to challenge survived the study; the remaining 70% met endpoint criteria between 6 and 8 days post-challenge. Although these results suggest that the number of survivors was not significantly different from the control group (by Fisher's Exact Probability Test), the time to death for the group as a whole was significantly different from the control group (P<0.001). Fifty percent of mice receiving 3 µg Protollin, 3 days prior to challenge, survived the study (P<0.05 by Fisher's Exact Probability Test); the other 50% of mice reached endpoint criteria between 6 and 8 days post-challenge. Again for the group as a whole, the time to death was significantly different from the control group (P<0.001).

In these experiments, the induction of a protective nonspecific, antigen-independent immune response occurred above a threshold range of 3-5 µg Protollin, and when Protollin was administered 3-6 days prior to challenge. Furthermore, co-administration of an influenza antigen (derived from a homotypic variant of the mouse adapted A/H3 influenza strain used for challenge from) with Protollin did not inhibit the protective innate immune responses. Induction of a protective innate immune response was also induced by Protollin comprising another smooth LPS from a Gram-negative bacterium—in this instance a non-pathogenic strain of *E. coli* (*E. coli* O17).

Experiment 3

Groups of mice were given Protollin 8, 6, 4, and 2 days before challenge and on the day of challenge (30 minutes prior to challenge). Other groups of mice were dosed at the same time with Protollin in combination with influenza antigen derived from a homotypic variant virus of the mouse adapted A/H3 influenza strain used for challenge. Mice were challenged with approx 40 $LD_{50}$ of mouse adapted A/H3 live virus and monitored for 14 days post challenge as described above.

At the 40 $LD_{50}$ dose of virus, no animals in the PBS only control group survived. Despite this lethal challenge, 50% of mice that had received Protollin 6 days prior to challenge survived (P≤0.05 compared with control mice; Fisher's Exact Probability test). Groups of animals that received Protollin 4-6 days prior to challenge had the greatest percent survival. Monitoring changes in body weight (a surrogate of morbidity following infection) in surviving mice indicated that the optimal time for dosing was approximately 4 days prior to challenge. All mice dosed 2, 4, or 6 days prior to challenge lost less body weight than the other mice and began recovering body weight sooner.

Of the mice given Protollin in combination with antigen prior to lethal challenge, most survivors were in the groups dosed 4 and 6 days prior to challenge (100% and 60%; P≤0.001 and 0.01, respectively, compared to controls). Specific antibody (IgG) responses to the influenza antigen would be expected to be less than optimal within 4-6 days of receiving antigen. As indicated in the prior experiments, changes in body weight confirmed that induction of innate immune responses and subsequent protection against mortality and morbidity occurred when mice were dosed during a 2-6 day period prior to challenge.

Example 17

Allergen-Induced Mouse Model of Allergic Asthma

This Example describes a mouse allergic asthma animal model. Mice were exposed to birch pollen extract (BPEx) multiple times to stimulate inflammation and airway hyperresponsiveness (i.e., simulating an allergic reaction). Briefly, six to eight week-old BALB/c mice were sensitized on day 0 by a single intraperitoneal (i.p.) injection with 8 μg of BPEx (Greer Laboratories, Inc.) and 1 mg aluminum hydroxide (alum) (ALHYDROGEL®, Superfos Biosector, Kvistgard, Denmark) in 150 μl phosphate buffered saline (PBS). After sensitization, mice were then challenged intranasally (i.n.) under light halothane anesthesia once daily on days 15, 16, and 17 with 10 μg BPEx in 36 μl PBS (18 μl per nostril). Controls included (1) sham sensitized mice, who received 150 μl PBS i.p. on day 0 and then were challenged i.n. under light halothane anesthesia once daily on days 15, 16, and 17 with 10 μg BPEx in 36 μl PBS (18 μl per nostril), and (2) sham challenged mice, who were sensitized i.p. on day 0 with 8 μg BPEx and 1 mg alum and then received i.n., under light anesthesia, 36 μl PBS (18 μl per nostril) once daily on days 15, 16, and 17. Eight mice received each type of treatment. After sensitization and challenge, mice were given an intravenous (i.v.) bolus of methacholine (MCh), a bronchoconstrictor, to induce airway hyperresponsiveness (AHR). Two days after the final challenge (i.e., on day 19), airway responses (respiratory resistance and elastance) to MCh treatment were measured. Additional analyses were performed to assess inflammation.

Example 18

Analysis of Allergen-Induced Mouse Model of Allergic Asthma

Airway Hyperresponsiveness (AHR)

Determination of AHR was performed as follows. BALB/c mice treated as described in Example 17 were sedated by an i.p. injection of xylazine hydrochloride (10 mg/kg) and subsequently anaesthetized with sodium pentobarbital (30 mg/kg). A small incision was made in the neck to isolate the jugular vein, which was catheterized. A tracheostomy was performed, and a tube was inserted into the trachea so that the animal could be mechanically ventilated. Animals were ventilated quasi-sinusoidally (inspiratory to expiratory ratio of 1:1) using a small animal ventilator (FlexiVent; SCIREQ™, Montreal, Canada) with the following settings: a respiratory rate of 150 breaths/min, a tidal volume of 0.15 ml, and a positive end expiratory pressure (PEEP) level of 1.5 cm $H_2O$. Mice received an intravenous injection of pancuronium bromide (0.5 mg/kg) to induce paralysis so that the animals could be mechanically ventilated. Heart rate was monitored via EKG to ensure that animals were deeply anesthetized. Following inflation to airway pressure of 30 cm $H_2O$ to provide a standard volume history, MCh was given via the jugular cannula in doubling doses from 20 to 640 μg/ml. Respiratory system resistance and elastance were measured during the oscillation equal to those used during mechanical ventilation before administration of MCh and repeated every 15 seconds after delivery of MCh, with peak values reported. The airway resistance ($R_L$) measurement provides a quantitative assessment of the level of constriction in the lungs—that is, an increase in airway resistance represents an increase of airway obstruction, which may be caused by an inflammatory response. The airway elastance ($E_L$) is a measure of the elastic rigidity of the lung; therefore, increased elastance values indicate an increased stiffness of the lungs. $R_L$ and $E_L$ were calculated with software provided by the FlexiVent manufacturer using multiple linear regression to obtain the best fit for the following equation:

$$P = P_{res} + P_{el} + P_{in} = FR_L + VE_L + K$$

in which P is gas pressure applied by the mechanical respirator; $P_{res}$ is resistive pressure; $P_{el}$ is elastic pressure; $P_{in}$ is an inertive pressure; F is flow of gas; V is lung volume relative to functional residual capacity; and K is a constant (Irvin et al., Respir. Res. 4:4 (2003)). Airway resistance and airway elastance are presented as mean values±SEM. Student's t-test was used to determine the level of difference between animal groups.

Serum

Immediately following measurements of airway responsiveness, mice were sacrificed by exsanguination via cardiac puncture, the collected blood was centrifuged, and the resulting serum was transferred to a clean tube and frozen. The sera were analyzed using ELISAs to determine whether BPEx-specific antibodies were present.

Bronchoalveolar Lavages (BALs) and Eosinophilia

Following exsanguination, the descending aorta was cut and the heart was perfused with 5 ml saline buffer to remove blood from the lungs prior to performing BALs. A total of 4.6 ml saline buffer was instilled through a tracheostomy canula in an initial 0.6 ml volume followed by 4 successive 1 ml volumes. The return from the first 0.6 ml of lavage fluid was centrifuged, and the supernatant was analyzed by ELISA to detect antibodies and cytokines.

The cells harvested from the initial lavage fluid were resuspended in saline buffer and then pooled with cells recovered by centrifugation from the subsequent four aliquots of lavage fluid. Total cell numbers were counted by using trypan blue stain and a hemocytometer. The cytospin slides of BAL cells were prepared using a cytocentrifuge (Cytospin model II; Shandon, Pittsburgh, Pa.).

Eosinophilia was evaluated in BALs by measuring the percent of differentially stained macrophages, eosinophils, neutrophils, lymphocytes, and epithelial cells (Diff-Quick, International Medical Equipment) in the lavage samples. Differential cell counts were determined by light microscopy from a count of at least 200 cells.

Lung Tissue

Following BALs, the lungs of each mouse are exposed and the left lobe is clamped. The largest lobe of the right lung is put directly into 10% paraffin. The second largest lobe is put in an RNA extraction solution (RNEASY® RLT buffer; QIAGEN Inc, Mississauga, Ontario), which is kept at 4° C. overnight and then stored frozen at −70° C. for subsequent use for real-time quantitative polymerase chain reaction (QPCR).

The two other lobes of the right lung are transferred to an Eppendorf tube, immersed in liquid nitrogen, and then stored at −70° C. Lung homogenates are prepared and supernatants are analyzed by ELISA for BPEx-specific and total antibodies and for cytokines levels. The left lung is inflated with 5% optimal cutting temperature (OCT) embedding compound (Miles Labs, Elkhart, Ind.) (approximately 25 cm pressure), put in 100% OCT with immersion in isopentanol (beaker in liquid nitrogen; i.e., snap frozen), and stored at −70° C.

Lung tissues in paraffin are sliced, and sections are stained with periodic acid-Schiff (PAS staining) for evaluation of mucus production. Paraffin sections are also analyzed for the presence of collagen (Van Gieson staining) and eosinophils (Giemsia staining). In addition, airway damage is assessed in the stained sections. Frozen lung tissues in OCT embedding compound are sliced and analyzed by in situ immunostaining. Eosinophils are quantified by immunostaining with an anti-mouse major basic protein (MBP) antibody. Lung sections are used for the identification of cytokines (anti-IL-4, anti-IL-5, or anti-IFN-γ), T-cells (anti-CD3), and macrophages (anti-CD68).

ELISAs of Antibody and Cytokine Levels

ELISAs are used to identify specific antibodies (IgA, IgE, IgG1, and IgG2a) and specific cytokines (IL-4, IL-5, IL-10, IL-13, TNF-α, and IFN-γ). Sera, BALs, and lung homogenates are analyzed for BPEx-specific and total IgE using the OptEIA™ mouse IgE set (BD Pharmingen, Mississauga, Ontario). Sera, BALs, and lung homogenates are analyzed for BPEx-specific and total IgG1 and IgG2a using reagents from Southern Biotech Associates, Inc. (Birmingham, Ala.). Sera, BALs, and lung homogenates are analyzed for BPEx-specific and total IgA using reagents from Bethyl Laboratories, Inc. (Montgomery, Tex.). BALs and lung homogenates are analyzed for the level of IL-4, IL-5, IL-10, TNF-α, and IFN-γ using reagents of BD Pharmingen (Mississauga, Ontario). BALs and lung homogenates are analyzed for the level of IL-13 using reagents of R&D Systems (Minneapolis, Minn.). Antibody and cytokine titers are expressed as ng/ml and pg/ml, respectively, deduced from standards run in parallel with corresponding recombinant antibodies or cytokines.

Quantification of IL-4, IL-5, IL-10, IL-13, TNF-α, and IFN-γ by real-time, QPCR in lung samples kept frozen in RNA extraction solution (as described herein) are initiated by isolation of total cellular RNA using the QIAGEN RNE-ASY® Mini Kit (QIAGEN Inc.). The concentration of the RNA extracted is determined by measuring optical densities at 260 nm ($OD_{260}$), and purity is evaluated based on $OD_{260}/OD_{280}$ ratios equal to or greater than 1.8. Reverse transcription is performed on 1 μg RNA samples using OMNIS-CRIPT™ reverse transcriptase kits (QIAGEN Inc.) in a constant volume of 20 μl. A 1 μl volume from the resulting complementary DNA (cDNA) solutions is used for real-time QPCR reactions, which are performed on a LightCycler™ (Roche Diagnostics, Mannheim, Germany). The reactions include Sybr® Green I as a double-strand DNA-specific binding dye in the LightCycler™—primer set (Search Lc, Heidelberg, Germany) for a specific cytokine, or for the S9 ribosomal protein (control, house-keeping gene).

Airway hyperresponsiveness, as measured by both airway resistance (Table 13) and airway elastance (Table 14), increased in animals that received increasing quantities of MCh and that were sensitized and challenged with BPEx compared with mice that were either only sensitized or only challenged with BPEx. Following an intravenous injection of MCh at 320 μg/ml, sensitized/challenged mice had airway resistance (12.88 cm $H_2O$·sec/ml) and elastance (103.08 cm $H_2O$/ml) that were 2-fold higher than in sensitized/sham mice (p=0.014 and p=0.038, respectively) and sham/challenged mice (p=0.042 and p=0.084, respectively) (see Tables 13 and 14). Sensitized/challenged mice, following i.v. injection of MCh at 640 μg/ml, showed airway resistance of 36.63 cm $H_2O$·sec/ml and elastance of 359.88 cm $H_2O$/ml, which was 3- and 5-fold higher than in control mice that were only sensitized with BPEx (p=0.014 and p=0.028, respectively) and mice that were only challenged with BPEx (p=0.031 and p=0.062, respectively), respectively (see Tables 13 and 14).

TABLE 13

Mean Respiratory System Resistance (cm $H_2O$.s/ml) in Mouse Allergic Asthma Model

| | Mch (μg/ml) | | | | | | | |
|---|---|---|---|---|---|---|---|---|
| | baseline | 10 | 20 | 40 | 80 | 160 | 320 | 640 |
| Group 1: sens/chal | 0.66 | 0.68 | 0.73 | 0.90 | 1.59 | 4.24 | 12.88 | 36.63 |
| Group 2: sens/sham | 0.69 | 0.70 | 0.75 | 0.93 | 1.40 | 2.58 | 5.67 | 10.03 |
| Group 3: sham/chal | 0.69 | 0.71 | 0.78 | 0.97 | 1.63 | 3.01 | 6.11 | 8.19 |

Data were analyzed by t-test:
Group 1 vs Group 2 at 320 μg/ml MCh: p = 0.014
Group 1 vs Group 3 at 320 μg/ml MCh: p = 0.042
Group 1 vs Group 2 at 640 μg/ml MCh: p = 0.014
Group 1 vs Group 3 at 640 μg/ml MCh: p = 0.031

TABLE 14

Mean Respiratory System Elastance (cm $H_2O$)/ml) in Mouse Allergic Asthma Model

| | Mch (μg/ml) | | | | | | | |
|---|---|---|---|---|---|---|---|---|
| | baseline | 10 | 20 | 40 | 80 | 160 | 320 | 640 |
| Group 1: sens/chal | 28.89 | 30.25 | 31.89 | 33.99 | 37.42 | 47.52 | 103.08 | 359.88 |
| Group 2: sens/sham | 27.63 | 28.74 | 30.14 | 31.70 | 34.29 | 40.54 | 53.08 | 71.31 |
| Group 3: sham/chal | 28.48 | 29.84 | 31.43 | 33.58 | 37.34 | 44.38 | 57.82 | 64.21 |

Data were analyzed by t-test:
Group 1 vs Group 2 at 320 μg/ml MCh: p = 0.038
Group 1 vs Group 3 at 320 μg/ml MCh: p = 0.084
Group 1 vs Group 2 at 640 μg/ml MCh: p = 0.028
Group 1 vs Group 3 at 640 μg/ml MCh: p = 0.062

In addition, the combination of sensitization and challenge with BPEx in BALB/c mice resulted in eosinophilia. Macrophages, neutrophils, eosinophils, lymphocytes, and epithelial cells were enumerated in bronchoalveolar lavage samples (BALs). The percent of each cell type per total number of cells is presented in Table 15. In these mice, the percentage of eosinophils (8.26%) and lymphocytes (10.16%) was 12- and 4-fold higher, respectively, than in control mice that were only sensitized with BPEx (p=0.036 and p=0.024, respectively); these values were 3- and 2-fold higher, respectively, than in mice that were challenged only with BPEx (p=0.204 and p=0.320, respectively)

TABLE 15

Differential Cell Counts (%) in BALs in Mouse Allergic Asthma Model

| Cell Type | Macrophages | Neutrophils | Eosinophils | Lymphocytes | Epithelial Cells |
|---|---|---|---|---|---|
| Group 1: sens/chal | 74.13 | 2.90 | 8.26 | 10.16 | 4.64 |
| Group 2: sens/sham | 86.42 | 3.12 | 0.66 | 2.34 | 6.36 |
| Group 3: sham/chal | 73.08 | 7.01 | 2.56 | 5.91 | 6.61 |

Data were analyzed by t-test.

Example 19

Protollin-Induced Suppression of Airway Hyperresponsiveness and Airway Inflammation The allergic asthma mouse model (as described in Example 18) was used to analyze compositions for suppressing an inflammatory immune response and airway hyperresponsiveness (i.e., suppressing an allergic reaction). Briefly, six to eight-week old BALB/c mice were sensitized i.p. on day 0 with 8 µg of BPEx and 1 mg alum in 150 µl PBS. On days 7, 10, and 13 after sensitization, groups of eight mice were each immunized i.n. with 10 µl (5 µl per nostril) solutions of (1) PBS; (2) 10 µg BPEx; (3) 10 µg BPEx mixed with 10 µg Protollin; or (4) 10 µg Protollin alone. After immunization, the mice were then challenged i.n. under light halothane anesthesia once daily on days 15, 16, and 17 with 10 µg BPEx in 36 µl PBS (18 µl per nostril). Two days after the final challenge (i.e., on day 19), mice were given an i.v. bolus of MCh (20-640 µg/ml). Airway responses (respiratory resistance and elastance) to MCh treatment, inflammation, and eosinophilia were determined as described in Example 18.

Sensitized mice that were immunized with a composition comprising BPEx with Protollin or Protollin alone and subsequently challenged i.n. with BPEx, showed reduced airway resistance and elastance in AHR measurements as intravenous quantities of MCh were increased (see Tables 16 and 17). Following an intravenous injection of MCh at 640 µg/ml, mice treated with BPEx mixed with Protollin had reduced airway resistance (12.54 cm $H_2O$·sec/ml) and elastance (99.73 cm $H_2O$/ml) by approximately 43% and 48%, respectively, compared with mice treated with only PBS (p=0.028 and p=0.050, respectively) or only BPEx (p=0.132 and p=0.220, respectively). Similarly, Protollin adjuvant alone also lowered airway resistance (9.71 cm $H_2O$·sec/ml) and elastance (69.24 cm $H_2O$/ml) by approximately 56% and 64%, respectively, compared to mice treated with only PBS (p=0.005 and p=0.009, respectively) or only BPEx (p=0.029 and p=0.074, respectively).

TABLE 16

Mean Respiratory System Resistance (cm $H_2O$.s/ml) Post-Administration of Protollin:Birch Pollen Extract (BPEx) in Mouse Allergic Asthma Model

| | Mch (µg/ml) | | | | | | |
|---|---|---|---|---|---|---|---|
| | baseline | 20 | 40 | 80 | 160 | 320 | 640 |
| Group 1: PBS | 0.61 | 0.68 | 0.87 | 1.48 | 3.27 | 9.72 | 24.13 |
| Group 2: BPEx | 0.67 | 0.71 | 0.90 | 1.47 | 3.41 | 8.81 | 19.87 |
| Group 3: BPEx:Protollin | 0.63 | 0.68 | 0.79 | 1.17 | 2.39 | 6.03 | 12.54 |
| Group 4: Protollin | 0.60 | 0.64 | 0.75 | 1.06 | 2.00 | 4.59 | 9.71 |

Data were analyzed by t-test:
Group 3 vs Group 1 at 640 µg/ml MCh: p = 0.028
Group 3 vs Group 2 at 640 µg/ml MCh: p = 0.132
Group 4 vs Group 1 at 640 µg/ml MCh: p = 0.005
Group 4 vs Group 2 at 640 µg/ml MCh: p = 0.029

TABLE 17

Mean Respiratory System Elastance (cm $H_2O$)/ml) Post-Administration of Protollin:Birch Pollen Extract (BPEx) in Mouse Allergic Asthma Model

| | Mch (µg/ml) | | | | | | |
|---|---|---|---|---|---|---|---|
| | baseline | 20 | 40 | 80 | 160 | 320 | 640 |
| Group 1: PBS | 26.33 | 28.07 | 30.29 | 35.05 | 43.20 | 75.16 | 205.50 |
| Group 2: BPEx | 25.61 | 27.23 | 29.27 | 32.33 | 40.91 | 75.15 | 180.82 |
| Group 3: BPEx:Protollin | 24.91 | 26.56 | 28.21 | 30.81 | 35.50 | 48.69 | 99.73 |
| Group 4: Protollin | 24.77 | 26.15 | 27.98 | 30.11 | 34.83 | 45.50 | 69.24 |

Data were analyzed by t-test:
Group 3 vs Group 1 at 640 µg/ml MCh: p = 0.050
Group 3 vs Group 2 at 640 µg/ml MCh: p = 0.220
Group 4 vs Group 1 at 640 µg/ml MCh: p = 0.009
Group 4 vs Group 2 at 640 µg/ml MCh: p = 0.074

The extent of airway inflammation in animals was determined by enumerating immune cells present in bronchoalveolar lavage (BAL) samples from mice treated with PBS, BPEX, BPEX+Protollin, and Protollin alone. The data are presented in Table 18. Animals that were treated with the allergen BPEx mixed with Protollin had reduced levels of BAL eosinophils, approximately 56% and 43%, compared to mice that were treated with only PBS (p=0.36) or with only BPEx (p=0.29), respectively. Treatment with BPEx plus Protollin also reduced the number of lymphocytes in BAL by approximately 51% and 40% compared to animals treated with PBS only (p=0.04) or BPEx alone (p=0.26), respectively. Animals treated with Protollin alone had reduced levels of BAL eosinophils, approximately 71% and 63%, compared with the number of eosinophils from mice treated with only PBS (p=0.28) or BPEx alone (p=0.14), respectively. Treating mice with Protollin alone also reduced the number of lymphocytes, approximately 45% and 32% compared with mice treated with PBS only (p=0.10) or BPEx (p=0.40), respectively. Lung samples were analyzed for the presence of Goblet cells. Reduction in airway inflammation was also indicated by the lower percent of mice that had mucous-producing Goblet cells in the bronchioles in the group treated with BPEx plus Protollin or Protollin alone (29%; that is, 2 mice out of 7 mice in each group had at least 1% Goblet cells of the total number of bronchial epithelial cells) compared with mice treated with PBS only (75%; 5 of 7 mice) or PBEx only (50%; 3 of 6 mice).

Antibodies present in sera that specifically bound to BPEx were detected by ELISA using the method described in Example 18. BPEx-specific IgE and IgG1 were measured at low levels in mouse sera while BPEx-specific serum IgG2a was poorly detectable (see Table 19). Intranasal treatment of animals with Protollin alone reduced the levels of BPEx-specific IgE and IgG1 by at least 50% compared with mice treated with only PBS or only BPEx.

TABLE 18

Airway Inflammation: Immune Cells in Bronchoalveolar Lavage and Percent Mice with Mucus Producing Goblet Cells

| Treatment | Macrophages/ Monocytes ($\times 10^4$/ml) | Neutrophils ($\times 10^4$/ml) | Eosinophils ($\times 10^4$/ml) | Lymphocytes ($\times 10^4$/ml) | Epithelial cells ($\times 10^4$/ml) | Goblet cells (% mice) |
|---|---|---|---|---|---|---|
| PBS | 83.0 | 9.1 | 14.7 | 9.4 | 18.5 | 71% |
| BPEx | 93.6 | 7.0 | 11.4 | 7.7 | 15.0 | 50% |
| BPEx/Protollin | 66.0 | 5.4 | 6.5 | 4.6 | 10.4 | 29% |
| Protollin | 92.7 | 4.9 | 4.2 | 5.2 | 14.4 | 29% |

TABLE 19

Allergen Specific Antibody Levels in Sera

| Treatment | IgE ($\times 100$ ng/ml) | IgG1 ($\times 1000$ ng/ml) |
|---|---|---|
| PBS | 80.77 | 28.800 |
| BPEx | 27.28 | 15.945 |
| BPEx/Protollin | 31.53 | 35.839 |
| Protollin | 9.18 | 7.931 |

Those skilled in the art will recognize, or be able to ascertain, using no more than routine experimentation, many equivalents to the specific embodiments of the invention described herein. Such equivalents are intended to be encompassed by the following claims.

We claim the following:

1. A method for treating an allergic reaction, comprising: administering an immunomodulatory composition to a subject sensitized to an inhaled allergen, wherein said allergen is a pollen, in an amount sufficient to suppress an inflammatory immune response, wherein the immunomodulatory composition consist of Proteosomes and a liposaccharide, wherein Proteosomes are obtained from a *Neisseria* species, and wherein the liposaccharide is obtained from the *Neisseria* species or from a different gram-negative bacterial species, and wherein the allergen is (a) different from the *Neisseria* species from which the Proteosomes are obtained and b) different from the gram-negative bacteria species from which the liposaccharide is obtained.

2. The method according to claim 1 wherein the immunomodulatory composition is administered by a route selected from at least one of mucosal, enteral, sublingual, parenteral, transdermal, transmucosal, nasal, and inhalation.

3. The method according to claim 2 wherein the immunomodulatory composition is administered nasally.

4. The method according to claim 1 wherein the Proteosomes and liposaccharide of the immunomodulatory composition are obtained from the same *Neisseria* species.

5. The method according to claim 1 wherein the liposaccharide of the immunomodulatory composition is obtained from at least one of *Shigella* species, *Chlamydia* species, *Yersinia* species, *Pseudomonas* species, *Plesiomonas* species, *Escherichia* species, *Porphyromonas* species, and *Salmonella* species.

6. The method according to claim 1 wherein the Proteosomes of the immunomodulatory composition are obtained from *Neisseria meningitides*, and the liposaccharide of the immunomodulatory composition is obtained from *Shigella flexneri*.

7. The method according to claim 1 wherein the pollen is birch pollen.

8. The method according to claim 1 wherein the allergic reaction is asthma.

9. The method according to claim 1 wherein the allergic reaction is at least one of allergic alveolitis and allergic rhinitis.

* * * * *